(12) United States Patent
Davisson et al.

(10) Patent No.: US 11,400,130 B2
(45) Date of Patent: *Aug. 2, 2022

(54) INHIBITORS FOR PROLIFERATING CELL NUCLEAR ANTIGEN AND USES

(71) Applicant: Purdue Research Foundation, West Lafayette, IN (US)

(72) Inventors: Vincent Jo Davisson, West Lafayette, IN (US); Matthew David Bartolowits, West Lafayette, IN (US); Jonathon Michael Gast, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/991,534

(22) Filed: Aug. 12, 2020

(65) Prior Publication Data

US 2022/0160813 A1     May 26, 2022

Related U.S. Application Data

(63) Continuation of application No. 15/781,742, filed as application No. PCT/US2016/065062 on Dec. 6, 2016, now Pat. No. 10,758,588.

(60) Provisional application No. 62/263,790, filed on Dec. 7, 2015.

(51) Int. Cl.
| | | |
|---|---|---|
| *A61K 38/06* | (2006.01) | |
| *A61K 38/00* | (2006.01) | |
| *C07K 5/08* | (2006.01) | |
| *C07K 5/087* | (2006.01) | |
| *A61K 45/06* | (2006.01) | |
| *C07K 5/083* | (2006.01) | |
| *C07K 5/068* | (2006.01) | |

(52) U.S. Cl.
CPC ............ *A61K 38/06* (2013.01); *A61K 38/00* (2013.01); *A61K 45/06* (2013.01); *C07K 5/08* (2013.01); *C07K 5/0806* (2013.01); *C07K 5/0812* (2013.01); *C07K 5/06086* (2013.01)

(58) Field of Classification Search
CPC ........ A61K 38/06; A61K 38/00; A61K 45/06; C07K 5/08; C07K 5/0812; C07K 5/0806; C07K 5/06086
See application file for complete search history.

(56) References Cited

U.S. PATENT DOCUMENTS 10,758,588 B2 *   9/2020   Davisson ............... A61K 38/00

* cited by examiner

*Primary Examiner* — Sudhakar Katakam
(74) *Attorney, Agent, or Firm* — Liang Zeng Yan; Purdue Research Foundation

(57) ABSTRACT

The present invention relates to series of compounds as an inhibitor targeting Proliferating Cell Nuclear Antigen (PCNA). Pharmaceutical compositions of those compounds and methods of using them in the treatment of cancer are within the scope of this disclosure.

18 Claims, 17 Drawing Sheets
Specification includes a Sequence Listing.

SEQUENCE LISTING

```
<160> NUMBER OF SEQ ID NOS: 4

<210> SEQ ID NO 1
<211> LENGTH: 261
<212> TYPE: PRT
<213> ORGANISM: Homo sapiens

<400> SEQUENCE: 1

Met Phe Glu Ala Arg Leu Val Gln Gly Ser Ile Leu Lys Lys Val Leu
1               5                   10                  15

Glu Ala Leu Lys Asp Leu Ile Asn Glu Ala Cys Trp Asp Ile Ser Ser
            20                  25                  30

Ser Gly Val Asn Leu Gln Ser Met Asp Ser Ser His Val Ser Leu Val
        35                  40                  45

Gln Leu Thr Leu Arg Ser Glu Gly Phe Asp Thr Tyr Arg Cys Asp Arg
    50                  55                  60

Asn Leu Ala Met Gly Val Asn Leu Thr Ser Met Ser Lys Ile Leu Lys
65                  70                  75                  80

Cys Ala Gly Asn Glu Asp Ile Ile Thr Leu Arg Ala Glu Asp Asn Ala
                85                  90                  95

Asp Thr Leu Ala Leu Val Phe Glu Ala Pro Asn Gln Glu Lys Val Ser
            100                 105                 110

Asp Tyr Glu Met Lys Leu Met Asp Leu Asp Val Glu Gln Leu Gly Ile
        115                 120                 125
```

-continued

Pro Glu Gln Glu Tyr Ser Cys Val Val Lys Met Pro Ser Gly Glu Phe
    130                 135                 140

Ala Arg Ile Cys Arg Asp Leu Ser His Ile Gly Asp Ala Val Val Ile
145                 150                 155                 160

Ser Cys Ala Lys Asp Gly Val Lys Phe Ser Ala Ser Gly Glu Leu Gly
                165                 170                 175

Asn Gly Asn Ile Lys Leu Ser Gln Thr Ser Asn Val Asp Lys Glu Glu
            180                 185                 190

Glu Ala Val Thr Ile Glu Met Asn Glu Pro Val Gln Leu Thr Phe Ala
        195                 200                 205

Leu Arg Tyr Leu Asn Phe Phe Thr Lys Ala Thr Pro Leu Ser Ser Thr
210                 215                 220

Val Thr Leu Ser Met Ser Ala Asp Val Pro Leu Val Val Glu Tyr Lys
225                 230                 235                 240

Ile Ala Asp Met Gly His Leu Lys Tyr Tyr Leu Ala Pro Lys Ile Glu
                245                 250                 255

Asp Glu Glu Gly Ser
            260

<210> SEQ ID NO 2
<211> LENGTH: 16
<212> TYPE: PRT
<213> ORGANISM: Artificial sequence
<220> FEATURE:
<223> OTHER INFORMATION: POGO Ligase Peptide

<400> SEQUENCE: 2

Ser Ala Val Leu Gln Lys Lys Ile Thr Asp Tyr Phe His Pro Lys Lys
1               5                   10                  15

<210> SEQ ID NO 3
<211> LENGTH: 268
<212> TYPE: PRT
<213> ORGANISM: Artificial sequence
<220> FEATURE:
<223> OTHER INFORMATION: (His)6-PCNA

<400> SEQUENCE: 3

Met His His His His His Met Phe Glu Ala Arg Leu Val Gln Gly
1               5                   10                  15

Ser Ile Leu Lys Lys Val Leu Glu Ala Leu Lys Asp Leu Ile Asn Glu
            20                  25                  30

Ala Cys Trp Asp Ile Ser Ser Ser Gly Val Asn Leu Gln Ser Met Asp
        35                  40                  45

Ser Ser His Val Ser Leu Val Gln Leu Thr Leu Arg Ser Glu Gly Phe
    50                  55                  60

Asp Thr Tyr Arg Cys Asp Arg Asn Leu Ala Met Gly Val Asn Leu Thr
65                  70                  75                  80

Ser Met Ser Lys Ile Leu Lys Cys Ala Gly Asn Glu Asp Ile Ile Thr
                85                  90                  95

Leu Arg Ala Glu Asp Asn Ala Asp Thr Leu Ala Leu Val Phe Glu Ala
            100                 105                 110

Pro Asn Gln Glu Lys Val Ser Asp Tyr Glu Met Lys Leu Met Asp Leu
        115                 120                 125

Asp Val Glu Gln Leu Gly Ile Pro Glu Gln Glu Tyr Ser Cys Val Val
    130                 135                 140

Lys Met Pro Ser Gly Glu Phe Ala Arg Ile Cys Arg Asp Leu Ser His
145                 150                 155                 160

```
Ile Gly Asp Ala Val Val Ile Ser Cys Ala Lys Asp Gly Val Lys Phe
                165                 170                 175

Ser Ala Ser Gly Glu Leu Gly Asn Gly Asn Ile Lys Leu Ser Gln Thr
            180                 185                 190

Ser Asn Val Asp Lys Glu Glu Glu Ala Val Thr Ile Glu Met Asn Glu
        195                 200                 205

Pro Val Gln Leu Thr Phe Ala Leu Arg Tyr Leu Asn Phe Phe Thr Lys
        210                 215                 220

Ala Thr Pro Leu Ser Ser Thr Val Thr Leu Ser Met Ser Ala Asp Val
225                 230                 235                 240

Pro Leu Val Val Glu Tyr Lys Ile Ala Asp Met Gly His Leu Lys Tyr
                245                 250                 255

Tyr Leu Ala Pro Lys Ile Glu Asp Glu Glu Gly Ser
                260                 265

<210> SEQ ID NO 4
<211> LENGTH: 16
<212> TYPE: PRT
<213> ORGANISM: artificial sequence
<220> FEATURE:
<223> OTHER INFORMATION: FAM-POGO N-terminal modified peptide
<220> FEATURE:
<221> NAME/KEY: MOD_RES
<222> LOCATION: (1)..(1)

<400> SEQUENCE: 4

Ser Ala Val Leu Gln Lys Lys Ile Thr Asp Tyr Phe His Pro Lys Lys
1               5                   10                  15
```

INHIBITORS FOR PROLIFERATING CELL NUCLEAR ANTIGEN AND USES

CROSS REFERENCE

This present patent application is a continuation application of U.S. Utility patent application Ser. No. 15/781,742, filed Jun. 6, 2018, which is a national stage application under 35 U.S.C. § 371(c) of International Application No. PCT/US16/65062, filed on Dec. 6, 2016, which relates to and claims the priority under 35 U.S.C. § 119(e) to U.S. Provisional Patent Application Ser. No. 62/263,790 filed on Dec. 7, 2015, the content of which is hereby incorporated by reference in its entirety into the present disclosure.

GOVERNMENT SUPPORT CLAUSE

This invention was made with government support under CA023168 awarded by the National Institute of Health, and W81XWH-10-1-0105 awarded by the U.S. Army Medical Research and Materiel Command. The government has certain rights in the invention.

STATEMENT OF SEQUENCE LISTING

A computer-readable form (CRF) of the Sequence Listing is submitted with this application. The file, entitled 67362-03_Seq_Listing_ST25_txt, is generated on Mar. 6, 2020. Applicant states that the content of the computer-readable form is the same and the information recorded in computer readable form is identical to the written sequence listing.

TECHNICAL FIELD

The present disclosure generally relates to the design and discovery of therapeutics using peptidomimetic small molecules to map ideal surface binding interaction sites at a protein-protein interaction interface. Particularly, the present disclosure relates to inhibitors as a cancer treatment for Proliferating Cell Nuclear Antigen (PCNA, SEQ ID NO: 1) using computational-Based Multi-Fragment Peptoid Screening. Tripeptoids identified in this method are within the scope of this disclosure.

BACKGROUND

This section introduces aspects that may help facilitate a better understanding of the disclosure. Accordingly, these statements are to be read in this light and are not to be understood as admissions about what is or is not prior art.

Proliferating Cell Nuclear Antigen (PCNA, SEQ ID NO: 1) is a nuclear homotrimeric protein that encircles chromatin-bound DNA with attributes of a processivity factor in DNA damage repair and replication (Kelman, Z., et al. *Nucleic Acids Res.* 1995, 23 (18), 3613-3620; Pedley, A. M., et al. *PLoS ONE* 2014, 9 (7), e102481). It mediates protein complex formation in base excision, mismatch, nucleotide excision and translation synthesis DNA repair pathways (Maga, G., et al. *J. Cell Sci.* 2003, 116 (15), 3051-3060; Moldovan, G.-L., et al. *Cell* 2007, 129 (4), 665-679); Stoimenov, I., et al. *Biochem. Soc. Trans.* 2009, 37 (Pt 3), 605-613). PCNA also acts as a regulator of cell cycle progression, chromatin remodeling and transcription. More than 200 proteins are currently proposed to interact with PCNA implicating involvement in all facets of the DNA damage response (DDR) (Chatr-Aryamontri, A., et al. *Nucleic Acids Res.* 2015, 43 (Database issue), D470-D478).

Many of these proteins share a binding site on PCNA called the PCNA-Interacting Protein (PIP) box domain (Hishiki, A., et al. *J. Biol. Chem.* 2009, 284 (16), 10552-10560; Gulbis, J. M., et al. *Cell* 1996, 87 (2), 297-306; Bruning, J. B., et al. *Struct. Lond. Engl.* 1993 2004, 12 (12), 2209-2219). Antagonism of PCNA association with PIP box-containing proteins could ultimately impair the cell's ability to repair or replicate DNA. As evidence of this approach, the deletion of the PIP box within c-Abl disrupts increases the nuclear c-Abl apoptotic function in DNA-damaged cells (He, X., et al. *Apoptosis Int. J. Program. Cell Death* 2009, 14 (3), 268-275). While various strategies currently exist for targeting DNA repair pathways, functional antagonists of PCNA could serve uniquely to inhibit the DNA damage tolerance pathway, post-replication repair, specifically disrupting RAD6-dependent translesion synthesis as well as the "template switch" pathway (Lehmann, A. R., et al., *DNA Repair* 2006, 5 (12), 1495-1498; Hoege, C., et al. *Nature* 2002, 419 (6903), 135-141). The discovery of such an inhibitor would have potential as a sensitizing or synergistic agent in the development of new combination therapies.

SUMMARY

These and other features, aspects and advantages of the present invention will become better understood with reference to the following figures, associated descriptions and claims.

In some illustrative embodiments, this present invention is related to a compound having a general formula (I):

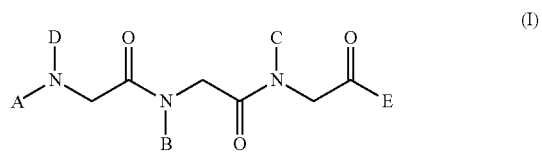

(I)

or a pharmaceutically acceptable salt, hydrate, solvate, polymorph, prodrug, solvate or clathrate thereof, wherein, independently, A is hydrogen, or —(CH)$R^1R^2$, wherein $R^1$ is hydrogen or —(CH$_2$)$_{0-3}$—OH, and $R^2$ is hydrogen, amino, guanidino, a $C_1$-$C_6$ alkylamino, a $C_1$-$C_6$ alkylguanidino, aminosulfone, a $C_1$-$C_6$ N-alkyl aminosulfone, a $C_1$-$C_{12}$ alkyl, a $C_1$-$C_{12}$ cycloalkyl, a $C_1$-$C_{12}$ heterocyclyl, a $C_1$-$C_{12}$ aryl, a $C_1$-$C_{12}$ substituted aryl, a $C_1$-$C_{12}$ heteroaryl, a $C_1$-$C_{12}$ substituted heteroaryl, a $C_1$-$C_{12}$ aralkyl, a $C_1$-$C_{12}$ substituted aralkyl, a $C_1$-$C_{12}$ heteroaralkyl, or a $C_1$-$C_{12}$ substituted heteroaralkyl;

B is hydrogen, a $C_1$-$C_{12}$ alkyl, a $C_1$-$C_{12}$ heteroalkyl, a $C_1$-$C_{12}$ cycloalkyl, a $C_1$-$C_{12}$ heterocyclyl, a $C_1$-$C_{12}$ aminoalkyl, a $C_1$-$C_{12}$ hydroxylalkyl, a $C_1$-$C_{12}$ mercaptoalkyl, aryl, a $C_1$-$C_{12}$ substituted aryl, a $C_1$-$C_{12}$ heteroaryl, a $C_1$-$C_{12}$ substituted heteroaryl, a $C_1$-$C_{12}$ aralkyl, a $C_1$-$C_{12}$ substituted aralkyl, a $C_1$-$C_{12}$ heteroaralkyl, or a $C_1$-$C_{12}$ substituted heteroaralkyl;

C is hydrogen, a $C_1$-$C_{12}$ alkyl, a $C_1$-$C_{12}$ heteroalkyl, a $C_1$-$C_{12}$ cycloalkyl, a $C_1$-$C_{12}$ heterocyclyl, a $C_1$-$C_{12}$ aminoalkyl, a $C_1$-$C_{12}$ hydroxylalkyl, a $C_1$-$C_{12}$ mercaptoalkyl, a $C_1$-$C_{12}$ aryl, a $C_1$-$C_{12}$ substituted aryl, a $C_1$-$C_{12}$ heteroaryl, a $C_1$-$C_{12}$ substituted heteroaryl, a $C_1$-$C_{12}$ aralkyl, a $C_1$-$C_{12}$ substituted aralkyl, a $C_1$-$C_{12}$ heteroaralkyl, or a $C_1$-$C_{12}$ substituted heteroaralkyl;

D is hydrogen, a $C_1$-$C_6$ alkyl, a $C_1$-$C_6$ heteroalkyl, a $C_1$-$C_6$ cycloalkyl, or a $C_1$-$C_6$ heterocyclyl; and E is hydrogen, amino, hydroxyl, $NR^3R^4$, or $OR^5$, wherein $R^3$, $R^4$, and $R^5$ are, independently, a $C_1$-$C_{12}$ alkyl, a $C_1$-$C_{12}$ cycloalkyl, a $C_1$-$C_{12}$ heterocyclyl, a $C_1$-$C_{12}$ aryl, a $C_1$-$C_{12}$ substituted aryl, a $C_1$-$C_{12}$ heteroaryl, a $C_1$-$C_{12}$ substituted heteroaryl, a $C_1$-$C_{12}$ aralkyl, a $C_1$-$C_{12}$ substituted aralkyl, a $C_1$-$C_{12}$ heteroaralkyl, or a $C_1$-$C_{12}$ substituted heteroaralkyl.

In some preferred embodiments, the present invention is related to a compound with a formula II, III, or IV:

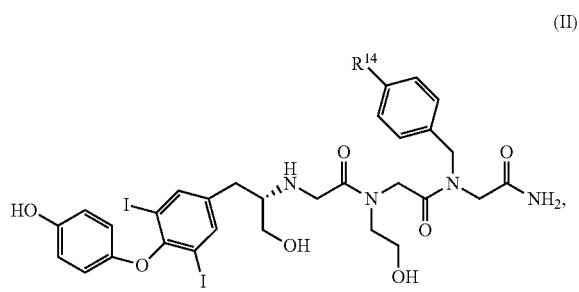

(II)

wherein $R^{14}$ is hydroxyl or aminomethyl;

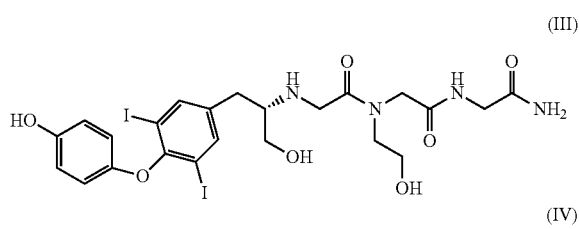

(III)

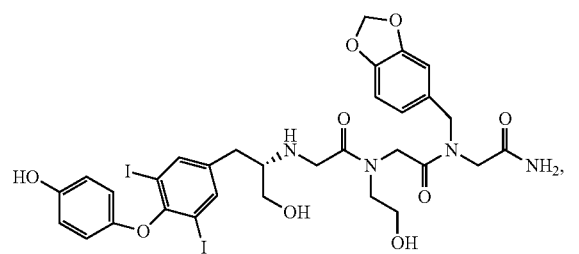

(IV)

or a pharmaceutically acceptable salt, hydrate, or solvate thereof.

In some other embodiments, this present invention is related to a pharmaceutical composition comprising one or more compounds disclosed herein, together with one or more pharmaceutically acceptable diluents, excipients, or carriers.

In another embodiment, this present invention is related to a pharmaceutical composition comprising one or more compounds disclosed herein, together with one or more other therapeutically effective compounds and pharmaceutically acceptable diluents, excipients, or carriers.

In another embodiment, this present invention is related to a pharmaceutical composition comprising a compound disclosed herein, and a therapeutically effective amount of one or more other compounds targeting CDK1, CDK4/6, EGFR, PARP1, IGF1-R, or FGFR pharmacological pathway, together with one or more therapeutically one or more pharmaceutically acceptable excipients.

In some embodiments, this present invention is related to a method for treating a patient with a cancer, the method comprising the step of administering a therapeutically effective amount of the compound disclosed herein to the patient in need of relief from said cancer.

In some embodiments, this present invention is related to a method for treating a patient with a prostate, lung, breast, or pancreatic cancer, the method comprising the step of administering a therapeutically effective amount of the compound disclosed herein to the patient in need of relief from said cancer.

In some embodiments, this present invention is related to a method for treating a patient with a cancer, the method comprising the step of administering a therapeutically effective amount of the compound disclosed herein, together with a therapeutically effective amount of a compound of the same or different mode of action, to the patient in need of relief from said cancer.

In some embodiments, this present invention is related to a method for treating a patient with a cancer, the method comprising the step of administering a therapeutically effective amount of the compound disclosed herein, together with a therapeutically effective amount of a compound targeting CDK1, CDK4/6, EGFR, PARP1, IGF1-R, or FGFR pharmacological pathway, to the patient in need of relief from said cancer.

In some embodiments, this present invention is related to a method for treating a patient with a prostate, lung, breast, or pancreatic cancer, the method comprising the step of administering a therapeutically effective amount of the compound disclosed herein, together with a therapeutically effective amount of a compound targeting CDK1, CDK4/6, EGFR, PARP1, IGF1-R, or FGFR pharmacological pathway, to the patient in need of relief from said cancer.

DETAILED DESCRIPTION

Figure 1:
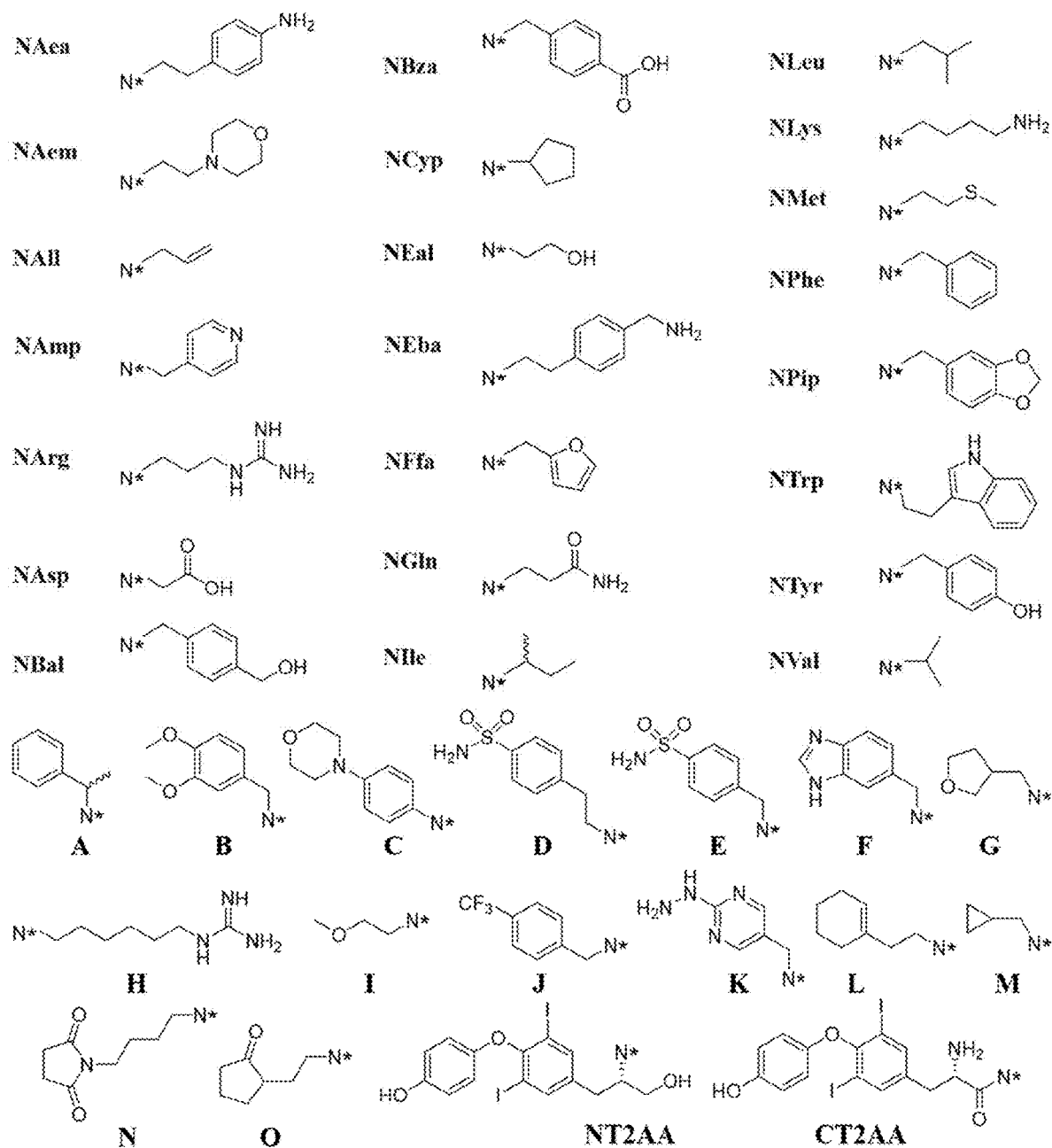
FIG. 1 shows the fragments used for the creation of virtual tripeptoid libraries. A list of 37 primary amines, along with T2AA, was used to create a combinatorial virtual library of peptoid-based compounds. N* indicates the location of the —$NH_2$ group, which is the position of substitution into the tripeptoid backbone. Blue labels indicate fragments that were used in the initial screen of tripeptoids containing a combinatorial set of 20 primary amines.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Those skilled in the art will recognize that numerous modifications can be made to the specific implementations described above. The implementations should not be limited to the particular limitations described. Other implementations may be possible.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. In the present disclosure the term "about" can allow for a degree of variability in a value or range, for example, within 10%, within 5%, or within 1% of a stated value or of a stated limit of a range. In the present disclosure the term "substantially" can allow for a degree of variability in a value or range, for example, within 60%, within 80%, within 90%, within 95%, or within 99% or more of a stated value or of a stated limit of a range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

The term "organic group" as used herein refers to but is not limited to any carbon-containing functional group. For example, an oxygen-containing group such as an alkoxy group, aryloxy group, aralkyloxy group, oxo(carbonyl) group, a carboxyl group including a carboxylic acid, carboxylate, and a carboxylate ester; a sulfur-containing group such as an alkyl and aryl sulfide group; and other heteroatom-containing groups.

The term "substituted" as used herein refers to an organic group as defined herein or molecule in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, $C_1$, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups.

The term "alkyl" as used herein refers to substituted or unsubstituted straight chain and branched alkyl groups and cycloalkyl groups having from 1 to 40 carbon atoms ($C_1$-$C_{40}$), 1 to about 20 carbon atoms ($C_1$-$C_{20}$), 1 to 12 carbons ($C_1$-$C_{12}$), 1 to 8 carbon atoms ($C_1$-$C_8$), or, in some embodiments, from 1 to 6 carbon atoms ($C_1$-$C_6$). Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to substituted or unsubstituted straight chain and branched divalent alkenyl and cycloalkenyl groups having from 2 to 20 carbon atoms ($C_2$-$C_{20}$), 2 to 12 carbons ($C_2$-$C_{12}$), 2 to 8 carbon atoms ($C_2$-$C_8$) or, in some embodiments, from 2 to 4 carbon atoms ($C_2$-$C_4$) and at least one carbon-carbon double bond. Examples of straight chain alkenyl groups include those with from 2 to 8 carbon atoms such as —CH=CH—, —CH=CHCH$_2$—, and the like. Examples of branched alkenyl groups include, but are not limited to, —CH=C (CH$_3$)— and the like.

The term "alkylene" as used herein refers to substituted or unsubstituted straight chain and branched divalent alkylene groups and cycloalkylene groups having from 1 to 40 carbon atoms ($C_1$-$C_{40}$), 1 to about 20 carbon atoms ($C_1$-$C_{20}$), 1 to 12 carbons ($C_1$-$C_{12}$), 1 to 8 carbon atoms ($C_1$-$C_8$) or, in some embodiments, from 1 to 4 carbon atoms ($C_1$-$C_4$), from 1 to 5 carbon atoms ($C_1$-$C_5$), from 2 to 5 carbon atoms ($C_2$-$C_5$) or from 3 to 4 carbon atoms ($C_3$-$C_4$). Examples of straight chain alkylene groups include those with from 1 to 8 carbon atoms such as methylene (—CH$_2$—), ethylene (—CH$_2$CH$_2$—), n-propylene (—CH$_2$CH$_2$CH$_2$—), n-butylene (—CH$_2$(CH$_2$)$_2$CH$_2$—) and the like. Examples of branched alkylene groups include, but are not limited to, isopropylidene (CH$_2$CH(CH$_3$)) and the like. Examples of cycloalkylene groups include, but are not limited to, cyclopropylidene, cyclobutylidene, cyclopentylidene and the like.

The term "hydroxyalkyl" as used herein refers to alkyl groups as defined herein substituted with at least one hydroxyl (—OH) group.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. In some embodiments, cycloalkyl groups can have 3 to 6 carbon atoms ($C_3$-$C_6$). Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "heterocyclylcarbonyl" is an example of an acyl group that is bonded to a substituted or unsubstituted heterocyclyl group, as the term "heterocyclyl" is defined herein. An example of a heterocyclylcarbonyl group is a prolyl group, wherein the prolyl group can be a D- or an L-prolyl group.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to substituted or unsubstituted aromatic and non-aromatic ring compounds containing 3 or more ring members, of which, one or more is a heteroatom such as, but not limited to, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms ($C_3$-$C_8$), 3 to 6 carbon atoms ($C_3$-$C_6$) or 6 to 8 carbon atoms ($C_6$-$C_8$). A heterocyclyl group designated as a $C_2$-heterocyclyl can be a 5-ring with two carbon atoms and three heteroatoms, a 6-ring with two carbon atoms and four heteroatoms and so forth. Likewise a $C_4$-heterocyclyl can be a 5-ring with one heteroatom, a 6-ring with two heteroatoms, and so forth. The number of carbon atoms plus the number of heteroatoms equals the total number of ring atoms. A heterocyclyl ring can also include one or more double bonds. A heteroaryl ring is an embodiment of a heterocyclyl group. The phrase "heterocyclyl group" includes fused ring species including those that include fused aromatic and non-aromatic groups. Representative heterocyclyl groups include, but are not limited to pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, and benzimidazolinyl groups.

The term "heteroarylalkyl" as used herein refers to alkyl groups as defined herein in which a hydrogen or carbon bond of an alkyl group is replaced with a bond to a heteroaryl group as defined herein.

The term "amine" as used herein refers to primary, secondary, and tertiary amines. Amines include but are not limited to R—$NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —$NH_2$, —NHR, —$NR_2$, —$NR_3^+$, wherein each R is independently selected, and protonated forms of each, except for —$NR_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, perfluorobutyl, —$CF(CH_3)_2$ and the like.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention.

Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

Various embodiments of the present invention also contemplate pharmaceutical compositions comprising one or more compounds of the various embodiments of the present invention and one or more pharmaceutically acceptable carriers, diluents, excipients or combinations thereof. A "pharmaceutical composition" refers to a chemical or biological composition suitable for administration to a subject (e.g., mammal). Such compositions may be specifically formulated for administration via one or more of a number of routes, including but not limited to buccal, cutaneous, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. In addition, administration can by means of capsule, drops, foams, gel, gum, injection, liquid, patch, pill, porous pouch, powder, tablet, or other suitable means of administration.

A "pharmaceutical excipient" or a "pharmaceutically acceptable excipient" comprises a carrier, sometimes a liquid, in which an active therapeutic agent is formulated. The excipient generally does not provide any pharmacological activity to the formulation, though it may provide chemical and/or biological stability, and release characteristics. Examples of suitable formulations can be found, for example, in Remington, The Science And Practice of Pharmacy, 20th Edition, (Gennaro, A. R., Chief Editor), Philadelphia College of Pharmacy and Science, 2000, which is incorporated by reference in its entirety.

As used herein "pharmaceutically acceptable carrier" or "excipient" includes any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, sublingual, or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions may be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (e.g., glycerol, propylene glycol, and liquid polyethylene glycol), and suitable mixtures thereof. The proper fluidity can be maintained, for example, by the use of a coating such as lecithin, by the maintenance of the required particle size in the case of dispersion and by the use of surfactants.

In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the compounds described herein can be formulated in a time release formulation, for example in a composition that includes a slow release polymer. The active compounds can be prepared with carriers that will protect the compound against rapid release, such as a controlled release formulation, including implants and microencapsulated delivery systems. Biodegradable, biocompatible polymers may be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

Oral forms of administration are also contemplated herein. The pharmaceutical compositions of the present invention may be orally administered as a capsule (hard or soft), tablet (film coated, enteric coated or uncoated), powder or granules (coated or uncoated) or liquid (solution or suspension). The formulations may be conveniently prepared by any of the methods well-known in the art. The pharmaceutical compositions of the present invention may include one or more suitable production aids or excipients including fillers, binders, disintegrants, lubricants, diluents, flow agents, buffering agents, moistening agents, preservatives, colorants, sweeteners, flavors, and pharmaceutically compatible carriers.

For each of the recited embodiments, the compounds can be administered by a variety of dosage forms as known in the art. Any biologically-acceptable dosage form known to persons of ordinary skill in the art, and combinations thereof, are contemplated. Examples of such dosage forms include, without limitation, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, lozenges, chewable lozenges, beads, powders, gum, granules, particles, microparticles, dispersible granules, cachets, douches, suppositories, creams, topicals, inhalants, aerosol inhalants, patches, particle inhalants, implants, depot implants, ingestibles, injectables (including subcutaneous, intramuscular, intravenous, and intradermal), infusions, and combinations thereof.

Other compounds which can be included by admixture are, for example, medically inert ingredients (e.g., solid and liquid diluent), such as lactose, dextrosesaccharose, cellulose, starch or calcium phosphate for tablets or capsules, olive oil or ethyl oleate for soft capsules and water or vegetable oil for suspensions or emulsions; lubricating agents such as silica, talc, stearic acid, magnesium or calcium stearate and/or polyethylene glycols; gelling agents such as colloidal clays; thickening agents such as gum tragacanth or sodium alginate, binding agents such as starches, arabic gums, gelatin, methylcellulose, carboxymethylcellulose or polyvinylpyrrolidone; disintegrating agents such as starch, alginic acid, alginates or sodium starch glycolate; effervescing mixtures; dyestuff; sweeteners; wetting agents such as lecithin, polysorbates or laurylsulphates; and other therapeutically acceptable accessory ingredients, such as humectants, preservatives, buffers and antioxidants, which are known additives for such formulations.

Liquid dispersions for oral administration can be syrups, emulsions, solutions, or suspensions. The syrups can contain as a carrier, for example, saccharose or saccharose with glycerol and/or mannitol and/or sorbitol. The suspensions and the emulsions can contain a carrier, for example a natural gum, agar, sodium alginate, pectin, methylcellulose, carboxymethylcellulose, or polyvinyl alcohol.

The amount of active compound in a therapeutic composition according to various embodiments of the present invention may vary according to factors such as the disease state, age, gender, weight, patient history, risk factors, predisposition to disease, administration route, pre-existing treatment regime (e.g., possible interactions with other medications), and weight of the individual. Dosage regimens may be adjusted to provide the optimum therapeutic response. For example, a single bolus may be administered, several divided doses may be administered over time, or the dose may be proportionally reduced or increased as indicated by the exigencies of therapeutic situation.

"Dosage unit form," as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals. In therapeutic use for treatment of conditions in mammals (e.g., humans) for which the compounds of the present invention or an appropriate pharmaceutical composition thereof are effective, the compounds of the present invention may be administered in an effective amount. The dosages as suitable for this invention may be a composition, a pharmaceutical composition or any other compositions described herein.

For each of the recited embodiments, the dosage is typically administered once, twice, or thrice a day, although more frequent dosing intervals are possible. The dosage may be administered every day, every 2 days, every 3 days, every 4 days, every 5 days, every 6 days, and/or every 7 days (once a week). In one embodiment, the dosage may be administered daily for up to and including 30 days, preferably between 7-10 days. In another embodiment, the dosage may be administered twice a day for 10 days. If the patient requires treatment for a chronic disease or condition, the dosage may be administered for as long as signs and/or symptoms persist. The patient may require "maintenance treatment" where the patient is receiving dosages every day for months, years, or the remainder of their lives. In addition, the composition of this invention may be to effect prophylaxis of recurring symptoms. For example, the dosage may be administered once or twice a day to prevent the onset of symptoms in patients at risk, especially for asymptomatic patients.

The compositions described herein may be administered in any of the following routes: buccal, epicutaneous, epidural, infusion, inhalation, intraarterial, intracardial, intracerebroventricular, intradermal, intramuscular, intranasal, intraocular, intraperitoneal, intraspinal, intrathecal, intravenous, oral, parenteral, pulmonary, rectally via an enema or suppository, subcutaneous, subdermal, sublingual, transdermal, and transmucosal. The preferred routes of administration are buccal and oral. The administration can be local, where the composition is administered directly, close to, in the locality, near, at, about, or in the vicinity of, the site(s) of disease, e.g., inflammation, or systemic, wherein the composition is given to the patient and passes through the body widely, thereby reaching the site(s) of disease. Local administration can be administration to the cell, tissue, organ, and/or organ system, which encompasses and/or is affected by the disease, and/or where the disease signs and/or symptoms are active or are likely to occur. Administration can be topical with a local effect, composition is applied directly where its action is desired. Administration can be enteral wherein the desired effect is systemic (non-local), composition is given via the digestive tract. Administration can be parenteral, where the desired effect is systemic, composition is given by other routes than the digestive tract.

In some embodiments, the present invention contemplates compositions comprising a therapeutically effective amount of one or more compounds of the various embodiments of the present invention. In some embodiments, the compositions are useful in a method for treating cancer, the method comprising administering a therapeutically effective amount of one or more compounds of any claim to a patient in need thereof. In some aspects, the various embodiments of the present invention contemplate a compound of the formula (I) (II) and (III) for use as a medicament for treating a patient in need of relief from cancers, including, but not limited to, prostate cancer, lung cancer, breast cancer, or pancreatic cancer.

In some other embodiments, the present invention contemplates compositions comprising a therapeutically effective amount of a compound of the present invention, together with a therapeutically effective amount of one or more other compounds of the same or different mode of action to a patient in need of relief from said cancer.

The term "therapeutically effective amount" as used herein, refers to that amount of one or more compounds of the various embodiments of the present invention that elicits a biological or medicinal response in a tissue system, animal or human, that is being sought by a researcher, veterinarian, medical doctor or other clinician, which includes alleviation of the symptoms of the disease or disorder being treated. In some embodiments, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the condition being treated and the severity of the condition; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician. It is also appreciated that the therapeutically effective amount can be selected with reference to any toxicity, or other undesirable side effect, that might occur during administration of one or more of the compounds described herein.

Cancer is a disease of genomic instability, which is caused by mutations in genes that are associated with cellular proliferation and survival (Stoimenov & Helleday, *Biochem. Soc. Trans.* 37, 605 (2009)). The proliferating cellular nuclear antigen (PCNA) is a homotrimeric scaffold protein that forms a ring around DNA and interacts with more than 200 other proteins that regulate and effect DNA replication, chromatin remodeling, telomere maintenance, and DNA damage repair (Maga, G. *J. Cell Sci.* 116, 3051-3060 (2003)). PCNA is so instrumental in both DNA damage repair and DNA replication processes due to PCNA's association with DNA polymerases (Bruning & Shamoo, *Structure* 12, 2209-2219 (2004)). Without PCNA, DNA polymerases of all different types would be unable to associate with damaged DNA sites or DNA replication sites. Long-patch base excision repair (BER), homologous recombination (HR), and mismatch repair (MMR) all require PCNA to be able to finish their repair of single-strand breaks, double strand breaks, and mismatched nucleotides respectively (Matsumoto, Y. in *Base Excision Repair* Volume 68, 129-138 (Academic Press, 2001); Moldovan, G.-L. et al., *Mol. Cell* 45, 75-86 (2012); Dieckman, L. M., et al., *Biochemistry* (Mosc.) 52, (2013)). With the loss of these three processes, but more importantly, DNA replication, loss of PCNA is embryonically lethal, making PCNA an essential gene. While PCNA is overexpressed in every cell that is proliferating, almost all tumor cells, it does not make an attractive target as a monotherapy, but would require specific pairings that can be specifically enhanced through the loss of a PCNA-dependent process (Bozza, W. P., et al., *Anal Biochem* 427, 69-78 (2012)).

Epidermal growth factor receptor (EGFR) is a well-known cancer therapeutic target as it is involved in multiple pathways promoting cellular proliferation, cell survival, and DNA damage repair (Ciardiello & Tortora, *Eur. J. Cancer Oxf. Engl.* 1990, 39, 1348-1354 (2003)). Pathways regulated by EGFR include the MAPK and AKT pathways as regulation of DNA-PK and non-homologous end joining (NHEJ), one of two major double-strand break repair (Han & Lo, *Cancer Lett.* 318, 124-134 (2012)). Drugs including erlotinib, gefitinib, and lapatinib all target EGFR to great effect in multiple cancer types. An important role of EGFR is its capacity to phosphorylate PCNA at the Y211 residue (Yu, Y.-L. et al., *PLoS ONE* 8, e61362 (2013)). This is required to stabilize PCNA and prevent proteasomal degradation. Without this stabilization, PCNA is unable to reach levels required to begin DNA replication and is required for fully active homologous recombination, the second major double-strand break repair pathway (Gu, L. et al., *PLoS ONE* 9, e94773 (2014)). Through inhibition of PCNA interaction with its interactors as well as general EGFR antagonism would sensitize tumors especially towards double-strand breaks, the most lethal of DNA damage. This could be effective in treating patients with a fully functional HR pathway in lung, breast, or prostate cancer.

Fibroblast growth factor receptor (FGFR) and insulin-like growth factor receptor (IGFR) both are involved in similar pathways to EGFR, MAPK and AKT pathways (Schayek, H. et al., *Clin. Cancer Res. Off. J. Am. Assoc. Cancer Res.* 15, 1558-1565 (2009); Chioni & Grose, *J. Cell Biol.* 197, 801-817 (2012)). These two receptors have been shown to compensate for EGFR loss resulting in resistance to EGFR antagonists (Turner, N. C. et al. *N. Engl. J. Med.* 373, 209-219 (2015); Dean, J. L., et al., *J. Biol. Chem.* 287, 29075-29087 (2012)). A large difference between these two receptors and EGFR is that there is no proven direct interaction with PCNA as there is with EGFR. Tumors addicted to IGFR or FGFR could see synergism between an antagonist to the respective receptor with a PCNA antagonist. This combination would allow for continued sensitization tumors to double-strand breaks in the presence of other tyrosine receptor kinase inhibitors. This would be relevant in prostate cancer tumors that are dependent on IGFR and breast or lung cancer tumors that are dependent on FGFR.

Cyclin-dependent kinases (CDK) regulate cell cycle progression through specific checkpoints that mark the completion of important phases of cell growth. An important step in the mitosis of any cell is the duplication of the genomic material in the S phase. While CDK1 is needed to initialize this phase, CDK4/6 are needed to regulate the progression through and finishing S phase. Inhibition of CDKs are generally toxic to all proliferating cells, which typically relegates their use to late stage cancers that have already metastasized (Turner, N. C. et al., *N. Engl. J. Med.* 373, 209-219 (2015)). However, HR requires that sister chromatids be available for interstrand invasion necessary for HR to be template-derived. This can only effectively occur during S phase, which requires that key regulators of HR to be modified by CDK1 and CDK4/6 (Dean, J. L., et al., *J. Biol. Chem.* 287, 29075-29087 (2012)). Many tumors possess phenotypes that naturally lead to more damage, such as metabolism that leads to more ROS or oxidative agents through favoring anoxic glucose metabolism or increased levels of topoisomerases (Liou & Storz, *Free Radic. Res.* 44, (2010); Panieri & Santoro, *Cell Death Dis.* 7, e2253 (2016)). These can cause multiple DNA damage types including single-strand breaks and double-strand breaks whose repair pathways require PCNA. PCNA is also require for DNA replication which has to occur for transition out of S phase to not result in cell death. In this way PCNA and CDK 1/4/6 could provide an effective combination not just over highly proliferating cells, but those that over express CDK1, 4, or 6. These are commonly observed in breast, lung, and prostate cancer.

Poly (ADP-ribose) polymerase 1 (PARP1) is an important detector of DNA damage as well as a regulator of NHEJ (Beck, C., et al., *Exp. Cell Res.* 329, 18-25 (2014)). Olaparib, a PARP1 inhibitor, has been shown to be highly effective in patients that possess a BRCA1 loss-of-function mutation or any other loss-of-function mutation that severely hampers HR function (Kaufman, B. et al., *J. Clin. Oncol.* 33, 244-250 (2015)). This is a classic case of synthetic lethality where the loss of both DSB pathways is lethal, but if either remains, the cell is still viable. Olaparib has been shown to be very ineffective in patients that possess a functional HR pathway (Peng, G. et al., *Nat. Commun.* 5, 3361 (2014)). PCNA's interaction with DNA polymerase in the late phases of the HR pathway are absolutely critical (Armstrong, H. K. et al., *Prostate* 76(16):1546-1559(2016)). Further, PCNA is not directly involved with HR regulation allowing HR to be selected, but, overall, ineffective. Utilizing a PCNA antagonist to render the HR pathway ineffective, yet maintain a bias for that pathway. This would sensitize the tumor to Olaparib, but normal tissue would be far less damaged as they can favor NHEJ over HR preventing high levels of toxicity.

Due to PCNA's role in several DNA damage repair pathways as well as DNA replication, the loss of PCNA would lead to a significant increase in DNA damage (Armstrong, H. K. et al., 2016). This might allow for a PCNA antagonist to effectively replace a direct DNA damaging agent such as cisplatin or doxorubicin which damage all cells, not merely highly proliferating cells. Used in combination with a number of antagonists, including those that target EGFR or PARP1, could reduce toxicity compared to combinations that include cisplatin or doxorubicin. PCNA antagonists may also be used as an alternative to direct DNA damaging agents in combinations with drugs that target highly replicating cells such as gemcitabine.

While a rationale for proliferating cell nuclear antigen (PCNA) as a disease target has emerged, the nature of PCNA-protein interactions does not provide a traditional drug target and motivates a new approach to modulate protein-protein interactions (PPIs). Structure-based design of PCNA antagonists could benefit from PIP box-containing peptides/proteins in complex with PCNA. However, this information to date has revealed that the core PIP box recognition sequence is involved in a $3_{10}$-helix that binds in a hydrophobic surface pocket on PCNA. Small molecule mimics of this topology are not easily defined. Our previous studies of PCNA features responsible for specificity of protein recruitment using PIP box peptides implicate varied conformations of PCNA upon ligand engagement that could impart functional differences (Pedley, A. M., et al. *PLoS ONE* 2014, 9 (7), e102481). Finally, a recent high-throughput biomolecular screening effort led to the discovery of the thyroxine class of antagonists that target the surface pocket that the PIP box's $3_{10}$-helix binds in. And One of these compounds showed useful pharmacologic effects when used in combination with a DNA damaging agent (Punchihewa, C., et al. *J. Biol. Chem.* 2012, 287(17):14289-300; Actis, M., et al. *Bioorg. Med. Chem.* 2013, 21(7):1972-7).

Fragment-based drug design (FBDD) is a generalized approach commonly used for the discovery of ligands that bind with suitable affinity for the desired biological targets (Erlanson, D. A. *Top. Curr. Chem.* 2012, 317, 1-32). By screening low molecular weight chemical fragments, which individually bind to their intended target sites, higher affinity drug-like molecules can be generated using the combined information. FBDD can have inherent advantages over screening higher molecular weight libraries when factors such as commercial availability, ease of synthesis and coverage of chemical space are considered (Erlanson, D. A., et al., *J. Med. Chem.* 2004, 47 (14), 3463-3482). Furthermore, libraries consisting of larger molecular weight entities can be disadvantaged by their "bulkiness", which may preclude favorable binding ligand interactions in protein subpockets due to steric exclusion (Bartolowits and Davisson, *Chem. Biol. Drug Des.* 2016, 87(1), 5-20). Screening single small fragments is useful in situations where 3D structural information of a target site is readily available. However, the methods and approaches in fragment based screens have demonstrated variable outcomes with similar targets (Wielens, J., et al., *J. Biomol. Screen.* 2013, 18 (2), 147-159). Also, new and refined approaches that utilize the concepts of fragment-based screens offer increased applications to a broader range of protein targets.

A challenge for application of FBDD methods for protein-protein interactions is the conformational flexibility of the protein docking sites even in cases where localized 'hot spots' are defined (Wells, J. A., et al. *Nature* 2007,450 (7172), 1001-1009; Jubb, H., et al. *Prog. Biophys. Mol. Biol.* 2015,119 (1), 2-9). A molecular screening system that rapidly maps surfaces and multiple subpocket binding sites, in tandem, would provide advantages for defining new probe ligands (Bartolowits and Davisson, *Chem. Biol. Drug Des.* 2016, 87(1), 5-20). Such an approach would offer opportunities to define hit molecules with multiple molecular features pre-filtered to be considered for optimization of drug-like properties. Peptoids offer a chemical scaffold with conformational flexibility and potential for high degrees of fragment diversity. Traditional biomolecular screens using peptoid libraries have proven useful in identifying ligands for many types of protein targets. Several of these efforts make use of trimeric peptoid libraries, which are generally small enough to be considered small molecules. A key attribute of these molecular-types is that they effectively "tie" three chemical fragments together into a single backbone, enabling tandem multi-fragment screening. However, depending on target systems, it may not be efficient to construct large and diverse screening libraries of trimeric molecules. As a result, a method to reduce the number of compounds while maximizing the diversity of fragment features prior to a focused set of scalable syntheses is desired.

As an alternative to traditional FBDD methodology, this study demonstrated that multiple individual fragments could be linked in a single peptoid-based backbone for in silico screening, followed by synthesis and in vitro testing to discover inhibitors of PCNA-PIP box interactions. Though much attention in the field of drug discovery is being paid to developing new inhibitors of protein-protein interactions, PCNA itself is not necessarily considered an easy drug target. PCNA does not have a natural small molecule binding site, nor does it have any visible deep binding clefts that would make targeting that site with a ligand obvious. Even when compared to other protein-protein interfaces, such as the contact surface between MDM2 and p53, there is not a clear binding groove—instead there is a shallow, relatively small surface pocket where only a couple amino acids bind from PIP box-containing proteins. However, other studies have been able to identify small molecules that are able to bind at that site with enough affinity to disrupt the binding between PCNA and a PIP box-containing peptide (Punchihewa, C., et al. *J. Biol. Chem.* 2012, 287(17):14289-300; Actis, M., et al. *Bioorg. Med. Chem.* 2013, 21(7):1972-7). The next step in developing high affinity ligands for PCNA would be to expand upon the chemical information gained from the tripeptoids that showed up as hits in experimental screens, to create next generation ligands that take advantage of the molecular contacts identified in the molecular dynamic simulations. Interestingly, the classification analysis of peptoids that were experimental hits predicted almost all of them to be iPPIs, while the majority of non-hits were predicted to be non-iPPIs. It is possible that this could be used in the future as an additional computational filter based on whether a compound is predicted to be an iPPI, and this could further narrow the list of compounds to be synthesized once favorable side chains are identified.

This applied approach has the potential to be applied to numerous protein targets where an ideal ligand would need a higher degree of globularity and would have to cover a relatively large surface area. Although this method offers some potential versatility in screening against different proteins, it must be acknowledged that there are some natural drawbacks to the ligands. Due to the nature of the peptoid backbone, and the way in which these compounds are cleaved from resin, there are amine and carbonyl groups that are necessarily present, which may result in unfavorable interactions with the target binding site, depending on the orientation of the ligand. Additionally, and perhaps most significantly, because the individual peptoid side chains are tied together into a single backbone, their degrees of freedom are substantially restricted, and this can mean that an individual fragment may not be able to orient itself in the proper way to fully optimize a binding interaction. Furthermore, because the entire library here consisted of peptoid trimers, a particular ligand may maintain favorable interactions between only two of its side chains and the protein; forcing the presence of the third side chain may curtail the overall binding affinity of the total ligand if the individual interaction between that third fragment and the protein is unfavorable. There potentially are also situations where to disrupt a particular protein-protein interaction, three peptoid residues would be insufficient—four or more may be needed. These are all common dilemmas that are faced with FBDD and/or drug screening efforts in that one must always be concerned with the chemical content and diversity of the compounds in the screening library. In that regard, this approach is not unusual, but it does place limits on how it can be used.

Tripeptoid Library Creation Using Computational Tools. The PIP-box binding site on PCNA was examined in an effort to gain basic information on favorable chemical features of potential small molecule inhibitors. Our previous work has identified three key regions at the PIP box binding site that are important for the recognition and binding of PIP box-containing peptides/proteins (Pedley, A. M., et al. *PLoS ONE* 2014, 9 (7), e102481). It was predicted that tripeptoids would be sufficient in size to engage each of these key areas. The general mass range of such materials are close to those for other known inhibitors of PPIs (for example: Zhao, et al. *J. Med. Chem.* 2015, 58 (3), 1038-1052), and the size of these ligands also enhances synthetic accessibility, time to completion, and cost efficiency. An initial set of 20 primary amines was selected (FIG. 1) that varied in their hydrophobicity, aromaticity, ability to form hydrogen bonds, and contained substructures present in clinically available drugs. Many of the amines from this set are commercially available, though some require different degrees of in-house synthesis. The CombiGLIDE application within Maestro (Schrödinger Release 2013-2: Maestro, Version 9.5, Schrödinger, LLC, New York, N.Y., 2013) was used to generate a virtual library of trimeric peptoids that contained each of the 20 primary amines, plus hydrogen as a potential substituent, in a combinatorial fashion to give 9,261 total compounds. The ligands were ionized (along with desalting and tautomeric generation) using Epik to generate all possible states within a pH range of 7.0±2.0, and these were minimized using the OPLS-2005 force field.

In general, using a single rigid protein structure for virtual docking tends to produce skewed results due to geometric constraints and functional group directionality at the binding site. This is exacerbated when taking into account a protein such as PCNA, which has a significant degree of plasticity at the PIP box site (Pedley, A. M., et al. *PLoS ONE* 2014, 9 (7), e102481), since there are likely to be many false negatives when docking rigidly. While a flexible docking method such as Schrödinger Maestro's induced-fit (Small-Molecule Drug Discovery Suite 2013-3: Schrödinger Suite 2013-3 Induced Fit Docking Protocol; Glide Version 6.1, Schrödinger, LLC, New York, N.Y., 2013; Prime Version 3.4, Schrödinger, LLC, New York, N.Y., 2013; New York, N.Y., 2013) is more ideally suited for screening ligands virtually, the computational time required for such a method makes it impractical for screening more than several ligands at a time, especially those with high degrees of freedom such as linear peptides and peptoids. To partially compensate, four crystal structures of PCNA bound to four different ligands were selected for screening, each being structurally divergent at the PIP box binding site. These structures included PCNA complexed to the C-terminal tail of p21 (PDB ID: 1AXC), PCNA complexed to residues 331-350 of FEN1 (PDB ID: 1U7B), PCNA complexed with the T3 ligand (PDB ID: 3VKX) and PCNA complexed with a fragment of DNA polymerase η (PDB ID: 2ZVK).

Each crystal structure of PCNA was prepared using the Protein Preparation Wizard in Maestro. Each protein was minimized in complex with its respective ligand/peptide using the OPLS-2005 force field. Cubic grid boxes were created using either T3 (3VKX), or a PIP box peptide amino acid at the hydrophobic site on PCNA, as the centroid, with a length of 30 Å. The prepared ligands were flexibly docked into each form of PCNA using the standard precision (SP) model in Glide (Small-Molecule Drug Discovery Suite 2013-2: Glide, Version 6.0, Schrödinger, LLC, New York, N.Y., 2013) and the top 10% of the ligand hits from each docking run were flexibly re-docked into the respective form of PCNA using the extra precision (XP) Glide algorithm, which places harsher penalties on desolvation energy and ligand strain, and has greater requirements for ligand-receptor shape complementarity. Upon completion of each docking exercise, the top 50 hits in each of the docking runs were analyzed. The frequency with which a specific fragment was present at a particular location along the tripeptoid backbone was tallied for each crystal structure of PCNA, and the top 50 hits from each run were compiled into a total list of 200 top hits.

Figure 2:
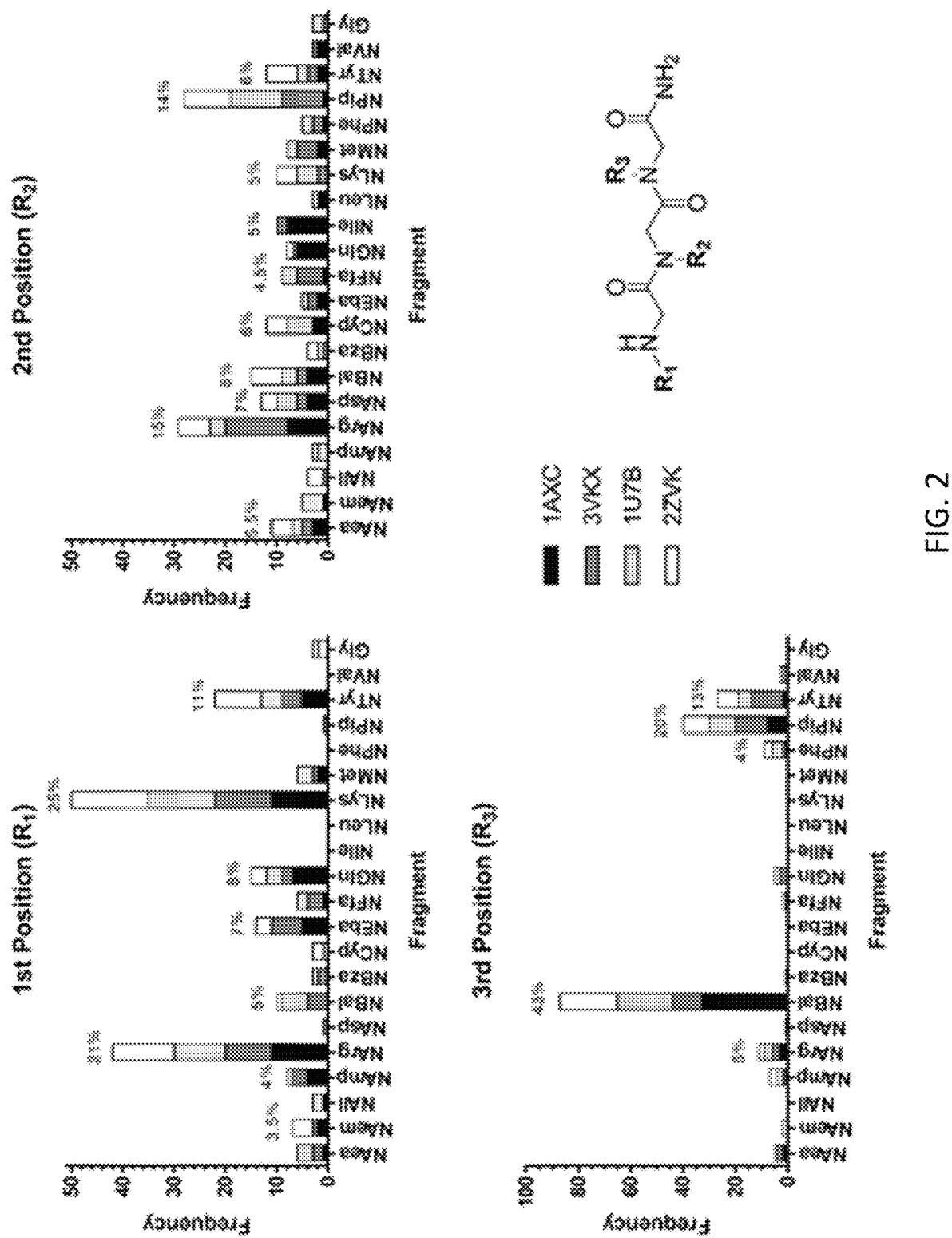
FIG. 2 is a glide docking-based frequency with which fragments appeared in the three substitution positions on a tripeptoid backbone. A set of 20 fragments, in addition to hydrogen, were virtually combinatorially incorporated into a tripeptoid backbone, and were screened against four different crystal structures of PCNA (PDB IDs: 1AXC, 3VKX, 1U7B and 2ZVK) in silico using the Glide SP and XP docking algorithms. The frequency that respective fragments appeared in positions $R_1$, $R_2$ or $R_3$ (lower right) were tallied for the top 50 hits from each run involving a different crystal structure. The percentage of the cumulative total of substitution frequency (out of a possible 200) at a given position is shown above the stacked columns. Hydrogen as a substituent is labeled as "Gly".

As expected, different screening results were observed for each crystal structure of PCNA, and different results were seen for each substitution position along the peptoid backbone (FIG. 2). The $1^{st}$ (N-terminal) position generally showed a relatively limited preference for a set of several peptoid side chains including NLys, NArg, NTyr, NGln, NEba and NBal. Two fragments that stood out most significantly were NLys and NArg, each of which were present in over 20% of the top hit list. The $2^{nd}$ position did not show strong preference for a limited number of fragments—rather, nine different fragments were present in the $2^{nd}$ position in at least 5% of the top hit list, though NArg and NPip did stand out with them being present in 15% and 14% of the top hits, respectively. In contrast to the first two positions, the $3^{rd}$ position in the peptoid backbone showed significant preference for particular side chains, notably aromatic groups that contained functionalities that allow for hydrogen bonding with protein amino acids. NBal especially stood out as 43% of all of the top hit compounds contained that fragment in the $3^{rd}$ position.

In previous studies, the small molecules T3 (triiodothyronine) and T2AA ((S)-4-(4-(2-amino-3-hydroxypropyl)-2, 6-diiodophenoxy)phenol), as well as several synthetic variants, have been demonstrated to bind in a hydrophobic subpocket of the PIP box binding site (Punchihewa, C., et al. *J. Biol. Chem.* 2012, 287(17):14289-300; Actis, M., et al. *Bioorg. Med. Chem.* 2013, 21(7):1972-7). Both compounds were considered as monomers to expand the diversity of primary amines (FIG. 1). Each were envisioned to be compatible with either submonomer peptoid synthesis or basic conditions for solid phase peptide synthesis. In doing so, either could potentially serve as an anchor fragment, directing small peptoid fragment to additional subpockets in the PIP box binding site on PCNA. T2AA was selected as a better candidate for investigation based upon physicochemical properties and the lack of thyroid hormone properties. A virtual combinatorial library was created using the same methodology as previously discussed, with a set of 37 peptoid side chains including NT2AA and CT2AA, which differ in attachment points (FIG. 1). This library was screened against the crystal structure of PCNA bound to the T3 ligand (PDB ID: 3VKX). Significant conformational differences in the PIP box binding site between the co-crystal structures of PCNA-T3 and PCNA-peptides also highlighted in molecular dynamics simulations. Since the hydrophobic subpocket on PCNA would be the most likely to sterically accommodate the potential binding of the T2AA fragment, only the structure of PCNA bound to T3 was used (PDB ID: 3VKX). This was also done as an intentional bias to increase the likelihood of T2AA acting as an anchor. All ligands were prepared and screened as before. The top 50% hit compounds were screened again using Glide's SP model, and the top 30% of the hits from the SP screen were docked again using Glides XP model. As before, the frequency that a particular side chain was present at a given substitution location on the peptoid backbone was tallied for the top 50 hits from the XP screen.

Figure 3:
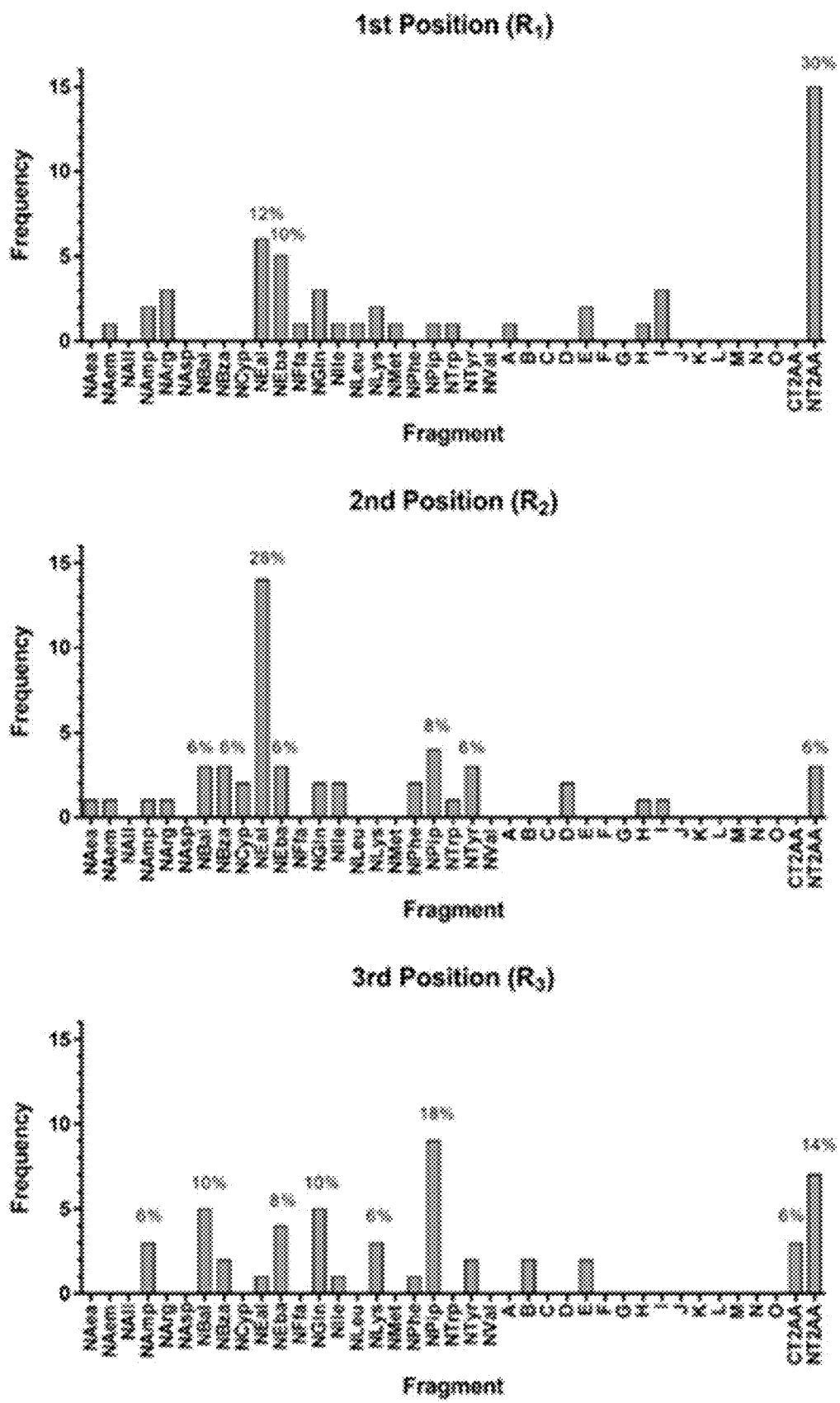
FIG. 3 shows a glide docking-based frequency with which fragments appeared in the three substitution positions on a tripeptoid backbone containing T2AA as a fragment. A set of 37 fragments, in addition to two forms of T2AA (see FIG. 1 of main text), were virtually combinatorially incorporated into a tripeptoid backbone, and were screened against the crystal structure of PCNA-T3 (PDB ID: 3VKX) in silico using the Glide HTVS, SP and XP docking algorithms. The frequency that respective fragments appeared in positions $R_1$, $R_2$ or $R_3$ were tallied for the top 50 hits. The percentage of the cumulative total of substitution frequency (out of a possible 50) at a given position is shown above columns.

From the results shown in FIG. 3, a strong preference for a small set of possible side chains was observed with NT2AA in the first and ethanol amine (NEal) being the most favored in the second position along the peptoid backbone. In contrast, the third position did not show significant preference for particular fragments. In observing the docking poses, fragments in the third position tended to be quite flexible and picked up a variety of interactions in the region proximal to the PIP box glutamine binding site. As a result, none of the third position fragments appeared to individually pick up single, substantial stabilizing interactions with PCNA. The high frequency of NT2AA as a fragment in the first position, and the comparative ease of synthesis offered a rationale for incorporation of T2AA at the N-terminus of resin-bound synthetic peptoid without the use of protecting groups (Scheme 1).

Scheme 1 Synthesis of T2AA- or non-T2AA-containing tripeptoids.

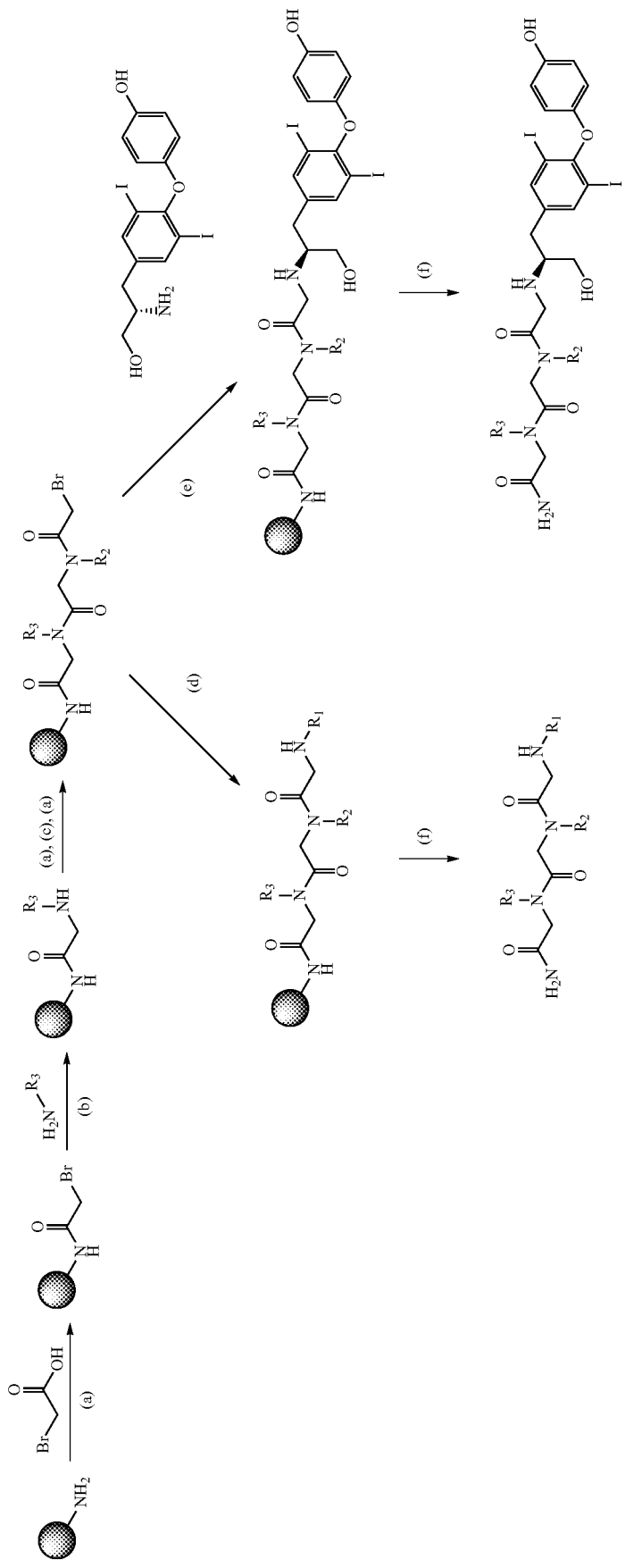

(a) $C_2H_3BrO_2$ (1 M in DMF, 20 eq.), DIC (19 eq.), 1 h, 35° C.; (b) $H_2N-R_3$ (1 M in DMF), 2 h, RT; (c) $H_2N-R_2$ (1 M in DMF), 2 h, RT; (d) $H_2N-R_1$ (1 M in DMF), 2 h, RT; (e) T2AA (19.5 eq.), DIEA (39 eq.), DMF, 16 h, RT; (f) TFA/TIS/$H_2O$ (95:2.5:2.5), 1 or 3 h, RT.

Synthesis and In Vitro Screening of Tripeptoids. Fragments that appeared in ≥5% of each position on the tripeptoid backbone were assessed for their potential incorporation into hit molecules. Among the top hit fragments were several not commercially available. To streamline the process in these early steps, NEba and NGln were not considered for synthesis due to the likely need for incorporation of appropriate acid-labile protecting groups. The preparation of the remaining non-commercially available fragments with appropriate protecting groups is outlined in Supplementary Information. In all, 85 ligands (Table 1) were synthesized using the methodology shown in Scheme 1. Most of the compounds contained the fragments that stood out from the virtual screen in a combinatorial fashion; however, some ligands were also synthesized that were not calculated to be among the hits for purposes of comparison (e.g. tripeptoids containing NAem in the 1$^{st}$ position). The total list of synthesized peptoids are shown in Table 1. Additionally, in some cases, fragments that did not appear with a high frequency in the computational screen were selected for incorporation due to chemical and/or structural similarity to fragments that did appear with a high frequency. Examples of this included NBza (substitute for NBal, NPip or NTyr), NTrp (substitute for NPip) and NMma ((4-methylphenyl) methanamine, substitute for NBal, not shown in FIG. 1).

TABLE 1

Characterization of Screened Tripeptoids

| Peptoid Sequence [a] | Calculated Mass [M + H]$^{1+}$ | Observed Mass [b] (m/z) | % Yield [c] |
|---|---|---|---|
| Gly-NPip-NBal | 443.1931 | 443.5391 | 7.19% |
| NAem-NArg-NPip | 535.2948 | 535.2581 | 47.49% |
| NAem-NArg-NTyr | 507.2999 | 507.3044 | 22.44% |
| NAem-NEal-NBal | 466.2621 | 466.2658 | 15.51% |
| NAem-NLys-NPip | 507.2887 | 507.3019 | 32.08% |
| NAem-NLys-NTyr | 479.2938 | 479.2624 | 33.93% |
| NAem-NPip-NBal | 556.2772 | 556.2767 | 22.40% |
| NAem-NPip-NBza | 570.2520 | 570.2553 | 34.71% |
| NAem-NPip-NPip | 570.2520 | 570.3911 | 73.95% |
| NAem-NPip-NTyr | 542.2570 | 542.2764 | 50.28% |
| NAem-NTyr-NPip | 542.2615 | 542.3094 | 40.60% |
| NAem-NTyr-NTyr | 514.2621 | 514.3411 | 7.16% |
| NArg-NArg-NPip | 521.2904 | 521.4318 | 32.30% |
| NArg-NIle-NBal | 464.2986 | 464.2994 | 9.40% |
| NArg-NLys-NBza | 493.2843 | 493.2887 | 32.32% |
| NArg-NLys-NPip | 493.2843 | 493.5698 | 34.09% |
| NArg-NPip-NBal | 542.2683 | 542.2703 | 29.86% |
| NArg-NPip-NBza | 556.2475 | 556.1994 | 13.39% |
| NArg-NPip-NPip | 556.2475 | 556.2516 | 8.29% |
| NArg-NPip-NTyr | 528.2526 | 528.2560 | 3.31% |
| NArg-NTyr-NBal | 514.2778 | 514.2761 | 10.11% |
| NArg-NTyr-NTyr | 500.2577 | 500.2616 | 13.73% |
| NBal-NArg-NBal | 528.2890 | 528.2910 | 12.43% |
| NBal-NEal-NBza | 487.2193 | 487.2186 | 29.94% |
| NBal-NLys-NPip | 514.2621 | 514.2656 | 29.10% |
| NBal-NLys-NTyr | 486.2672 | 486.3338 | 10.92% |
| NBal-NPip-NBal | 563.2462 | 563.1897 | 5.32% |
| NBal-NPip-NBza | 577.2254 | 577.2296 | 19.10% |
| NBal-NPip-NTyr | 549.2305 | 549.2338 | 46.74% |
| NBal-NTyr-NBal | 535.2512 | 535.2536 | 12.01% |
| NBal-NTyr-NPip | 549.2350 | 549.2787 | 26.26% |
| NBza-NArg-NBal | 542.2683 | 542.2712 | 20.25% |
| NBza-NArg-NPip | 556.2475 | 556.2506 | 49.91% |
| NBza-NLys-NBza | 528.2414 | 528.2452 | 23.80% |
| NBza-NLys-NPip | 528.2414 | 528.2443 | 49.19% |
| NBza-NLys-NTyr | 500.2465 | 500.2509 | 27.46% |

TABLE 1-continued

Characterization of Screened Tripeptoids

| Peptoid Sequence [a] | Calculated Mass [M + H]$^{1+}$ | Observed Mass [b] (m/z) | % Yield [c] |
|---|---|---|---|
| NBza-NPip-NBal | 577.2254 | 577.2283 | 14.47% |
| NBza-NPip-NBza | 591.2047 | 591.2075 | 14.18% |
| NBza-NTyr-NBal | 549.2305 | 549.2157 | 10.93% |
| NBza-NTyr-NPip | 563.2098 | 563.4002 | 17.49% |
| NEal-NEal-NBza | 411.1836 | 411.3020 | 10.34% |
| NEal-NEal-NPip | 411.1836 | 411.1878 | 22.09% |
| NEal-NEal-NTrp | 420.2203 | 420.2237 | 28.15% |
| NEal-NLys-NPip | 438.2308 | 438.2353 | 33.02% |
| NEal-NPip-NBza | 501.1941 | 501.1979 | 1.71% |
| NEal-NPip-NPip | 501.1941 | 501.1972 | 37.39% |
| NEal-NPip-NTrp | 510.2353 | 510.2364 | 11.03% |
| NLys-NArg-NPip | 493.2843 | 493.4769 | 29.45% |
| NLys-NBal-NPip | 514.2621 | 514.2684 | 35.56% |
| NLys-NEal-NBza | 438.2308 | 438.2353 | 7.50% |
| NLys-NEal-NPip | 438.2308 | 438.2351 | 34.86% |
| NLys-NIle-NBal | 437.2958 | 437.4813 | 0.82% |
| NLys-NLys-NPip | 465.2781 | 465.5013 | 28.13% |
| NLys-NPip-NBal | 514.2621 | 514.2656 | 8.62% |
| NLys-NPip-NBza | 528.2414 | 528.3454 | 36.49% |
| NLys-NPip-NMma | 513.2826 | 513.6709 | 6.75% |
| NLys-NPip-NPip | 528.2414 | 528.3143 | 27.24% |
| NLys-NTyr-NBal | 486.2672 | 486.2708 | 20.16% |
| NLys-NTyr-NBza | 500.2465 | 500.2403 | 21.69% |
| NLys-NTyr-NPip | 500.2465 | 500.2713 | 10.44% |
| NMma-NPip-NBal | 562.2666 | 562.6433 | 23.68% |
| NPip-NPip-NPip | 591.2047 | 591.8057 | 3.97% |
| NTyr-NArg-NBal | 514.2734 | 514.3009 | 11.59% |
| NTyr-NArg-NPip | 528.2526 | 528.3313 | 3.44% |
| NTyr-NEal-NBal | 459.2199 | 459.2245 | 16.40% |
| NTyr-NIle-NBal | 471.2563 | 471.3852 | 12.99% |
| NTyr-NLys-NPip | 500.2509 | 500.2503 | 47.78% |
| NTyr-NLys-NTyr | 472.2516 | 472.1906 | 4.57% |
| NTyr-NPip-NBal | 549.2350 | 549.6621 | 0.75% |
| NTyr-NPip-NBza | 563.2098 | 563.2132 | 27.46% |
| NTyr-NPip-NPip | 563.2098 | 563.2128 | 23.04% |
| NTyr-NPip-NTyr | 535.2193 | 535.2186 | 45.90% |
| NTyr-NTyr-NPip | 535.2149 | 535.2551 | 23.10% |
| T2AA-Asn | 682.9864 | 682.9854 | 5.78% |
| T2AA-Gln | 697.0021 | 697.0003 | 8.15% |
| T2AA-Gly | 625.9649 | 625.9629 | 0.81% |
| T2AA-Gly-NBal | 803.0439 | 803.0422 | 9.83% |
| T2AA-Gly-NPip | 817.0232 | 817.0266 | 4.51% |
| T2AA-NEal-Gly | 727.0126 | 727.0109 | 3.81% |
| T2AA-NEal-NBal | 847.0701 | 847.0695 | 1.67% |
| T2AA-NEal-NMma | 846.0861 | 846.8161 | 13.13% |
| T2AA-NEal-NPip | 861.0450 | 861.0513 | 5.95% |
| T2AA-NEal-NTyr | 833.0545 | 833.0562 | 15.00% |
| T2AA-NPip-NLys | 888.0967 | 888.0983 | 9.41% |
| T2AA-NPip-NPip | 951.0560 | 951.0586 | 4.95% |

Figure 4:
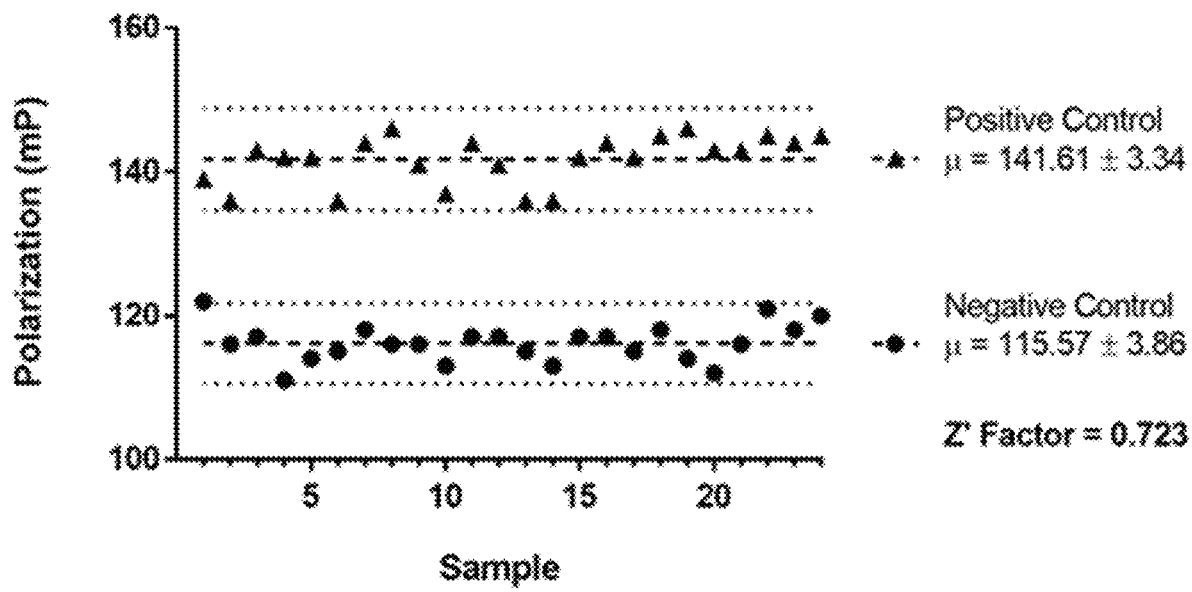
FIG. 4 is Z'-Factor analysis. Polarization values for 24 replicate samples of both positive and negative controls were used to evaluate the quality of the assay platform. 10 nM FAM-PL (SEQ ID NO: 4; FAM: 5-fluorescein; PL: POGO ligase peptide (SEQ ID NO: 2)) and 100 nM PCNA served as the positive control, while 10 nM FAM-PL in binding buffer served as the negative control. Dashed lines indicate the mean value of each set of controls, and dotted lines indicate the 95% prediction interval.
Figure 5:
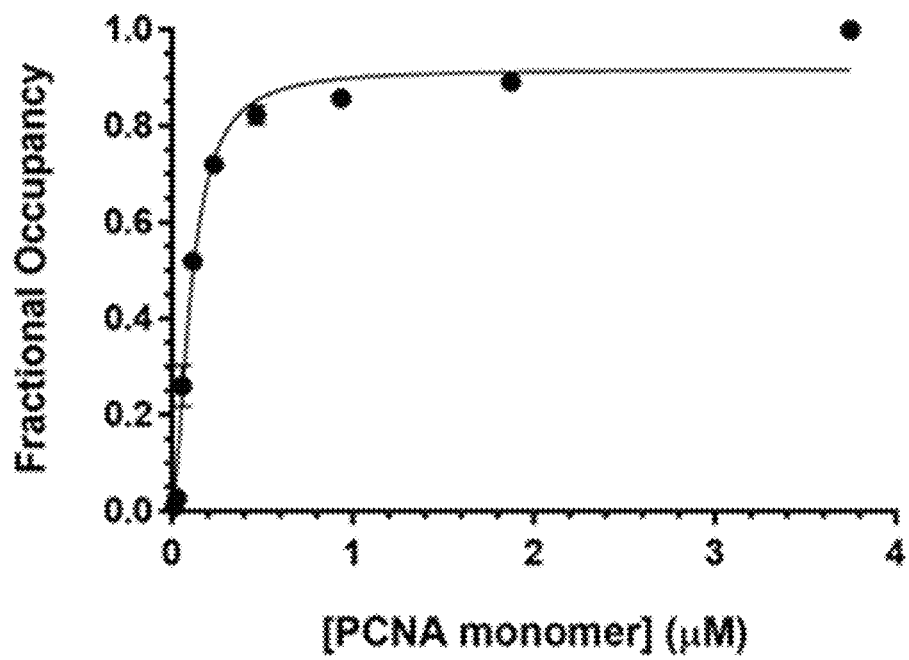
FIG. 5 shows PCNA titration for determining affinity of FAM-PL. Increasing amounts of recombinant PCNA were added to a fixed concentration of the FAM-PL peptide (5 nM) in binding buffer. The data were fit to Equation 2.3 was used to determine the $K_d$ value for the peptide (here, the calculated affinity was 107 nM).

[a] N-substituted side chains listed from N-terminus to most C-terminal
[b] as determined by high resolution electrospray ionization or MALDI-TOF
[c] based on dry mass recovery after HPLC purification After synthesis and purification, peptoids were screened in a fluorescence polarization (FP) assay to find ligands that disrupted the interaction between His-tagged PCNA and fluorescein-labeled Pogo Ligase peptide (FAM-PL) (Kontopidis, G., et al. Proc. Natl. Acad. Sci. U.S.A 2005, 102 (6), 1871-1876). In the design of the assay, conditions were adopted from Pedley et al., 2016, to improve the dynamic range between bound and unbound FAM-PL. While an acceptable Z-score was determined using the original 10 nM peptide and 100 nM PCNA (FIG. 4), an improved dynamic range was established by adjusting the ligand and receptor concentrations. Using a fixed concentration of the FAM-PL peptide (5 nM) and two-fold increasing concentrations of recombinant His-tagged PCNA in a dose-response fashion, non-linear regression indicated a Kd for PL peptide of 107 nM (FIG. 5), similar to what has been previously reported (Kontopidis, G, et al. 2005). Because more than 80% of the peptide was bound at a PCNA concentration of 1 this protein-receptor concentration was selected for use in subsequent displacement assays. The inclusion of PCNA was included in the overall calculations of $K_i$ values.

Figure 6:
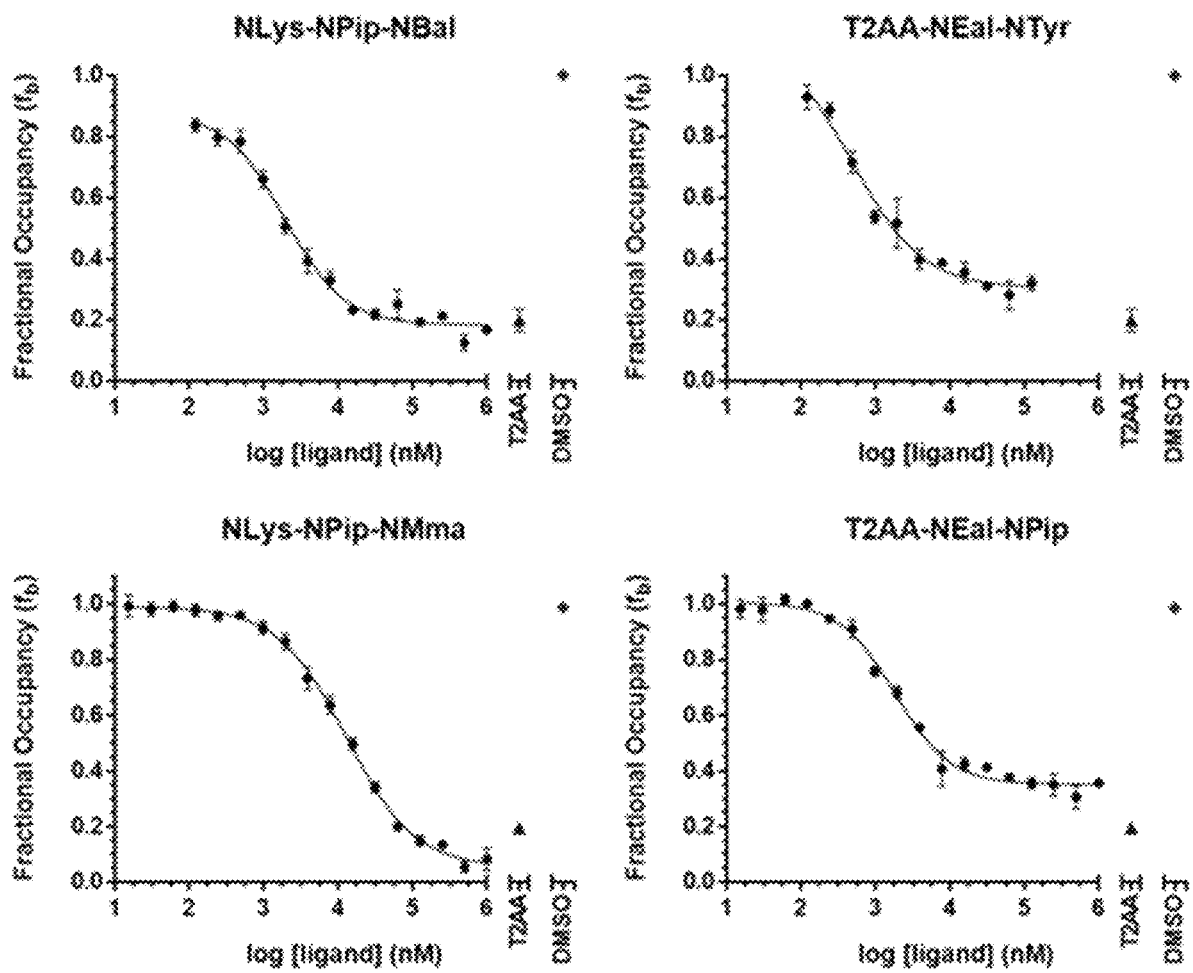
FIG. 6 are dose response curves of four of the top hit peptoid-based compounds from the fluorescent polarization screen. Peptoid-based ligands were subjected to two-fold dose response analysis. Solutions were plated in duplicates of four, and error bars represent the standard error around the mean. 1 mM T2AA in DMSO serves as the positive control, and DMSO alone serves as the negative control.
Figure 7:
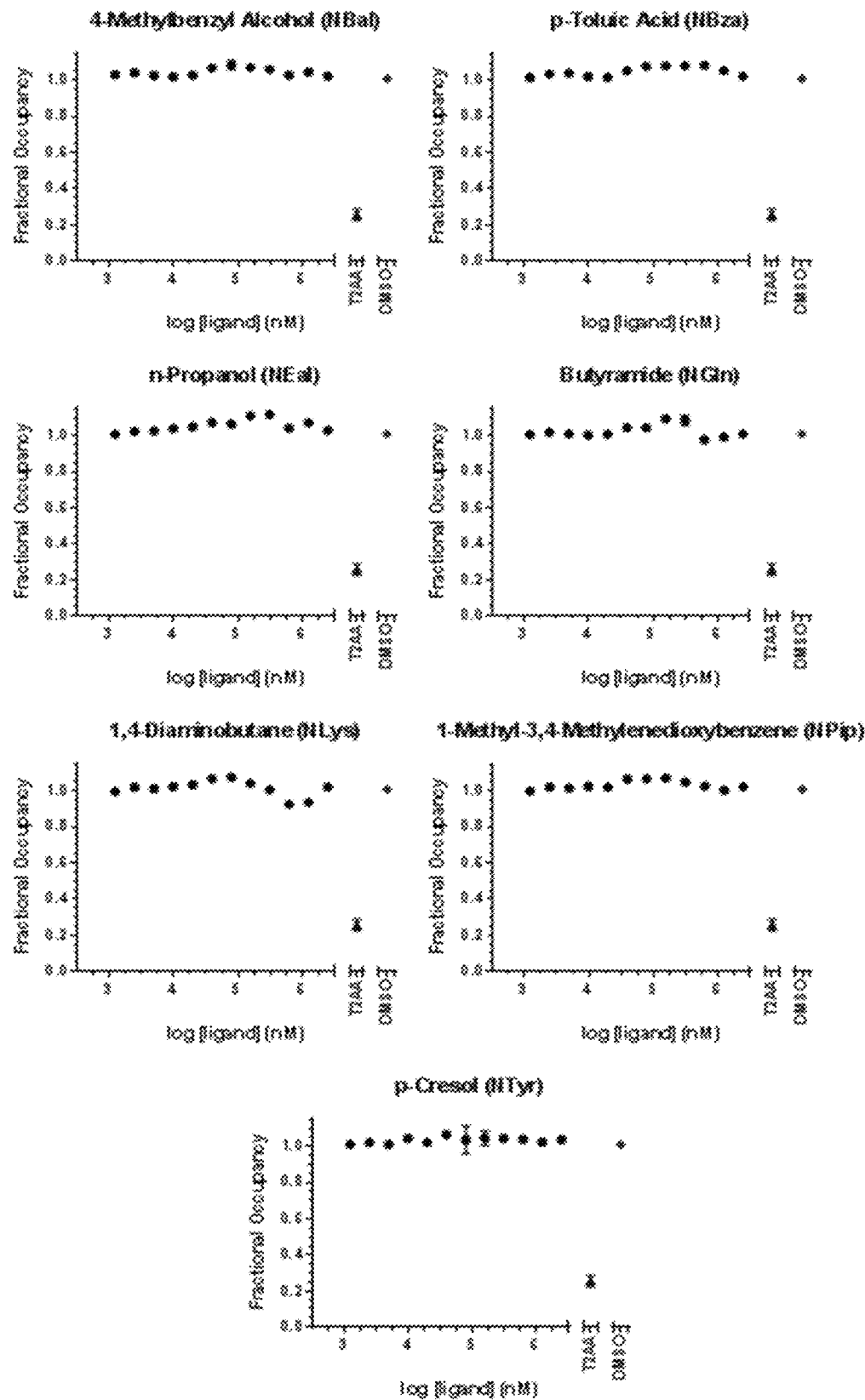
FIG. 7 are dose response curves of individual peptoid fragments. The fragments present in hit tripeptoid molecules were screened individually in the FP assay to determine if they could individually disrupt the binding between PCNA and the PL peptide. None of the small fragments showed any evidence of inhibition. T2AA was selected as the positive control, and DMSO as the negative control. Error bars represent the standard error of the mean.
Figure 8:
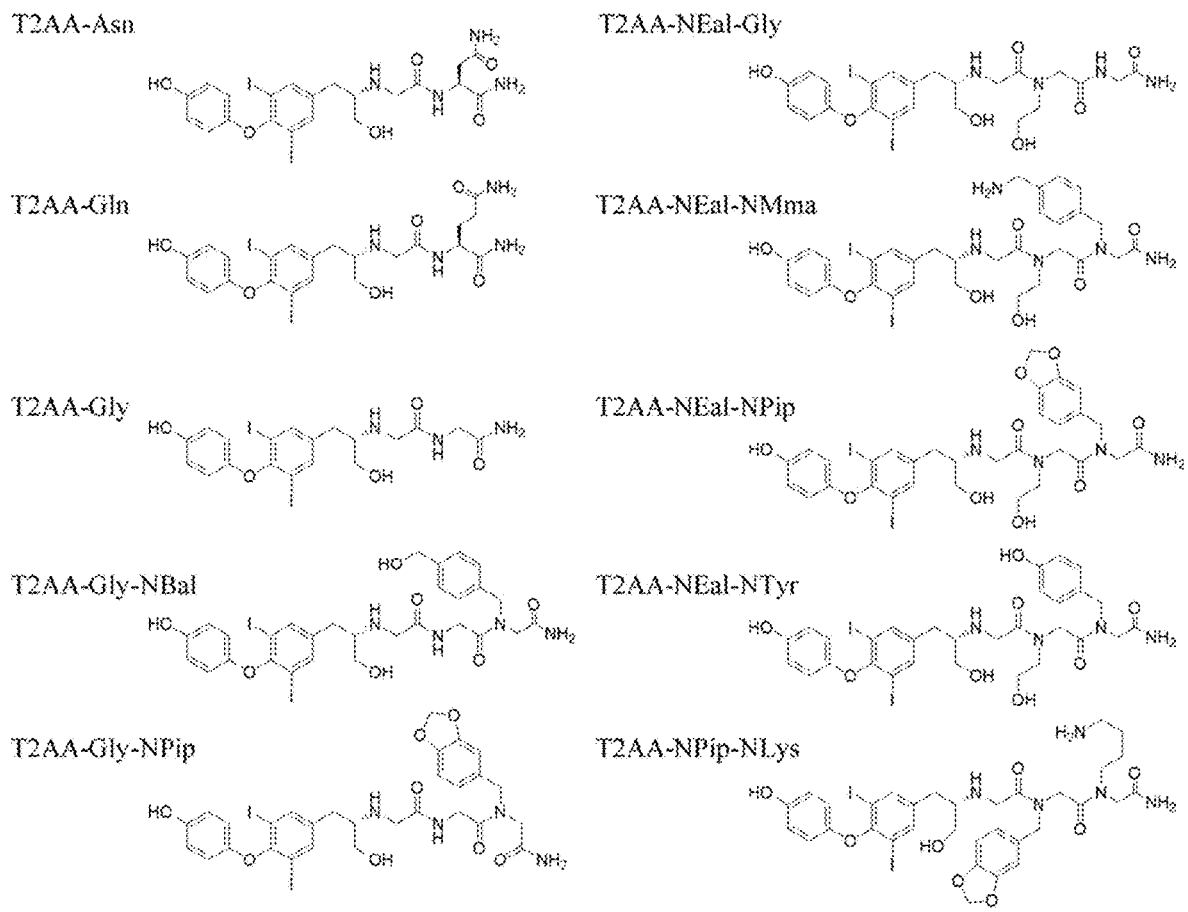
FIG. 8 describes structures of T2AA-conjugates. For second generation peptoid inhibitors of PCNA, T2AA was coupled to the N-terminus of peptoids or peptides anchored on solid phase resin to generate the molecules shown above.

The compounds were screened in this FP assay at concentrations of 1 mM and 250 µM to find general hits (data not shown???). T2AA was used as the positive control since it is known to disrupt the interaction between FAM-PL and PCNA, and would be the basis for comparison against the ligands in this study. From the initial screen, sixteen ligands were identified that were able to negatively affect the binding between PCNA and FAM-PL at 250 Series of two-fold dilutions of each hit were performed to generate dose response curves. Anisotropy was converted to fractional occupancy, and $IC_{50}$ values were determined for each peptoid by performing non-linear regression fits of each dose response curve using equation 4. Inhibition constants ($K_i$ values) were calculated from the resultant $IC_{50}$ values using equation 5 (Table 2). Examples of dose response curves for four of the top hits are shown in FIG. 6. As a control, individual fragments that make up the top hits, including NGln, NLys, NPip, NTyr, NBal, NBza and NEal, were screened in the FP assay to determine whether they were individually capable of disrupting PCNA-PL peptide binding (FIG. 7). However, none of the fragments showed any evidence of inhibition.

TABLE 2

Hit Compound IC50 and Ki Values
Measured by Fluorescence Polarization

| Compound Name | $IC_{50}$ (µM) * | $K_i$ (µM) *† |
|---|---|---|
| T2AA | 1.34 ± 0.33 | 0.128 ± 0.0318 |
| Gly-NPip-NBal | 7.74 ± 3.41 | 0.745 ± 0.328 |
| NBal-NLys-NTyr | > 600 | > 50 |
| NLys-NPip-NBal | 1.94 ± 0.51 | 0.186 ± 0.0491 |
| NLys-NPip-NMma | 12.93 ± 1.97 | 1.24 ± 0.190 |
| NLys-NTyr-NBal | ~ 165 | ~ 16 |
| NMma-NPip-NBal | 11.69 ± 2.55 | 1.12 ± 0.245 |
| T2AA-Asn | 7.20 ± 2.74 | 0.693 ± 0.264 |
| T2AA-Gln | 3.52 ± 1.65 | 0.339 ± 0.159 |
| T2AA-Gly | 2.91 ± 0.91 | 0.280 ± 0.0876 |
| T2AA-Gly-NBal | 5.66 ± 1.67 | 0.545 ± 0.161 |
| T2AA-Gly-NPip | 16.17 ± 3.71 | 1.56 ± 0.357 |
| T2AA-NEal-Gly | 1.17 ± 0.37 | 0.113 ± 0.0356 |
| T2AA-NEal-NMma | 1.18 ± 0.24 | 0.114 ± 0.0231 |
| T2AA-NEal-NPip | 1.82 ± 0.37 | 0.175 ± 0.0356 |
| T2AA-NEal-NTyr | 0.482 ± 0.328 | 0.0464 ± 0.0316 |
| T2AA-NPip-NLys | 6.13 ± 2.84 | 0.590 ± 0.273 |

* Values are represented as the 95% confidence interval around the mean
*† Calculated using equation 5

Figure 9:
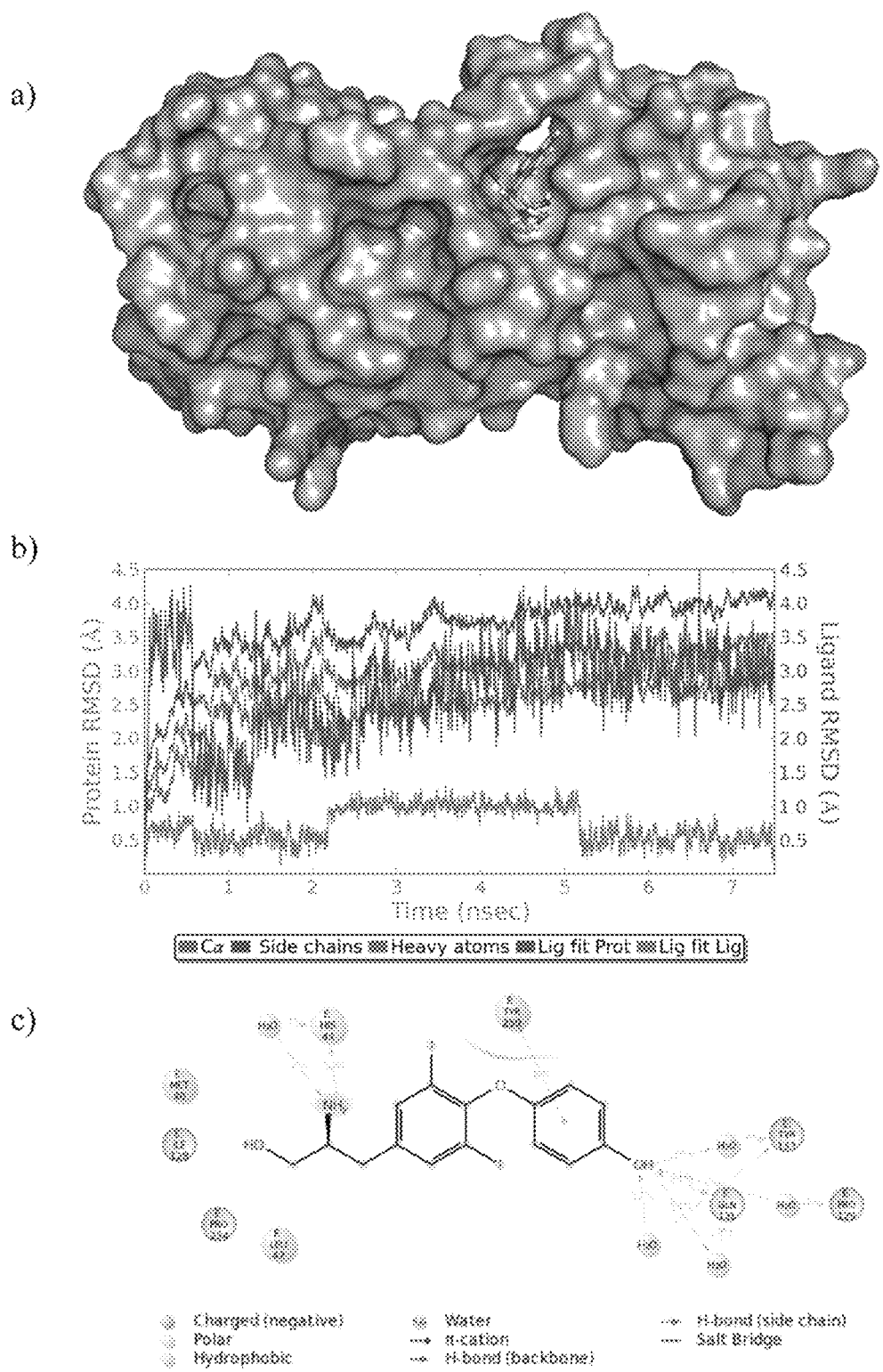
FIG. 9 is PCNA-T2AA MD simulation output. (a) Average structure of the final 50 frames of the PCNA-T2AA MD simulation. (b) RMSD diagram demonstrating simulation convergence. (c) Ligand interaction diagram showing molecular contacts over the course of the simulation.
Figure 10:
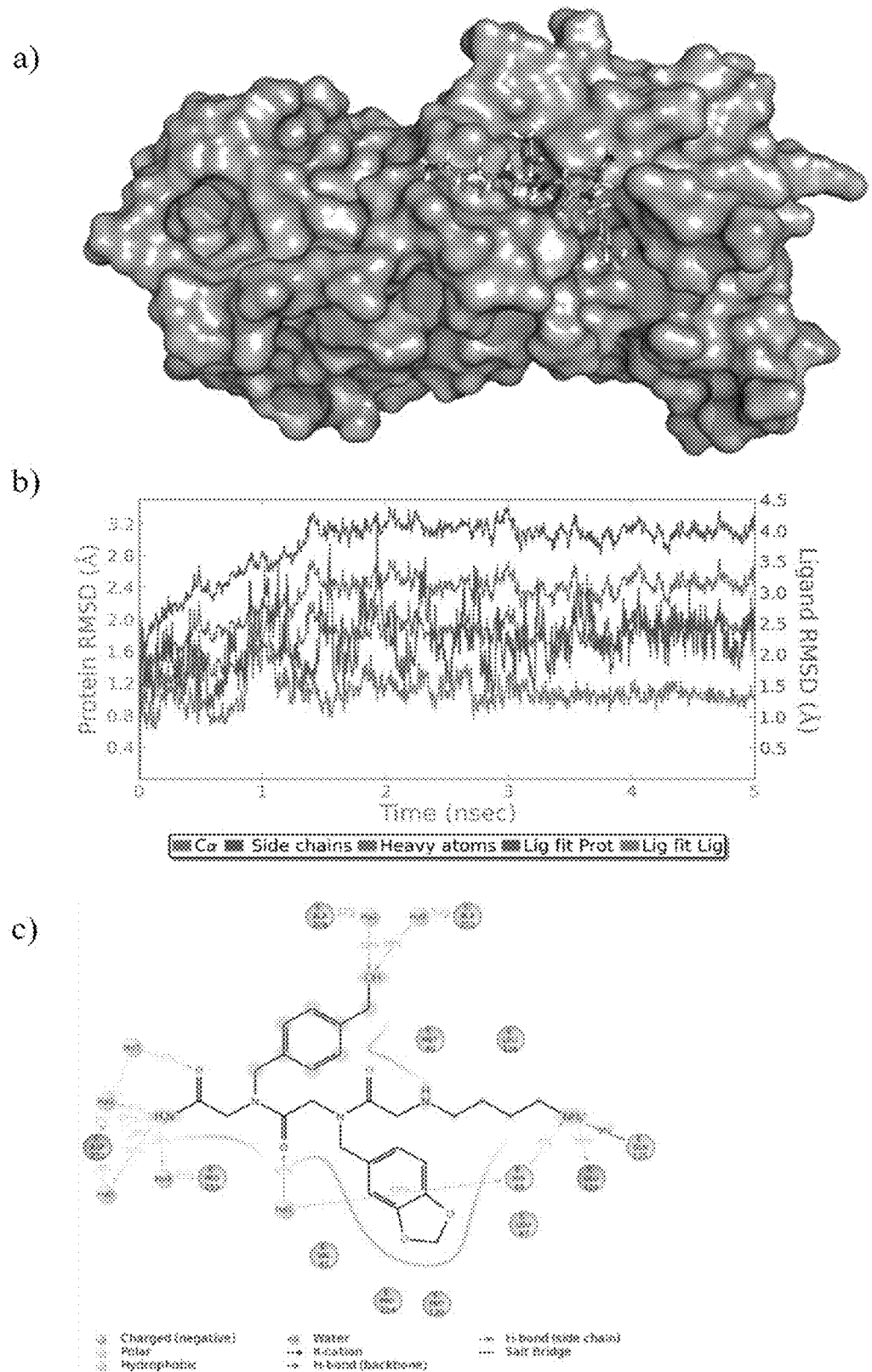
FIG. 10 shows PCNA-NLys-NPip-NBal MD simulation output. (a) Average structure of the final 50 frames of the PCNA-NLys-NPip-NBal MD simulation. (b) RMSD diagram demonstrating simulation convergence. (c) Ligand interaction diagram showing molecular contacts over the course of the simulation.
Figure 11:
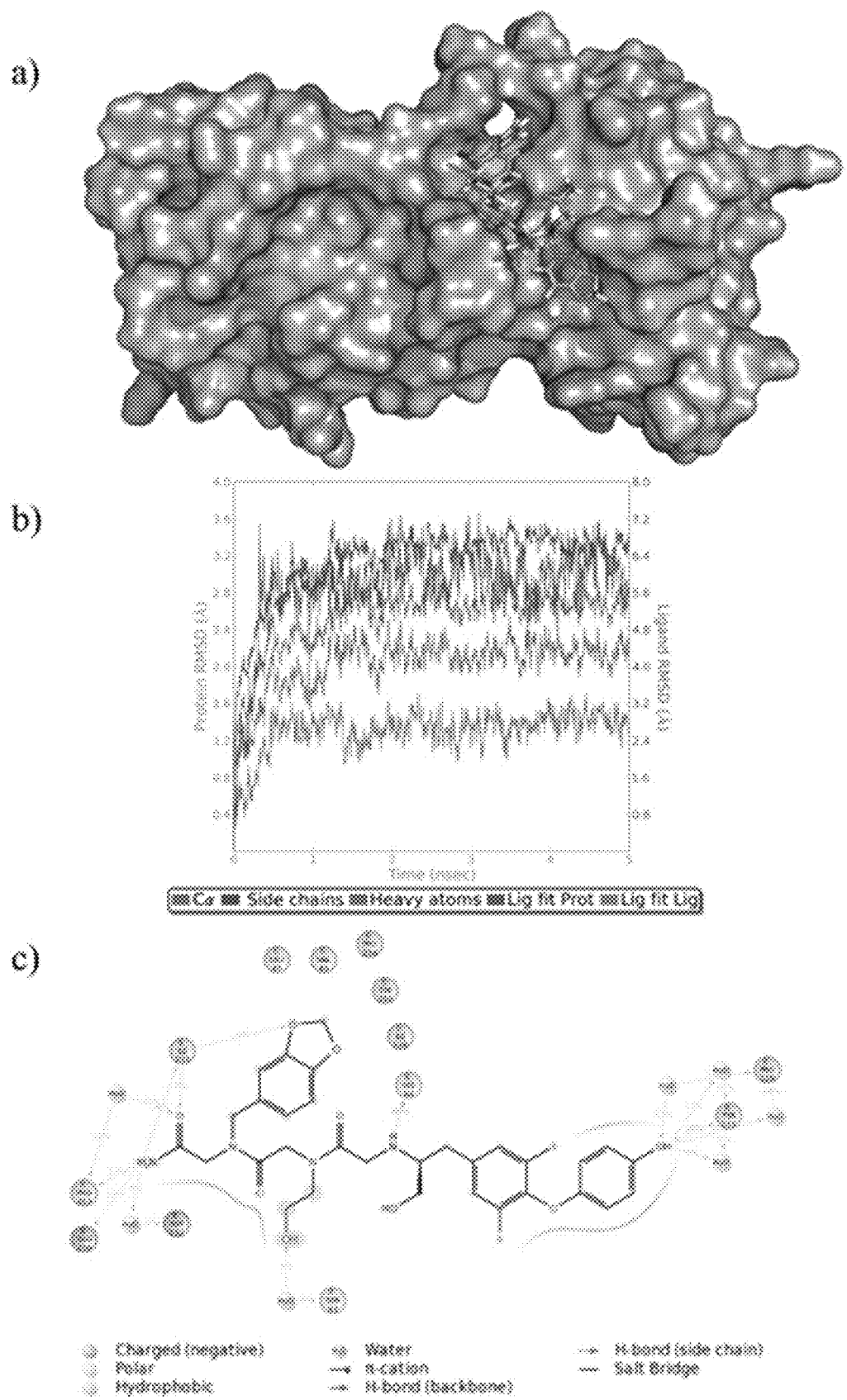
FIG. 11 is PCNA-T2AA-NEal-NPip MD simulation output. (a) Average structure of the final 50 frames of the PCNA-T2AA-NEal-NPip MD simulation. (b) RMSD diagram demonstrating simulation convergence. (c) Ligand interaction diagram showing molecular contacts over the course of the simulation.
Figure 12:
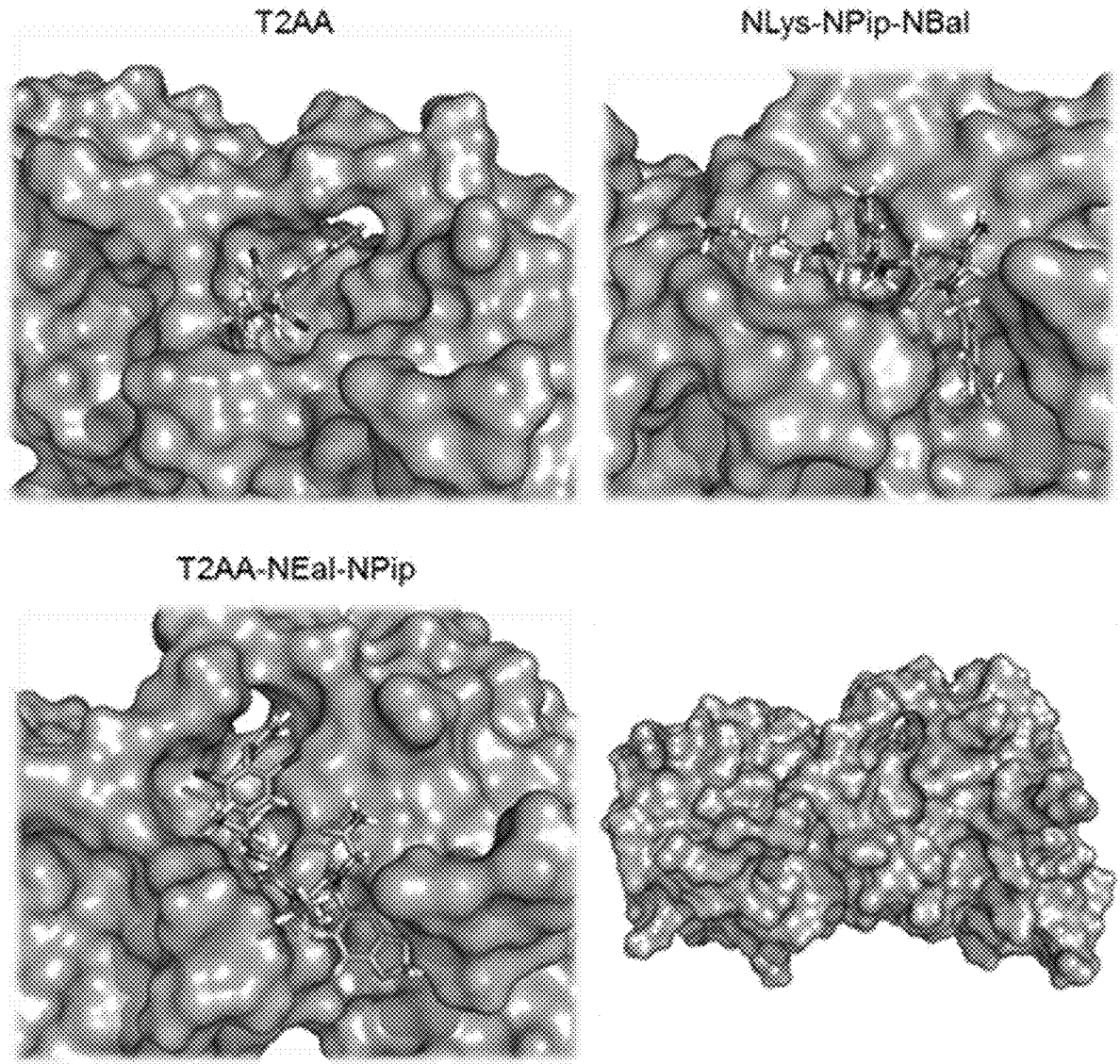
FIG. 12 shows average structures of the final 50 frames of molecular dynamic simulations. The final 50 simulation trajectory frames for each analyzed peptoid ligand were averaged using VMD, and the resulting structures visualized using Pymol. The hydrophobic pocket (orange) and PIP Box glutamine binding site (blue) are highlighted in each. The whole structure of the PCNA monomer is shown in the bottom right for comparative purposes.

Identification of Molecular Recognition Features of PCNA for Peptoid Ligands. In an effort to understand better the molecular features of the peptoids-PCNA interactions, molecular dynamics simulations (MDs) were performed with two selected hits, NLys-NPip-NBal and T2AA-NEal-NPip, as well as T2AA, in complex with PCNA. As outlined in the experimental methods, each ligand was first docked into the co-crystal structure of PCNA and PL-peptide (PDB ID: 1VYJ), with the peptide removed, using the Glide induced-fit model in Maestro. These structures provided starting points for the MDs, as well as to ensure that there were no conflicts on an atomic scale due to steric clashing or unfavorable ionic contacts. Each simulation was run for 5.0 ns, or until it converged, as judged by the change in protein Cα and side chain RMSD over time (FIG. 9-11). Upon completion, simulation trajectories were first aligned to the first frame of their own simulation, and then the simulations were aligned to one another based on the position of their Cα atoms using VMD. The final fifty frames for each MD were averaged to give a final structure for each PCNA-ligand complex (FIG. 12).

Figure 13:
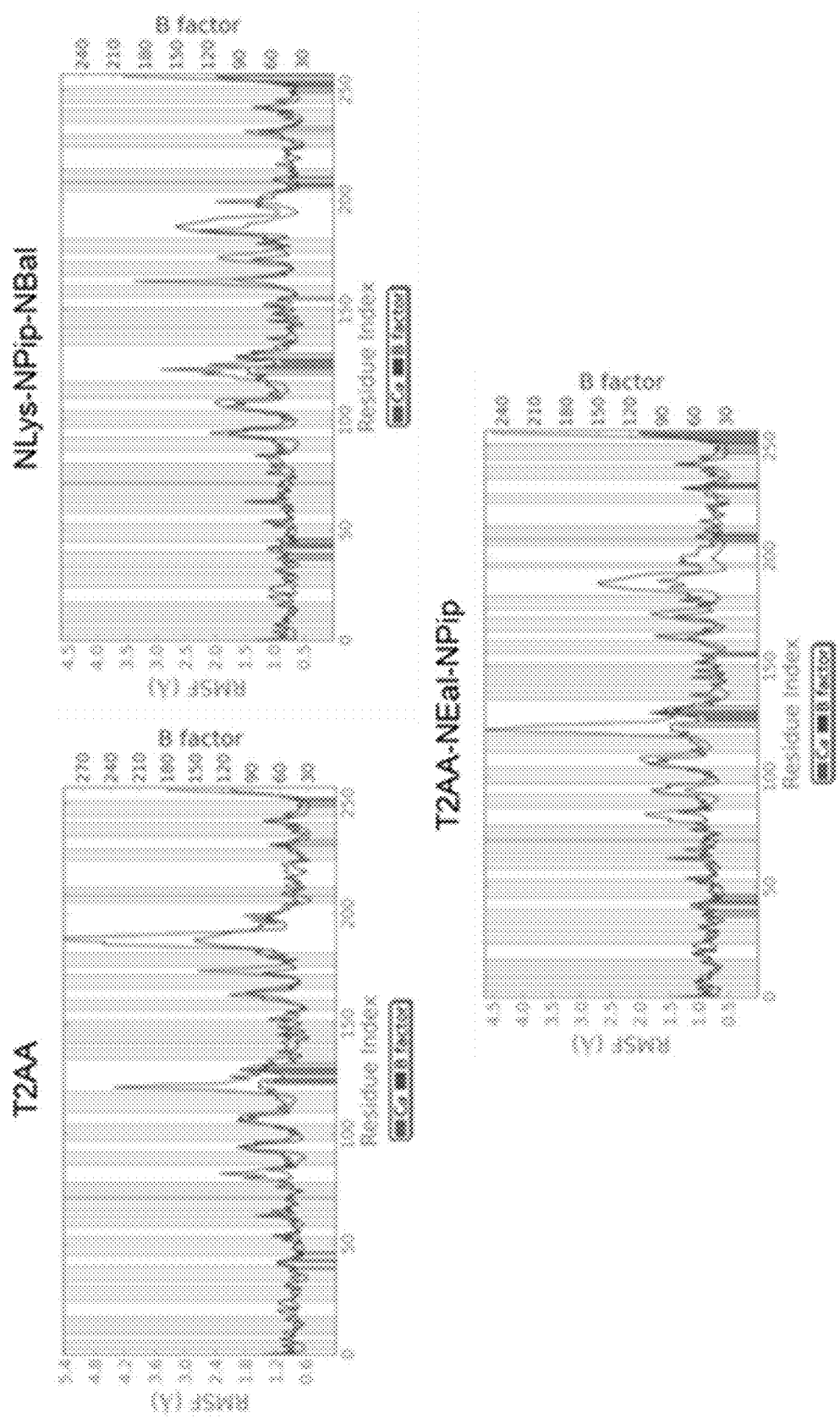
FIG. 13 is MD simulation Ca atom RMSD fluctuation by residue number. RMSD diagrams of each PCNA-peptoid MD simulation are shown. Peaks indicate areas of the protein that fluctuate the most during the simulation. Alpha helical and beta-strand regions are highlighted in orange and blue, respectively. Contacts between the ligand and PCNA residues are represented as green lines projecting upward from the x-axis.
Figure 14:
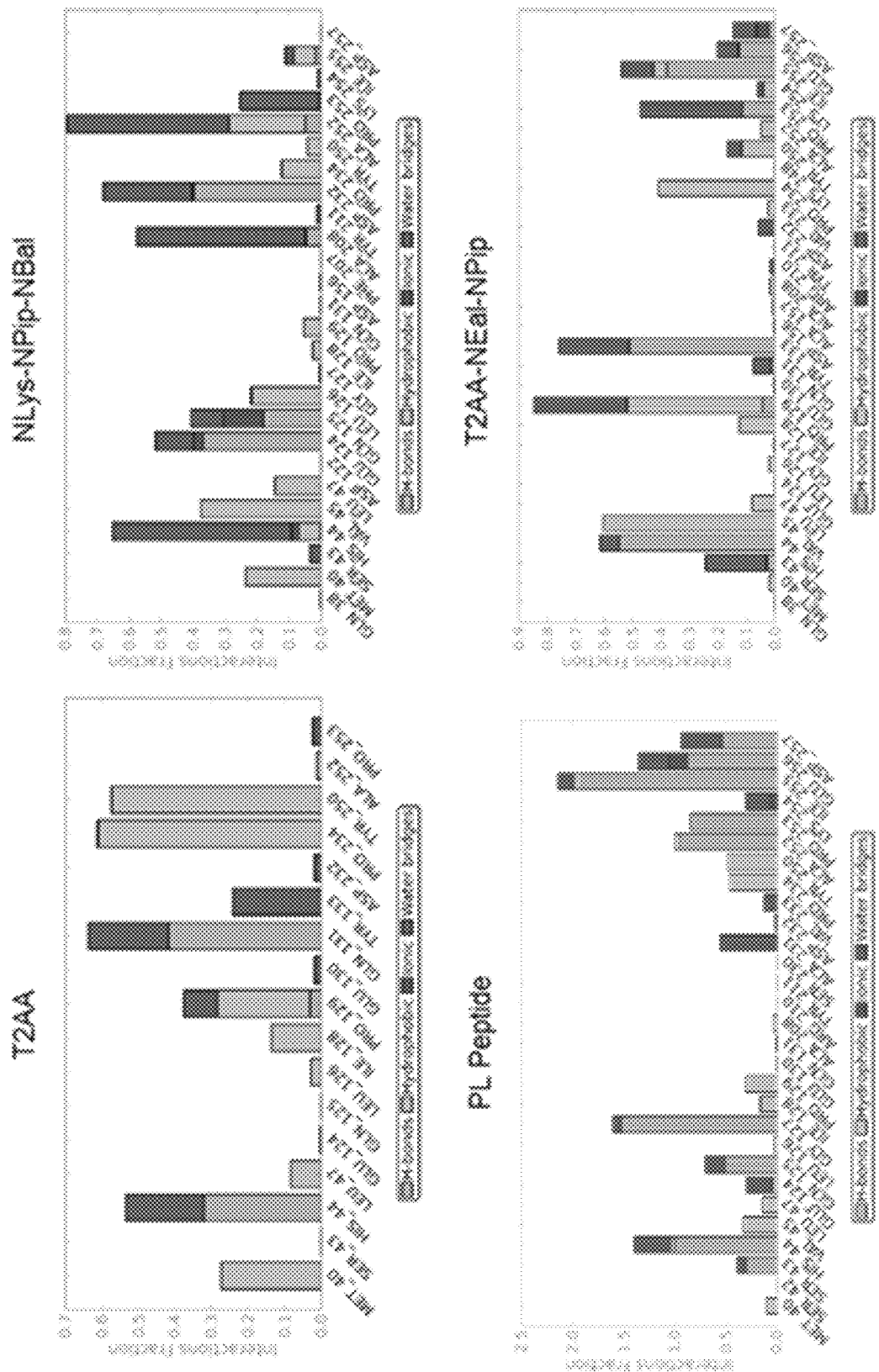
FIG. 14 are MD simulation interaction diagrams. Interactions between PCNA amino acids and peptoid ligands or the PL peptide were monitored over the course of each MD simulation. The number of trajectory frames in which an interaction occurred was recorded and listed as a fraction of the total number of possible simulation frames. Numbers larger than 1.0 indicate that during the simulation, two or more simultaneous interactions between a given protein residue and the ligand were taking place.

Upon analysis, it was clear that each of the resulting complexes differed significantly from the co-crystal structure of PCNA-PL. It has been previously reported that PCNA is quite flexible and can adopt a variety of conformations to optimize ligand binding.[20] The results here suggest that this principle is conserved given the large differences in the PIP box binding region on the protein between each MD. Regions on PCNA that appeared to drive the conformational difference between each structure most substantially were between residues 80-86, 93-97, 104-111, 117-136, 162-166, 172-177, 181-194 and 251-257 (FIG. 13). Perhaps unsurprisingly, each of these regions was found in either a β-turn or unordered loop structure. The PIP box binding site itself is surrounded by four distinct flexible regions comprised of β-turn residues 40-46, the disordered interdomain connecting loop residues 117-136, β-turn residues 229-235 and disordered loop residues 251-257. Of the protein residues that looked to be the most important for direct interaction with each peptoid ligand, His44, Pro129, Pro234, Ala252, Pro253 and Ile255 each interacted with each peptoid ligand to various significant degrees in each of the MDs (FIG. 14). Almost all of the significant contacts were shared with T2AA and the PL peptide, indicating that the inhibitors occupy many of the 'anchoring' contacts between PCNA and PL, enhancing their antagonistic activity.

Figure 15:
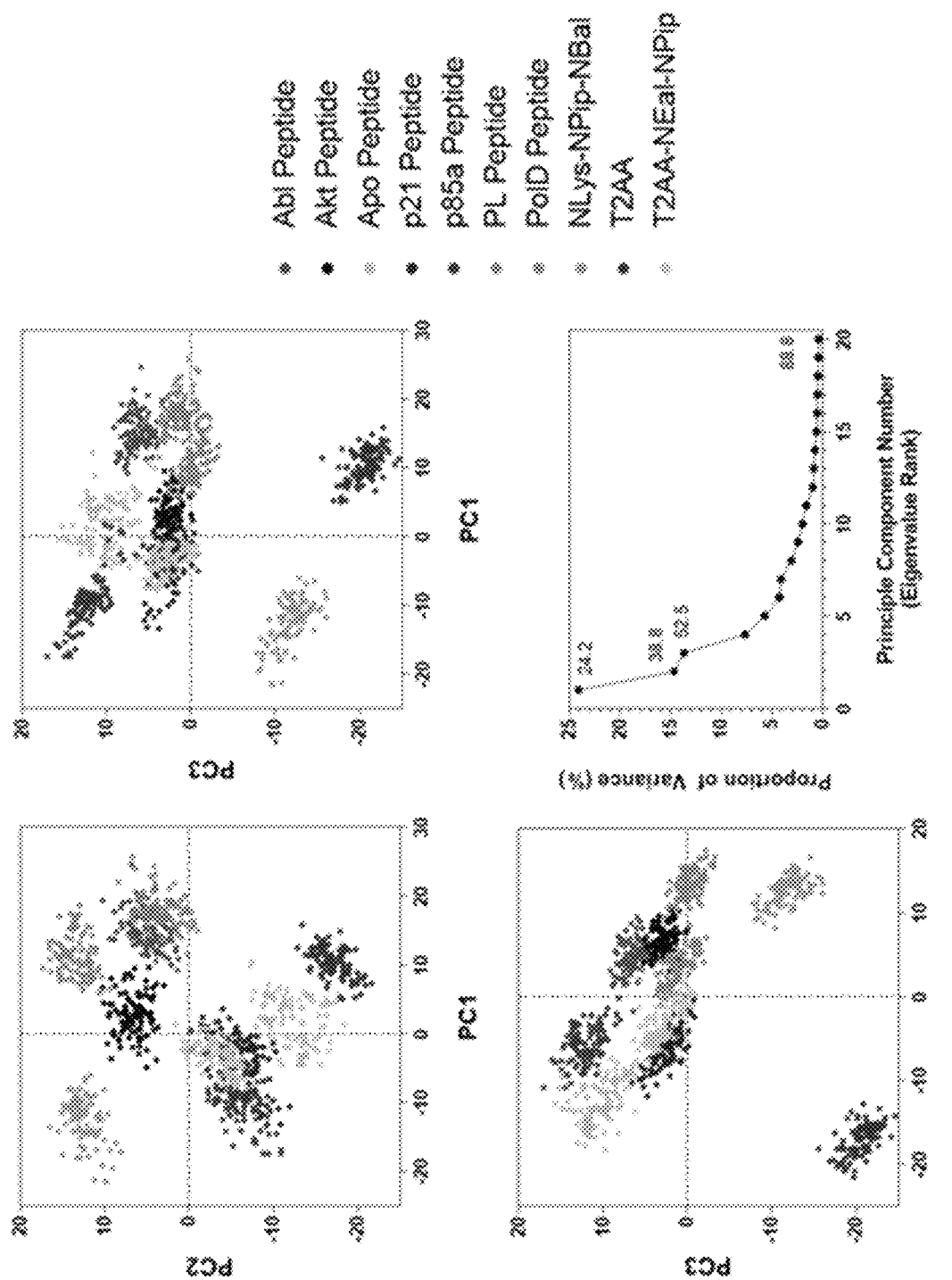
FIG. 15 is principle component analysis of PCNA topology variance. The final 100 frames of each PCNA-ligand MD trajectory were aligned based on the position of the PCNA Ca backbone atoms. A principle component analysis of the aligned trajectories shows differential clustering of PCNA conformations (residues 1-257) when in complex with either a peptoid-based ligand or a PIP Box-containing peptide. Principle components 1-3 (PC1, PC2 and PC3) for each structure were clustered and plotted along with the proportion of variance for each principle component.

To further visualize the differences between each MD output structure, a principal component analysis (PCA) of the trajectory snapshots for the Cα atoms of each PCNA-ligand complex was performed (FIG. 15). In addition to the outputs from the MDs performed here, trajectories of PCNA bound to various known binding peptides, as used in the study by Pedley, et al. 2016, were included in the PCA for comparison. In this additional set were trajectories of PCNA in complex with the DNA polymerase δ, PL, p85-α, p21, Apo, Akt or Abl peptide. In a PCA, the principle components, which are themselves orthogonal eigenvectors, describe the axes of maximal variance of the distribution of structures. The percentage of variance of the fluctuation of protein atom position in each dimension is characterized by a corresponding eigenvalue. By clustering structures in principle component space, a focus is on the relationships between different structures in terms of their major structural displacements. In the context of this work, clustering along principle components 1, 2 and 3 allows for the comparison of the significant structural differences between each conformation of PCNA which covers more than 50% of their conformational variance (FIG. 15, bottom right panel).

Figure 16:
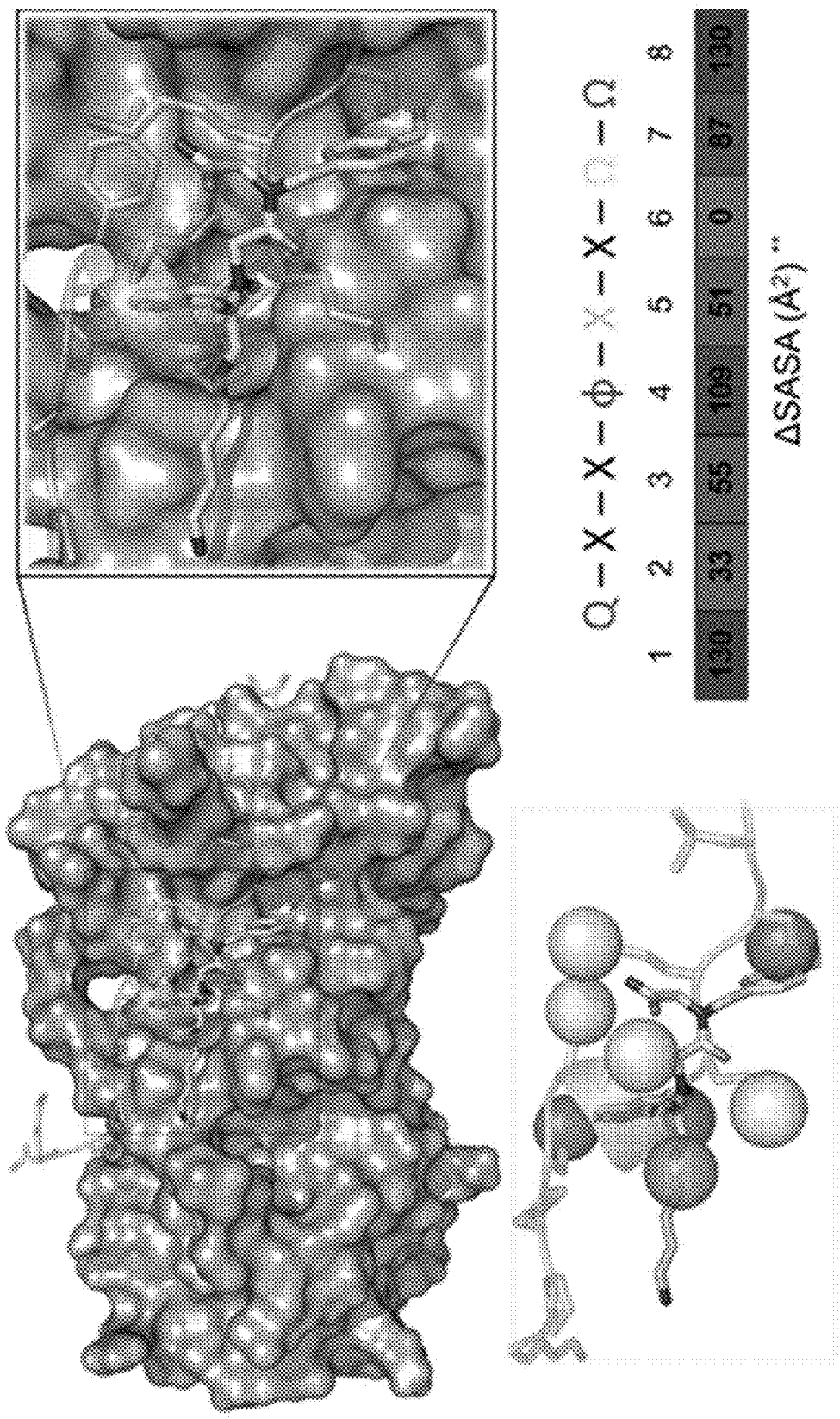
FIG. 16 shows peptoid inhibitors disrupt key PCNA-PIP Box interactions. (top) The competitive peptoid inhibitors, such as NLys-NPip-NBal (yellow sticks), are projected to bind at the PIP Box binding site on PCNA (gray surface; PDB ID: 1VYJ), which overlaps with the PL peptide (green cartoon and sticks). (bottom left) NLys-NPip-NBal overlays key contact points between the PL peptide's PIP Box and PCNA. Spheres represent PIP Box amino acid residues. Colors indicate direct disruption of key (red) or non-key (orange) residues, and non-disruption of key (yellow) or non-key (white) residues. (bottom right) Results from Pedley, et al (2014) demonstrating that residues 1, 4, 7 and 8 of the PL peptide's PIP Box act as anchoring residues. Changes in surface accessible surface area (SASA) were calculated with ANCHOR,[44] measuring the differences between bound and unbound forms of the PL peptide.

As predicted, the PCA indicated distinct differences in the topology of the PCNA-ligand interaction sites. Of all the structures, PCNA-T2AA was the most different from the rest, likely due to the fact that the inhibitor is much smaller than the peptoid-based compounds and does not project outside of the hydrophobic pocket. Although the structures were mostly separated from one another, there were some similarities in the eigenvectors. For example, though PCNA-PL and PCNA-NLys-NPip-NBal were well separated in clustering space, they both had nearly equivalent second principle components. Likewise, the population distribution of PCNA-PL and PCNA-T2AA had nearly equivalent first principle components. This result would indicate that these conformations are very similar in certain dimensions. The potential implications for predicting inhibitory efficiency from this PCA are not yet clear, but this information will be useful for classifying ligand-receptor complexes with respect to the Analysis of the molecular dynamic simulations indicates that the peptoid inhibitors are active due to their ability to disrupt key interactions between PCNA and the PL peptide (FIG. 16). While in the most general sense, these compounds provide a geometric hindrance to PIP Box binding, it is also significant that these compounds prevent PCNA from forming important anchoring contacts with PIP box residues. Computational results from Pedley, et al. 2016, demonstrate that the conserved amino acids of the PIP box—glutamine in position 1, a hydrophobic residue in position 4 and aromatic residues in positions 7 and 8—act as anchoring residues that drive conformational stability of the complex between PCNA and PIP box-containing peptides/proteins. Disrupting these points of contact would substantially weaken their interaction, and would effectively abolish binding.

Classifying Peptoid-Based Molecules as Inhibitors of Protein-Protein Interactions. Inhibitors of protein-protein interactions (iPPIs) have characteristics that distinguish them from other traditional inhibitors in that they display such features as higher molecular weight, higher hydrophobicity and a larger number of aromatic rings.[30,31] iPPIs also demonstrate higher degrees of globularity, lower distribution of hydrophilic regions, smaller proportions of exposed hydrophilic regions and stronger capacities to bind hydrophobic patches at the core of protein-protein interfaces as compared to inhibitors of classical targets such as enzymes.[32] Though peptoid-like molecules have been demonstrated to disrupt PPIs,[33,34] it was not clear how the fragment compositions in the combinatorial libraries influence the features that would be predicted to be classified as iPPIs prima facie. All of the fragments shown in FIG. 1, including both variants of T2AA, were used to create a combinatorial set of tripeptoids in Schrödinger as before.

The peptoids were characterized by implementing a Bayesian classifier method analogous to the one used in Morelli, X. et al (2011).[31] To perform the Bayesian classification, the 2P2I Hunter data set,[31,35,36] which is a library of molecules that contains 40 known iPPIs and 1018 small molecules that are not inhibitors of PPIs, was first obtained. Next, four descriptors were calculated for each compound—globularity, CW2, EDmin3 and IW4—using the same methodology as Kuenemann, et al (2014).[32] These descriptors measure the following factors, respectively: 1) three-dimensional shape globularity; 2) ratio between the surface of the hydrophilic regions calculated at −0.5 kcal/mol and the total molecular surface (it is proportional to the concentration of hydrophilic regions [involved in weak potential polar interactions] compared to the total surface area); 3) third lowest local minimum of the interaction energy (in kcal/mol) of a dry probe (it measures the potential interaction energy of the ligand with a hydrophobic object); 4) unbalance between the center of mass of a molecule and the barycenter of its hydrophilic (IW) interacting regions (a high integy moment is a clear concentration of hydrophilic interacting regions at one extremity of the compound).

Figure 17:
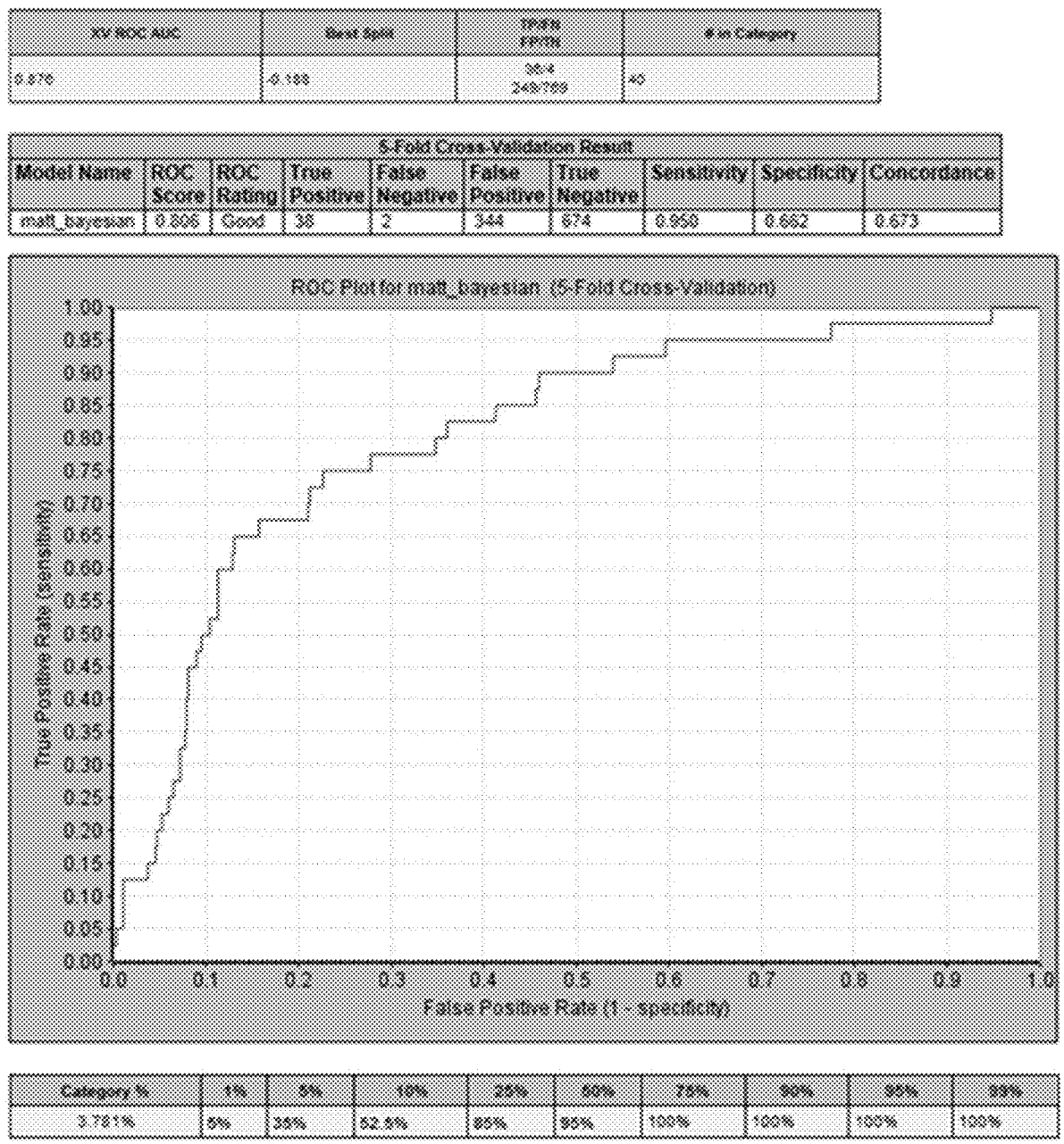
FIG. 17 shows enrichment plot for Bayesian model prediction of the 2P2I Hunter compound set. A leave-one-out cross-validation of the Bayesian model for the 1058-ligand 2P2I Hunter set was performed, an enrichment plot was generated, and the percentages of true category members captured at particular cutoff percentages were listed. From this, a best split value was calculated as −0.188 for the Bayesian score.

In calculating the Bayesian cutoff, each sample was left out one at a time, and a model built using the results of the samples, with that model used to predict the left-out sample. Once all the samples had predictions, a ROC plot was generated, and the area under the curve (ROC AUC) calculated (FIG. 17). Best Split was determined by picking the split that minimized the sum of the percent misclassified for category members and for category nonmembers, using the cross-validated score for each sample. A contingency table was constructed, containing the number of true positives, false negatives, false positives and true negatives. Based on the resulting calculated cutoff of −0.188, 38 out of the 40 iPPIs as well as 244 out of the 1018 non-iPPIs were predicted to be true iPPIs.

Next, this same model was applied to the library of tripeptoid ligands, and the same four descriptors were calculated for each molecule—globularity, CW2, EDmin3 and IW4. The peptoids were prepared in the same way as the compounds in the training set, with all possible ionization states at a pH of 7. When considering the entire set of the tripeptoids, both those that are predicted to be iPPIs and those that are not, the statistics for the distribution of descriptor scores (see Tables 3-5) indicate that those molecules are much more similar in globularity to other known iPPIs than non-iPPIs. For CW2, the tripeptoids had a higher score than either iPPIs or non-iPPIs, likely due to the fact that these peptoids, on average, have more exposed hydrophilic regions than what would be expected for classical drugs. Overall, as a whole, the full set of tripeptoids was not strongly associated with either iPPIs or non-iPPIs, as there are ligands that strongly share features with other iPPIs, and those that don't. However, when only the tripeptoids that showed up as experimental hits were considered, 15 out of 16 peptoids (94%), along with T2AA, were predicted to be iPPIs, with the lone exception being Gly-NPip-NBal.

TABLE 3

Peptoid Descriptor Statistics from Bayesian Model

| Statistic | Globularity | CW2 | EDmin3 | IW4 |
|---|---|---|---|---|
| Mean | 0.123096 | 2.19173 | −2.62519 | 1.99723 |
| Median | 0.11273 | 2.204385 | −2.59537 | 1.91726 |
| Minimum | 0.027005 | 1.58044 | −4.37756 | 0.059068 |
| Maximum | 0.654219 | 2.76792 | −1.89029 | 6.11639 |
| Skew | 1.691743 | −0.33117 | −0.6282 | 0.488549 |

TABLE 4 iPPI Descriptor Statistics from Bayesian Model

| Statistic | Globularity | CW2 | EDmin3 | IW4 |
|---|---|---|---|---|
| Mean | 0.11331 | 1.953635 | −2.84006 | 2.699039 |
| Median | 0.079983 | 1.92631 | −2.81911 | 2.54485 |
| Minimum | 0.013987 | 1.54225 | −3.30688 | 0.525021 |
| Maximum | 0.45662 | 2.37198 | −2.4452 | 5.5549 |
| Skew | 1.613415 | 0.248895 | −0.48162 | 0.282107 |

TABLE 5

Non-iPPI Descriptor Statistics from Bayesian Model

| Statistic | Globularity | CW2 | EDmin3 | IW4 |
|---|---|---|---|---|
| Mean | 0.055457 | 2.082103 | −2.48144 | 2.579951 |
| Median | 0.037349 | 2.05015 | −2.45079 | 2.440295 |
| Minimum | 0 | 1.26745 | −3.51407 | 0 |
| Maximum | 0.356383 | 3.04432 | −1.70217 | 8.53636 |
| Skew | 1.820263 | 0.377792 | −0.55035 | 0.525307 |

It is not yet clear whether in the context of PCNA-protein complex formation, directly targeting PCNA alone would be sufficient to result in an efficacious treatment option. There is some evidence that PCNA is implicated in some way with each DNA damage repair pathway given that various key proteins in each of those pathways have PIP boxes. However, many mechanisms in cells are redundant and are capable of compensating for the loss of a single pathway regulator. It may be that targeting PCNA will have clinical utility only when other synthetically lethal drugs are present that target compensatory proteins for the processes of the DDR (Tucker, C. L., et al., *Nat. Genet.* 2003, 35 (3), 204-205). Additionally, it is not yet understood how the flexibility of PCNA would influence the efficacy of a single drug targeting the PIP box binding site. In addition to the study by Pedley, et al., 2016, the MD simulations performed in this work demonstrate that PCNA can adopt very different conformations, depending on the ligand that is bound to it. The question remains as to whether a given ligand would better inhibit the interaction between one PCNA-protein complex or another. It may also be that a ligand binding to PCNA at one site produces an allosteric effect that would affect PCNA-protein complexes at other sites. The functional consequences of this are not clear, but it could mean that attempting to stabilize a specific conformation of PCNA to achieve a singular response is much more complicated than anticipated.

EXPERIMENTAL PROCEDURES

The present invention can be better understood by reference to the following examples which are offered by way of illustration. The present invention is not limited to the examples given herein.

Reagents and solvents were purchased from Sigma Aldrich unless otherwise noted. Materials were repurified via recrystallization or distillation as necessary before use. NMR experiments were performed on Bruker (Bruker Corp., Billerica, Mass.) ARX300 (300 MHz), ARX400 (400 MHz) or DRX500 (500 MHz) instruments. Low resolution electrospray ionization (ESI) and atmospheric pressure chemical ionization (APCI) studies were carried out on an Agilent 6320 Ion Trap (Agilent Labs, Santa Clara, Calif.) mass spectrometer. High resolution mass measurements were obtained on a LTQ Orbitrap XL mass spectrometer (ThermoScientific Corp.) utilizing electrospray ionization (ESI). Molecular masses and sequences of peptides or peptoids were validated on an Applied Biosystems (Framingham, Mass.) MALDI-TOF/TOF 4800 mass analyzer, or Applied Biosystems Voyager DE PRO mass spectrometer using either 2,5-dihydroxy benzoic acid or α-cyano-4-hydroxy cinnamic acid matrices. TLC analyses were performed on Merck aluminum-backed F254 silica gel plates. Protein and peptide concentrations were determined by UV absorbance at 280 nm. Fluorescent peptide concentrations were determined by absorbance at 494 nm. Stock solutions of each polypeptoid were made by measuring the dry mass of each in pre-dried, pre-weighed screw-cap vials, and adding the volume of DMSO necessary to give 10 mM solutions. Stock solutions of compounds containing N-terminal 5-carboxyfluorescein were made by measuring the aborbance at 494 nm, using an extinction coefficient of 79,000 L mol$^{-1}$ cm$^{-1}$ and Beer's Law (A=εbc) to calculate concentration. Data analyses and graphical representations were performed in Microsoft Excel, GraphPad Prism 6 or OriginPro 2015.

Ligation Independent Cloning of N-terminal His-tag PCNA Construct. Ligation independent cloning compatible expression vector pEV-L8 containing an N-terminal His-tag and TEV protease recognition site was linearized by digestion with Ssp1 (New England Biolabs), purified by gel filtration, and treated with T4 DNA polymerase (Novagen) in the presence of dGTP (New England Biolabs) for 30 minutes at 22° C., followed by heat inactivation at 75° C. for 20 minutes. The PCNA fragment was amplified by PCR from a template plasmid (Genecopeia) using a high-fidelity polymerase Platinum Pfx DNA polymerase (Invitrogen). The resulting PCR products were treated with T4 DNA polymerase in the presence of dCTP to generate 5' overhangs necessary for annealing. A total of 0.2 pmol of each insert was incubated with 0.01 pmol of pEV-L8 vector in 3 µL reaction mix at 22° C. for 10 minutes followed by addition of 1 µL of 25 mM EDTA at 22° C. for 5 minutes. Annealing reaction products were transformed into X10Gold competent cells (Strategene) and plated on LB agar containing 50 µg/mL kanamycin. Individual colonies were grown and the constructs were assessed by PCR for insert size and verified by sequencing before propagating the plasmid.

Expression and Induction of N-terminal His-tag PCNA (SEQ ID NO: 3). 10 µL aliquots of chemically competent BL21 (DE3) *E. Coli* cells (Agilent) were transformed via heat shock with 1 µL of purified plasmid encoding the fusion protein, N-terminal (His)$_6$-PCNA for 30 seconds at 42° C. The cells were then immediately placed on ice for 2 minutes, and 140 µL of SOC medium was added. Transformed cells were allowed to grow for 1 hour at 37° C. before streaking on a LB agar plate containing 50 µg/mL kanamycin. Single isolated colonies were picked and grown at 37° C. to an OD of 0.7-1.0 in the presence of 50 µg/mL kanamycin. Transformed cells were induced with 0.4 mM IPTG for 4 hours at 37° C. Transformed cells were pelleted at 4,000×g for 20 minutes at 4° C., and stored at −80° C. until lysis.

Purification of N-terminal His-tagged PCNA. Two pellets of transformed BL21 (DE3) *E. Coli* cells were each resuspended in 20 ml of ice-cold lysis buffer (50 mM Tris HCl at pH 8.0, 0.15 mM NaCl), lysed by sonication at a 30% amp output for 3 minutes (20 second pulses), and centrifuged at 4,000×g for 20 minutes at 4° C. Each supernatant was decanted and combined. Recombinant (His)$_6$-PCNA fusion protein was then purified from the soluble fraction by affinity column chromatography using Ni-NTA resin at 4° C. After charging the column resin with the entire soluble protein fraction, the column was washed with 20 mM imidazole in Tris buffer at pH 8.0 to remove nonspecific binding protein. (His)$_6$-PCNA was then eluted with 10 mL of 1M imidazole in Tris buffer at pH 8.0. The eluted protein was diluted two-fold with dialysis buffer (25 mM HEPES at pH 7.4, 10% glycerol, 0.01% Triton X-100), DTT and EDTA were added to a final concentration of 2 mM, and the entire solution was diluted two-fold with 2M ammonium sulfate in 25 mM Tris buffer at pH 8.0 to give a final (NH$_4$)$_2$SO$_4$ concentration of 1M. The solution was agitated for 1 hour at 4° C., and during that time (His)$_6$-PCNA precipitated from solution. The precipitated protein was pelleted by centrifugation (5,000×g for 10 minutes), the supernatant decanted, and the protein pellet dissolved into 10 mL of dialysis buffer. The protein concentration was immediately assessed via measuring its absorbance at 280 nm (using an extinction coefficient of 16,000 M$^{-1}$ cm$^{-1}$), and the protein solution was diluted as necessary to give a stock concentration of 4 µM. This was then dialyzed for 24 hours, swapping the dialysis buffer twice with fresh 25 mM HEPES at pH 7.4, 10% glycerol, 0.01% Triton X-100. After dialysis, the protein concentration was re-confirmed by measurement of its absorbance at 280 nm.

Synthesis of Non-Commercially Available Primary Amines and T2AA

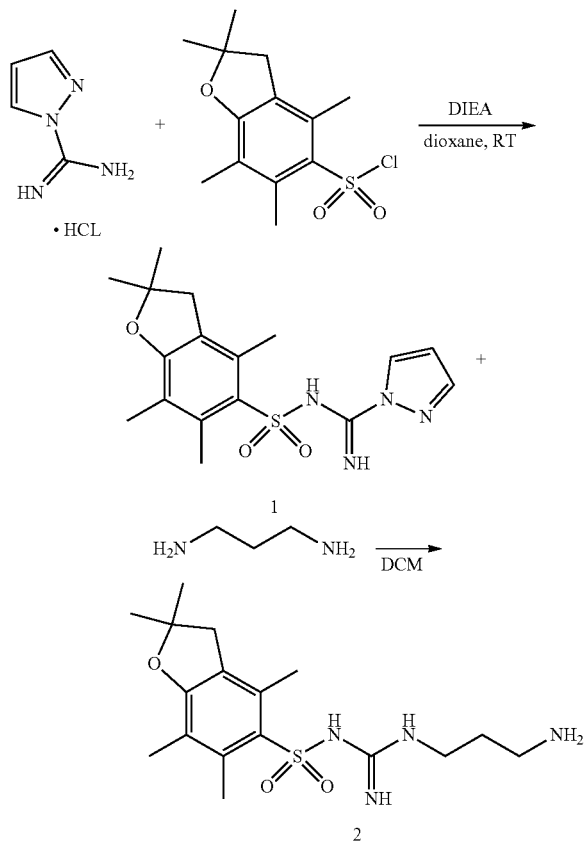

Synthesis of NArg. Synthesis of N-((2,2,4,6,7-pentamethyl-2,3-dihydrobenzofuran-5-yl)sulfonyl)-1H-pyrazole-1-carboximidamide (1). 16.16 g (55.96 mmol) of 2,2,5,7,8-pentamethylchroman-6-sulfonyl chloride (Combi-Blocks, Inc., San Diego, Calif.) was dissolved in dioxane (200 mL), and 9.07 g (61.88 mmol) of 1H-pyrazole-1-carboxamidine HCl dissolved in dioxane (200 mL) was added to the solution followed by 22 mL (2 eq.) of DIEA. The reaction mixture was stirred at room temperature for 48 hours, at which time all of the 1H-pyrazole-1-carboxamidine HCl had been consumed as confirmed via TLC. The dioxane was evaporated in vacuo and the remaining brown oil was redissolved into 200 mL DCM. The organic layer was washed with water (3×200 mL), dried over sodium sulfate and evaporated to give a brown solid. The crude material was recrystallized three times from ethanol to give 13.17 g (64.9% yield) of 1 as a white solid. $^1$H NMR (500 MHz, CDCl$_3$) δ 8.21 (dd, J=2.8, 0.7 Hz, 1H), 7.67 (dd, J=1.6, 0.7 Hz, 1H), 6.40 (dd, J=2.9, 1.6 Hz, 1H), 2.98 (s, 2H), 2.62 (s, 3H), 2.56 (s, 3H), 2.11 (s, 3H), 1.47 (s, 6H). $^{13}$C NMR (126 MHz, CDCl$_3$) δ 12.34, 17.86, 19.16, 28.48, 42.99, 86.67, 109.47, 117.74, 124.83, 128.92, 130.88, 132.98, 139.13, 143.44, 148.66, 159.41. HRMS (ESI): calculated mass (C$_{17}$H$_{23}$N$_4$O$_3$S) [M+H]$^{1+}$: 363.1491, mass found m/z: 363.1510 [M+H]$^{1+}$.

Synthesis of N—(N-(3-aminopropyl)carbamimidoyl)-2,2,4,6,7-pentamethyl-2,3-dihydrobenzofuran-5-sulfonamide (2; "NArg"). 5.88 g (17.5 mmol) of 1 was dissolved into DCM (100 mL) and was added dropwise to 6.75 g (91.1 mmol; 5.2 equiv.) of 1,3-diaminopropane dispersed in DCM (100 mL) at room temperature while stirring. The reaction was allowed to stir for 24 hours, at which time TLC showed that all of 1 had been consumed. The reaction mixture was washed with water (3×100 mL) and brine (100 mL), the organic layer was dried over sodium sulfate, and the organics were evaporated in vacuo to give an off-white solid. The product was recrystallized using ethyl acetate/hexanes to give 3.57 g (59.7% yield) of 2 as a white solid. $^1$H NMR (500 MHz, CDCl$_3$) δ 3.30 (t, J=6.09 Hz, 2H), 3.25 (q, J=6.20 Hz, 1H, NH), 3.20 (q, J=6.65 Hz, 1H, NH), 2.93 (s, 2H), 2.88 (t, J=7.63 Hz, 2H), 2.54 (s, 3H), 2.47 (s, 3H), 2.07 (s, 3H), 1.82-1.70 (m, 2H), 1.66 (t, J=6.66 Hz, 1H, NH), 1.45 (s, 6H). $^{13}$C NMR (126 MHz, CDCl$_3$) δ 158.71, 138.15, 132.32, 132.12, 124.62, 117.50, 109.22, 86.35, 43.10, 39.78, 37.98, 28.50, 19.23, 17.85, 12.39. HRMS (ESI): calculated mass (C$_{17}$H$_{29}$N$_4$O$_3$S) [M+H]$^{1+}$: 369.1961, mass found m/z: 369.1980 [M+H]$^{1+}$.

Synthesis of NBa1

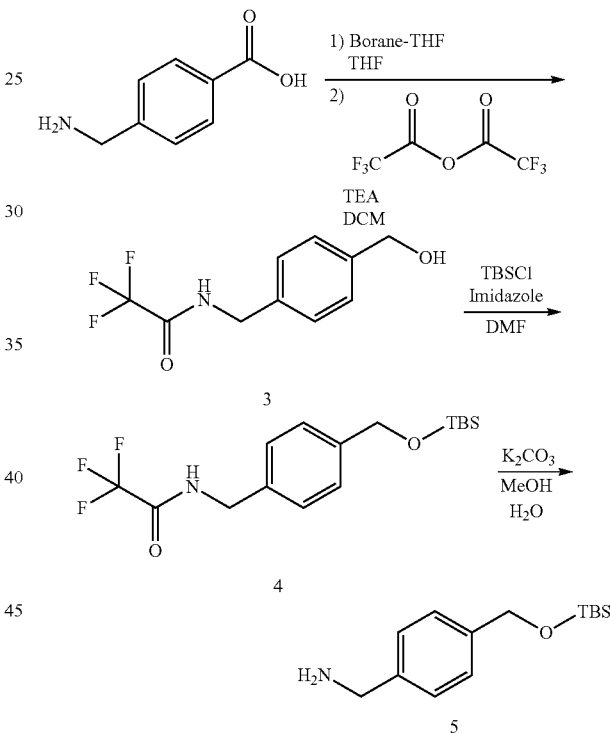

Synthesis of 2,2,2-trifluoro-N-(4-(hydroxymethyl)benzyl)acetamide (3). 20.0 g (132 mmol) of 4-(aminomethyl)benzoic acid was dispersed in 100 mL of anhydrous THF, and 350 mL (2.65 equiv.) of 1M borane-THF in THF was added dropwise. The reaction mixture was heated to reflux for eight hours, and then allowed to cool to room temperature. 100 mL of MeOH was added to quench the remaining borane-THF, and the reaction was stirred for an additional 15 minutes. The reaction solution was then filtered over celite and evaporated in vacuo to give a light yellow solid. 250 mL of DCM was then added to the reaction flask containing the crude intermediate product, followed by 37 mL (2 equiv.) of triethylamine. The reaction was cooled to 0° C., 21 mL (1.1 equiv.) of trifluoroacetic anhydride was added dropwise and the reaction was allowed to stir overnight, allowing it to gradually reach room temperature. After 22 hours of reaction time, all of the starting material had been consumed as evidenced by TLC. 250 mL of water was added to the reaction and the organic layer was separated. The aqueous layer was extracted once more with 250 mL of DCM, the combined organics were washed with water (100 mL), and were dried over sodium sulfate, filtered and evaporated in vacuo to give a thick yellow oil. This oil was purified via automated flash chromatography (EPCLC W-Prep 2XY, Yamazen Corp., Yodogawa-Ku Osaka, Japan) using DCM/MeOH as the eluents. The fractions containing the desired product were combined and evaporated to give 15.87 g (51.44% yield for both steps) of 3 as a white solid. $^1$H NMR (300 MHz, CDCl$_3$) δ 7.34 (d, J=8.17 Hz, 2H), 7.26 (d, J=8.16 Hz, 2H), 6.86 (s, br, 1H), 4.66 (s, 2H), 4.49 (d, J=5.86 Hz, 2H), 2.02 (s, 1H).

Synthesis of N-(4-(((tert-butyldimethylsilyl)oxy)methyl) benzyl)-2,2,2-trifluoroacetamide (4). 15.68 g (67.24 mmol) of 3 was dissolved in DMF (200 mL), followed by the addition of 9.17 g (2 equiv.) of imidazole and 11.29 g (1.11 equiv.) of tert-butyl dimethylchlorosilane. The reaction was allowed to stir overnight at room temperature. After 20 hours of reaction time, the reaction mixture was evaporated in vacuo to half of its original volume. 100 mL of water was added, and the solution was extracted with ethyl acetate (2×200 mL), the combined organics washed with water (200 mL) and brine (100 mL), dried over sodium sulfate, filtered and evaporated to give clear, yellow oil. This oil was purified via automated flash chromatography (EPCLC W-Prep 2XY, Yamazen Corp.) using ethyl acetate/hexanes as the eluents. The fractions containing the desired product were combined and evaporated to give 20.9 g (89.5% yield) of 4 as a white solid. $^1$H NMR (300 MHz, CDCl$_3$) δ 7.34 (d, J=8.26 Hz, 2H), 7.25 (d, J=8.17 Hz, 2H), 6.83 (s, br, 1H), 4.74 (s, 2H), 4.49 (d, J=5.80 Hz, 2H), 0.95 (s, 9H), 0.11 (s, 6H). $^{13}$C NMR (75 MHz, CDCl$_3$) δ 157.52, 141.83, 134.51, 128.03, 126.72, 117.90, 64.65, 43.81, 26.04, 18.53, −5.17. HRMS (ESI): calculated mass (C$_{16}$H$_{25}$F$_3$NO$_2$Si) [M+H]$^{1+}$: 348.1607, mass found m/z: 348.1597 [M+H]$^{1+}$.

Synthesis of (4-(((tert-butyldimethylsilyl)oxy)methyl) phenyl)methanamine (5; "NBal"). 20.8 g (59.9 mmol) of 4 was dissolved in methanol (100 mL), followed by the addition of a 2 M aqueous solution of potassium carbonate (27.1 g in 100 mL water). The reaction was heated to reflux for seven hours, and then allowed to cool to room temperature. Methanol was evaporated from the reaction mixture in vacuo, the remaining aqueous solution was transferred to a separatory funnel, and was extracted with DCM (2×400 mL). The combined organics were washed with water (100 mL), dried over sodium sulfate, filtered and evaporated in vacuo to give a yellow oil. The crude product was purified via automated flash chromatography (EPCLC W-Prep 2XY, Yamazen Corp.) with an increasing gradient of DCM/MeOH w/1% TEA. The fractions containing the desired material were combined and evaporated to give 12.35 g (82.0% yield) of 5 as a clear oil, which solidified upon storage at −20° C. $^1$H NMR (500 MHz, CDCl$_3$) δ 7.28 (d, J=8.58 Hz, 2H), 7.25 (d, J=8.14 Hz, 2H), 4.72 (s, 2H), 4.43 (s, br, 1H), 3.81 (s, 2H), 0.95 (s, 9H), 0.10 (s, 6H). $^{13}$C NMR (126 MHz, CDCl$_3$) δ 141.85, 139.83, 126.87, 126.18, 64.70, 46.16, 29.35, 25.90, −5.29. HRMS (ESI): calculated mass (C$_{17}$H$_{27}$NOSi) [M+H]$^{1+}$: 252.1784, mass found m/z: 252.1785 [M+H]$^{1+}$.

Synthesis of NBza

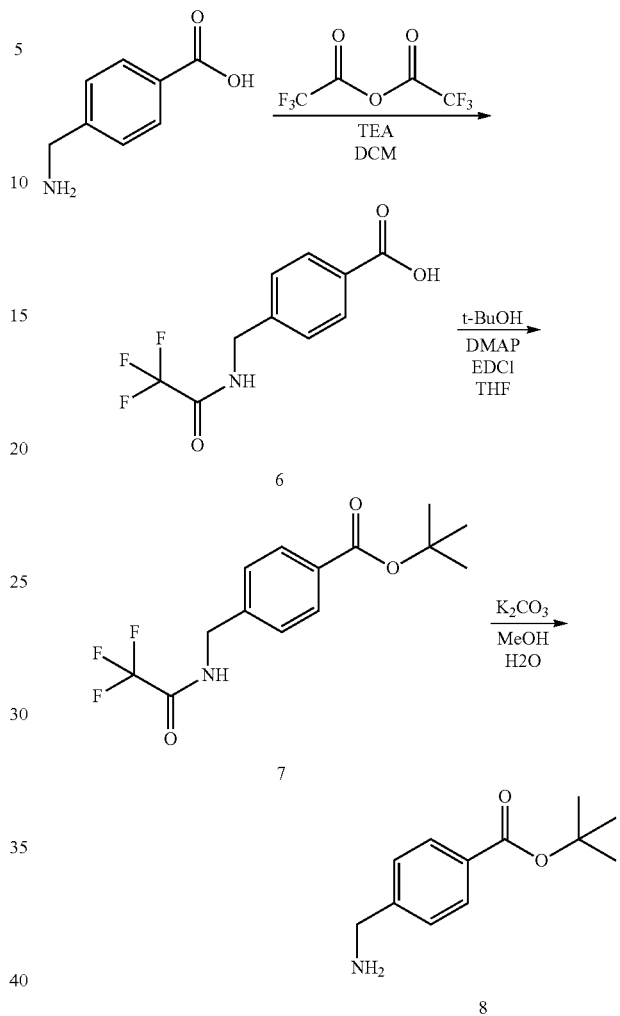

Synthesis of 4-((2,2,2-trifluoroacetamido)methyl)benzoic acid (6). 21.16 g (140 mmol) of 4-(aminomethyl) benzoic acid was suspended in 450 mL of dichloromethane, followed by 42.0 mL (301 mmol) of triethylamine. The reaction was then cooled in an ice bath, and 60.44 g (2.06 eq.) of trifluoroacetic anhydride in 50 mL of dichloromethane was added dropwise over the course of 1 hour. The reaction was stirred for an additional three hours while being allowed to gradually warm to room temperature. 500 mL of aqueous saturated sodium bicarbonate solution was then slowly added to the reaction mixture in portions, and the solution was acidified with 4 N HCl (pH<3). The resultant precipitate was collected via filtration, and the filter cake was washed three times with water and twice with ice-cold ether. The solid was dissolved in ethyl acetate, dried over sodium sulfate, filtered, transferred to a round bottom flask and evaporated to give an off-white solid. The product was recrystallized from ethyl acetate/hexanes three times to give 24.63 g (71.19% yield) of 6 as a white solid. $^1$H NMR (300 MHz, DMSO) δ 10.15 (t, J=5.91 Hz, 1H), 8.13 (d, J=8.36 Hz, 2H), 7.51 (d, J=8.38 Hz, 2H), 4.52 (d, J=5.97 Hz, 2H). $^{13}$C NMR (75 MHz, DMSO) δ 167.97, 162.96, 145.92, 131.66, 130.49, 128.91, 127.95, 43.27.

Synthesis of tert-butyl 4-((2,2,2-trifluoroacetamido) methyl)benzoate (7). 12.55 g (50.77 mmol) of 6 was dissolved in anhydrous THF (150 mL), and 135 mL of t-butanol and 6.20 g (50.75 mmol) DMAP were added. The reaction was cooled to 0° C. under argon, and 29.2 g (152 mmol) of EDCI was added followed by an additional 50 mL of anhydrous THF to wash down the insides of the reaction flask. The reaction was sealed and stirred under argon overnight, allowing it to gradually reach room temperature. After 16 hours of reaction time, 200 mL of water was added to the reaction and the organics were evaporated in vacuo. The aqeuous solution was extracted with DCM (2×200 mL), and the subsequent combined organics were washed with 5% HCl (2×200 mL), 200 mL of water and 200 mL of brine. The organic layer was dried over sodium sulfate and evaporated to give a yellow oil. The product was purified using normal phase flash chromatography (EPCLC W-Prep 2XY, Yamazen Corp.) with an increasing gradient of ethyl acetate/hexanes (10:90 to 100:0 over 60 minutes). The fractions containing the desired product were combined and evaporated to give 10.78 g (70.0% yield) of 7 as a white solid. $^1$H NMR (300 MHz, DMSO) δ 1.53 (s, 9H), 4.46 (d, J=5.94 Hz, 2H), 7.39 (dt, J=1.78, 8.33 Hz, 2H), 7.89 (dt, J=1.83, 8.33 Hz, 2H), 10.09 (t, J=6.11 Hz, 1H). $^{13}$C NMR (75 MHz, DMSO) δ 27.75, 42.36, 80.63, 116.22, 127.40, 129.31, 130.45, 142.54, 156.56, 164.70. HRMS (ESI): calculated mass ($C_{14}H_{17}F_3NO_3$) [M+H]$^{1+}$: 304.1161, mass found m/z: 304.1170 [M+H]$^{1+}$.

Synthesis of tert-butyl 4-(aminomethyl)benzoate (8; "NBza"). 10.75 g (35.5 mmol) of 7 was dissolved in methanol (45 mL), and 12.25 g (2.5 eq.) of potassium carbonate dissolved in water (45 mL) was added in one portion. The reaction was sealed and stirred overnight at room temperature. After 18 hours of reaction time, methanol was evaporated from the reaction mixture and the remaining aqueous solution was adjusted to pH>10 with 4 N NaOH. The aqueous layer was extracted with DCM (3×200 mL), the combined organics washed with water (50 mL) and brine (50 mL), and the organic layer dried over sodium sulfate. The organics were evaporated to give 7.10 g (96.7% yield) of 8 as a clear oil. $^1$H NMR (300 MHz, CDCl$_3$) δ 7.91 (d, J=8.30 Hz, 2H), 7.31 (d, J=8.32 Hz, 2H), 3.86 (s, 2H), 1.69 (s, 1H), 1.55 (s, 9H). $^{13}$C NMR (75 MHz, CDCl$_3$) δ 165.57, 147.58, 130.47, 129.60, 126.71, 80.76, 46.02, 28.12. HRMS (ESI): calculated mass ($C_{12}H_{18}NO_2$) [M+H]$^{1+}$: 208.1338, mass found m/z: 208.1334 [M+H]$^{1+}$.

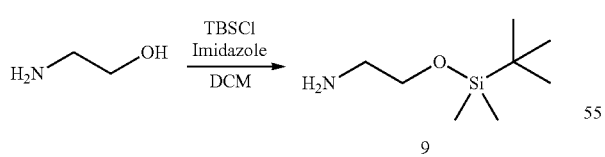

9

Synthesis of 2-((tert-butyldimethylsilyl)oxy)ethan-1-amine (9; "NEal"). 6.11 g (100 mmol) of ethanolamine and 13.62 g (2 equiv.) of imidazole were dissolved in DCM (100 mL) in a 500 mL round bottom flask. 15.83 g (105 mmol) of tert-butyldimethylchlorosilane dissolved in DCM (50 mL) was added dropwise over the course of 20 minutes, and the reaction mixture was stirred for one hour at room temperature. At that time, all of the starting material had been consumed as confirmed by TLC; 100 mL of water was added and the layers were separated. The aqueous layer was extracted twice with DCM (2×100 mL), and the combined organics washed with water (50 mL), dried over sodium sulfate and evaporated to give 13.68 g (77.9% yield) of 9 as a clear oil. $^1$H NMR (300 MHz, CDCl$_3$) δ 3.57 (t, J=5.36 Hz, 2H), 2.71 (t, J=5.25 Hz, 2H), 2.08 (s, 2H, NH$_2$), 0.84 (s, 9H), 0.00 (s, 6H). $^{13}$C NMR (75 MHz, CDCl$_3$) δ 65.13, 44.27, 25.96, 18.35, −5.27. HRMS (ESI) calculated mass ($C_9H_{22}NOSi$) [M+H]$^{1+}$: 188.1471, mass found m/z: 188.1495 [M+H]$^{1+}$.

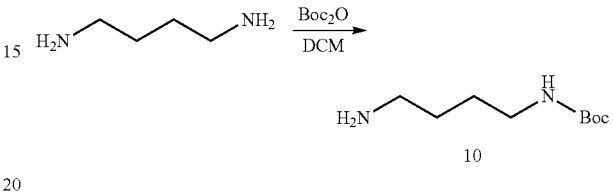

10

Synthesis of tert-butyl (4-aminobutyl)carbamate (10; "NLys"). 50.02 g (567.4 mmol) of 1,4-diaminobutane was dissolved in chloroform (600 mL) and was cooled to 0° C. 13.17 g (6.03 mmol) of di-tert-butyl dicarbonate dissolved in chloroform (300 mL) was added drop-wise over the course of two hours and the reaction was stirred overnight, allowing it to reach room temperature. After 21 hours of reaction time, the entire reaction mixture was transferred to a separatory funnel and was washed with water (8×200 mL), dried over sodium sulfate and evaporated in vacuo to give 10.71 g (94.3% yield) of 10 as a clear oil. $^1$H NMR (300 MHz, CDCl$_3$) δ 4.84 (s, 1H), 3.04 (t, 2H), 2.64 (t, J=6.7 Hz, 2H), 1.46-1.38 (m, 4H), 1.37 (s, 9H). $^{13}$C NMR (75 MHz, CDCl$_3$) δ 155.93, 78.82, 41.70, 40.30, 30.77, 28.32, 27.37. HRMS (ESI) calculated mass ($C_9H_{21}N_2O_2$) [M+H]$^{1+}$: 189.1603, mass found m/z: 189.1601 [M+H]$^{1+}$.

Synthesis of NTrp

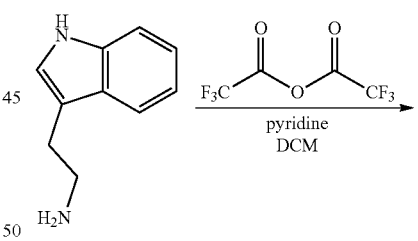

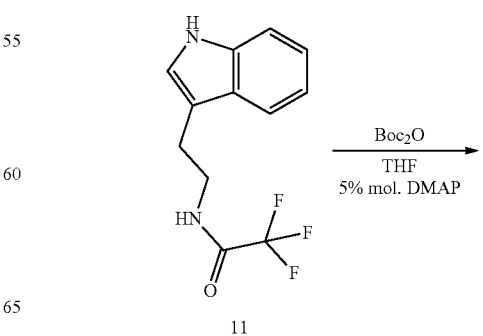

11

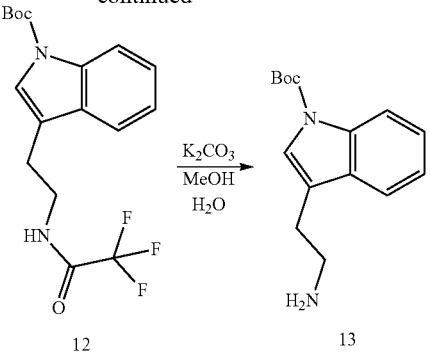

Synthesis of N-(2-(1H-indol-3-yl)ethyl)-2,2,2-trifluoroacetamide (11). 19.99 g (124.8 mmol) of tryptamine (AK Scientific, Inc., Union City, Calif.) was dissolved in DCM (300 mL) followed by the addition of 11.1 mL (1.1 equiv.) of pyridine. This solution was cooled to 0° C. and 19.4 mL (1.1 equiv.) of trifluoroacetic anhydride was added dropwise. After 22 hours of reaction time, all of the starting material had been consumed, as evidenced by TLC; the reaction mixture was washed with 2N HCl (3×250 mL), water (100 mL) and brine (100 mL), dried over sodium sulfate and evaporated to give a brown solid. This solid was dissolved in a mixture of acetone and DCM and was absorbed onto silica gel. This was dry loaded into an empty flash column, and the product was purified via normal phase flash chromatography (EPCLC W-Prep 2XY, Yamazen Corp.) using an increasing solvent gradient of ethyl acetate/hexanes (20:80 to 100:0 over 60 minutes). The fractions containing the desired product were combined and evaporated to give 24.1 g (75.3% yield) of 11 as a white solid. $^1$H NMR (300 MHz, DMSO) δ 10.86 (s, 1H, NH), 9.55 (t, J=5.56 Hz, 1H), 7.53 (d, J=7.72 Hz, 1H), 7.34 (dd, J=1.05, 7.99 Hz, 1H), 7.16 (d, J=2.35 Hz, 1H), 7.07 (td, J=1.25, 7.55, 8.09 Hz, 1H), 6.98 (ddd, J=1.13, 7.10, 7.90 Hz, 1H), 3.45 (q, J=6.82 Hz, 2H).

Synthesis of tert-butyl 3-(2-(2,2,2-trifluoroacetamido)ethyl)-1H-indole-1-carboxylate (12). 24.0 g (93.7 mmol) of 11 was dissolved in THF (200 mL), followed by 30.76 g (1.5 equiv.) of di-tert-butyl dicarbonate with an additional 50 mL of THF to wash down the sides of the flask. 0.59 g (0.052 equiv.) of DMAP was then added and the reaction was heated to 40° C. for two hours. At that time, TLC showed that all of the starting material had been consumed, so 250 mL of DCM was added to the reaction and the organic solution was washed with water (2×100 mL), dried over sodium sulfate and evaporated in vacuo to give a viscous brown oil. The product was purified via normal phase flash chromatography (EPCLC W-Prep 2XY, Yamazen Corp.) using an increasing gradient of ethyl acetate/hexanes (10:90 to 100:0 over 100 minutes). The fractions containing the desired product were combined and evaporated in vacuo to give 17.27 g (51.7% yield) of 12 as a white solid. $^1$H NMR (300 MHz, DMSO) δ 9.57 (t, J=5.78 Hz, 1H), 8.05 (d, J=8.20 Hz, 1H), 7.62 (d, J=7.48 Hz, 1H), 7.50 (s, 1H), 7.33 (td, J=1.39, 7.77, 8.28 Hz, 1H), 7.25 (td, J=1.17, 7.44 Hz, 1H), 3.49 (q, J=6.72 Hz, 2H), 2.91 (t, J=6.98 Hz, 2H), 1.61 (s, 9H). $^{13}$C NMR (75 MHz, DMSO) δ 156.51, 156.03, 149.02, 134.78, 130.13, 124.42, 123.18, 122.52, 119.07, 117.40, 114.74, 83.48, 39.07, 27.67, 23.53.

Synthesis of tert-butyl 3-(2-aminoethyl)-1H-indole-1-carboxylate (13; "NTrp"). 17.20 g (48.27 mmol) of 12 was dissolved in methanol (60 mL) followed by the addition of 16.75 g (2.511 equiv.) of potassium carbonate dissolved in water (60 mL). The reaction flask was covered and the reaction was allowed to stir overnight at room temperature. After 16 hours of reaction time, little progress was seen with the reaction, so it was heated to reflux for seven hours. At that time, TLC showed that all starting material had been consumed. Methanol was evaporated in vacuo, and the remaining aqueous solution was adjusted to pH>10 with 4 N NaOH. The product was extracted with DCM (3×200 mL), and the combined organics were washed with water (100 mL) and brine (100 mL), dried over sodium sulfate, filtered and evaporated in vacuo to give 7.05 g (56.1% yield) of 13 as a yellow oil. $^1$H NMR (300 MHz, CDCl$_3$) δ 7.60-7.46 (m, 1H), 7.46-7.36 (m, 1H), 7.34-7.17 (m, 3H), 3.54 (t, J=7.74 Hz, 2H), 3.03 (t, J=7.11 Hz, 2H), 1.66 (s, 9H), 1.64 (s, 2H, NH$_2$). $^{13}$C NMR (75 MHz, CDCl$_3$) δ 167.81, 135.55, 130.74, 124.17, 123.05, 122.72, 122.26, 118.98, 115.15, 83.27, 51.28, 28.17, 26.50. HRMS (ESI) calculated mass (C$_{15}$H$_{21}$N$_2$O$_2$) [M+H]$^{1+}$: 261.1603, mass found m/z: 261.1598 [M+H]$^{1+}$.

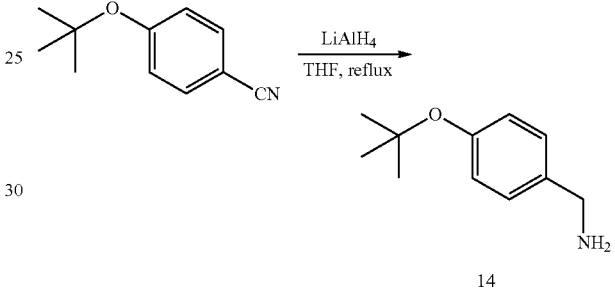

Synthesis of (4-(tert-butoxy)phenyl)methanamine (14; "NTyr"). 175 mL of 1M (175 mmol; 2.6 eq.) lithium aluminum hydride in THF was added to a round bottom flask with a stir bar and was cooled to 0° C. A solution of 11.83 g (67.5 mmol) of 4-(tert-butoxy)benzonitrile (Alfa Aesar, Ward Hill, Mass.) in 50 mL of anhydrous THF was added to the stirring solution dropwise over the course of 30 minutes. The reaction was then fitted with a reflux condenser and was heated to reflux for six hours, followed by stirring overnight under argon, allowing the reaction to cool to room temperature. After 22 hours of total reaction time, the reaction mixture was cooled to 0° C. and was quenched with 7 mL of water, followed by 6 mL of 15% NaOH (aq) and an additional 17 mL of water. The resulting emulsion was filtered over celite, with the filter cake being washed with methanol (2×50 mL) and DCM (2×50 mL). The filtrate was evaporated, and the resulting dark yellow oil was dissolved into 75 mL of water. The solution was transferred to a separatory funnel and was extracted with ethyl acetate (4×150 mL). The combined extractions were washed with water (100 mL) and brine (100 mL), dried over sodium sulfate, and evaporated in vacuo to give a dark yellow oil. The oil was separated using basic alumina chromatography and a solvent system of ethyl acetate/hexanes (20:80 to 50:50). The fractions containing the product (as evidenced by TLC) were combined and evaporated to give 5.71 g (47.2% yield) of 14 as a clear oil. $^1$H NMR (300 MHz, CDCl$_3$) δ 7.19 (dd, J=2.26, 6.46 Hz, 2H), 6.94 (dd, J=2.32, 6.46 Hz, 2H), 4.38 (s, 2H), 1.31 (s, 9H). $^{13}$C NMR (75 MHz, CDCl$_3$) δ 153.80, 135.32, 128.26, 124.27, 78.17, 54.93, 28.75. LRMS (EI) calculated mass (C$_{11}$H$_{18}$NO) [M+H]$^{1+}$: 180.1388, mass found m/z: 180.1404 [M+H]$^{1+}$.

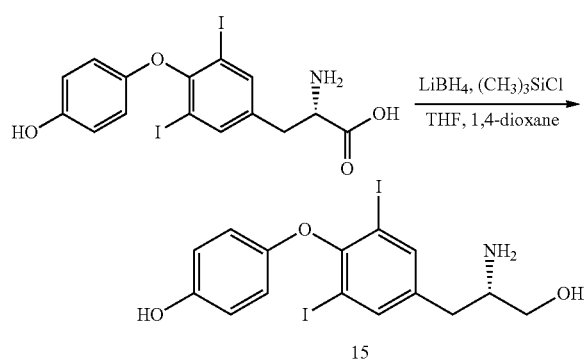

Synthesis of (S)-4-(4-(2-amino-3-hydroxypropyl)-2,6-diiodophenoxy)phenol (15; "T2AA"). 7.55 mL of 1M (15.1 mmol) lithium borohydride in THF was added to a 50 mL round bottom flask followed by 5.2 mL of anhydrous THF and 5 mL of anhydrous dioxane. The solution was cooled to 0° C. under argon, and 3.85 mL (30.3 mmol) of chlorotrimethylsilane was slowly added. The resulting solution was stirred for 15 minutes at 0° C., and 0.90 g (1.71 mmol) of 3,5-diiodo-L-thyronine (Combi-Blocks, Inc.) was added in one portion with the aid of an additional 5.2 mL of anhydrous THF and 5 mL of anhydrous dioxane. The flask was sealed and the reaction was stirred overnight under argon while being allowed to slowly warm to room temperature. After 18 hours of reaction time, the reaction was poured into 25 mL of ice-water, adjusted to pH>9 with 4N NaOH and was extracted with ethyl acetate (3×50 mL). The combined organic extractions were dried over sodium sulfate, filtered and evaporated to give a light brown solid. This solid was dissolved in a mixture of ACN/$H_2O$ (75:25) and was purified on an Agilent ZORBAX SB-$C_{18}$ reverse phase semi-preparative column on a System Gold 166 (Beckman Coulter) HPLC system, using a gradient of ACN (0.1% TFA)/$H_2O$ (0.1% TFA) 0:100 to 100:0 over 30 minutes with detection at 254 nm. The fractions containing the purified product were combined, frozen and lyophilized to give 460 mg (52.5% yield) of 15 as a fluffy white solid. $^1H$ NMR (300 MHz, DMSO) δ 9.12 (s, 1H), 7.84 (s, 5H), 6.68 (dt, J=2.30, 3.84, 9.08 Hz, 2H), 6.54 (dt, J=2.30, 3.61, 8.98 Hz, 2H), 5.39 (t, J=4.49 Hz, 1H), 3.56 (dd, J=4.86, 7.97 Hz, 1H), 3.40 (dq, J=5.48, 9.94 Hz, 2H), 2.87-2.69 (m, 2H), 2.07 (s, 1H). $^{13}C$ NMR (126 MHz, DMSO) δ 152.65, 152.26, 148.83, 140.67, 137.48, 115.86, 115.82, 92.48, 60.07, 53.27, 40.02, 39.85, 39.78, 39.69, 39.52, 39.35, 39.19, 39.02, 33.06. HRMS (ESI) calculated mass ($C_{15}H_{16}I_2NO_3$) $[M+H]^{1+}$: 511.9220, mass found m/z: 511.9678 $[M+H]^{1+}$.

General Method for Synthesis of Peptoid Trimers. Trimeric peptoids were synthesized using an adapted procedure for submonomer peptoid synthesis (Zuckermann, R. N., et al. *J. Am. Chem. Soc.* 1992, 114 (26), 10646-10647). Briefly, 0.05 mmol of Rink Amide AM or MBHA resin was transferred to a 25 mL glass fritted peptide reaction vessel and was swelled with DMF for 30 minutes. The resin was then deprotected using two 2.5 ml portions of 20% piperidine in DMF with incubation times of 15 minutes for each addition at room temperature. Following washing of the resin with DMF (6×) and DCM (3×), deprotection was confirmed by a ninhydrin (Kaiser's) test for primary amines. A solution of 1.5 mL of 1M bromoacetic acid (30 equiv.) in DMF and 230 µL (29.4 equiv.) of N,N'-diisopropylcarbodiimide (DIC) was added, and the resin was placed on an orbital shaker for 1 hour at 37° C. At that time, the resin was washed with DMF (6×) and DCM (3×), and a solution of 1M respective primary amine (2M for commercially available primary amines) in DMF was added, with incubation on an orbital shaker for 2 hours at 37° C. These steps were repeated with washing steps in-between to produce the desired peptoid sequence. For the coupling of T2AA, peptoids were first synthesized up to the final bromoacetic acid addition. A solution of 500 mg (19.5 equiv.) of T2AA and 34 µL (39 equiv.) of DIEA in 2.5 mL of DMF was added, and the resin was incubated overnight at room temperature on an orbital shaker. Peptoids were cleaved from resin using a solution of TFA/TIS/water (95:2.5:2.5), incubating the resin at room temperature for either 1 hour, or 3 hours in the case of peptoids containing NArg, NEal or NBal side chains. TFA was removed with a steady stream of blowing air, and the remaining residue was dissolved in ACN/$H_2O$ (50:50) with 0.1% TFA, frozen and lyophilized. The peptoids were purified via HPLC (Beckman Coulter System Gold 166 or 168) using an increasing gradient of ACN/$H_2O$ with 0.1% TFA (5:95) to (100:0) over 30 minutes on an Agilent ZORBAX SB-$C_{18}$ reverse phase semi-preparative column. Molecular masses were validated via low resolution ESI or APCI experiments, and exact masses were obtained by high resolution ESI or MALDI-TOF.

Synthesis of Fluorescein-labeled POGO Ligase Peptide (FAM-PL). POGO Ligase peptide (sequence: SAVLQK-KITDYFHPKK, SEQ ID NO: 2) was synthesized by GenScript USA Inc. and provided uncleaved on Rink Amide MBHA resin. 0.10 mmol of this resin was transferred to a glass fritted peptide reaction vessel and swelled in DMF for 30 minutes, followed by washing with DCM (3×). Sufficient deprotection of the final amino acid residue was confirmed by a ninhydrin (Kaiser's) test for primary amines. An aminohexanoic acid linker was added (1 mmol Fmoc-6-Ahx-OH, 2.1 ml of 0.45M HCTU, 500 µL of 4M DIEA in NMP; 2 hours at room temperature) to separate the fluorescent dye from the peptide sequence. Following subsequent washing of the resin (DMF (6×) and DCM (3×)) and Fmoc deprotection (20% piperidine in DMF; 30 minutes at room temperature), the resin was again washed (DMF (6×) and DCM (3×)) and then transferred to a glass scintillation vial wrapped in foil. A solution of 75.3 mg of 5-FAM, 80.7 mg of HCTU and 46 mg of DIEA in 2 mL of DMF was added, and the resin was then placed on an orbital shaker overnight at room temperature. After 20 hours of incubation time, the resin was washed with DMF (6×) and DCM (3×), dried over vacuum, transferred to a glass scintillation vial and cleaved from resin using a solution of trifluoroacetic acid (TFA)/triisopropylsilane (TIS)/water (95:2.5:2.5) for 3 hours at room temperature in the dark. The 5-FAM-labeled POGO ligase peptide (FAM-PL, SEQ ID NO: 4) was then precipitated into ice cold diethyl ether and collected by centrifugation at 4,000×g for 10 minutes at 4° C. It was purified via HPLC (Beckman Coulter System Gold 168) using an increasing gradient of acetonitrile/water with 0.1% TFA (5:95) to (100:0) over 30 minutes. The molecular mass and sequence were validated via MALDI-TOF/TOF. Purity was determined by HPLC using absorbencies at 219 and 280 nm. HRMS (LCMS): calculated mass ($C_{116}H_{164}N_{25}O_{29}$) $[M-H]^{1-}$: 2372.6980, mass found m/z: 2372.7221 $[M-H]^{1-}$.

Fluorescence Polarization Z'-Factor Analysis. 10 µL of 20 nM FAM-PL in FP binding buffer (25 mM HEPES at pH 7.4, 10% glycerol, 0.01% Triton X-100) was combined with either 10 µL of 200 nM recombinant $(His)_6$-PCNA protein (SEQ ID NO: 3) in binding buffer or 10 µL of binding buffer in each of 48 wells on a ProxiPlate-384 F Plus low volume, black, opaque plate (24 replicates per set). The plate was allowed to incubate at room temperature in the dark for 30 minutes prior to fluorescent measurement. Fluorescence polarization and resultant anisotropy were measured on a BioTek Synergy 4 Multi-Detection Microplate Reader (BioTek Instruments Inc., Winooski, Vt.) using an excitation filter of 485 nm and an emission filter of 530 nm, each with a 20 nm band-pass. The average of each control set was calculated along with the standard deviation. The Z'-factor was calculated using equation 1, $$Z' = 1 - \frac{3\sigma_+ + 3\sigma_-}{|\mu_- - \mu_+|} \tag{1}$$

wherein $\sigma_+$ is the standard deviation of the positive control (FAM-PL peptide in the presence of PCNA protein), $\sigma_-$ is the standard deviation of the negative control (FAM-PL peptide in the absence of PCNA protein), and $\mu_+$ and $\mu_-$ are the mean anisotropy values of the positive and negative controls, respectively.

Fluorescence Polarization Binding Assay. Increasing amounts of recombinant (His)$_6$-PCNA protein (SEQ ID NO: 3) were prepared in FP binding buffer (25 mM HEPES at pH 7.4, 10% glycerol, 0.01% Triton X-100), with an 11-step 2-fold dilution series, and a top concentration of 30 µM. 10 µL of each solution was combined with 10 µL of 20 nM FAM-PL peptide formulated in FP binding buffer in a single well of a ProxiPlate-384 F Plus low volume, black, opaque plate (PerkinElmer). Each concentration of protein was plated in a replicate of four, and the plate was allowed to incubate at room temperature in the dark for 30 minutes prior to fluorescent measurement. Fluorescence polarization and resultant anisotropy were measured on a BioTek Synergy 4 Multi-Detection Microplate Reader using an excitation filter of 485 nm and an emission filter of 530 nm, each with a 20 nm band-pass. The parallel and perpendicular intensity values for each sample (n=4) were used to calculate fractional occupancy (FO) of the FAM-PL peptide bound to monomeric PCNA using equation 2.

$$f_b = \frac{r - r_f}{(r_b - r)Q + r - r_f} \tag{2}$$

wherein:

$$Q = \frac{q_b}{q_f}$$

$$q_f = \|_f + 2 \cdot \perp_f$$

$$q_b = \|_b + 2 \cdot \perp_b$$

and $f_b$ is the fraction of FAM-PL bound to PCNA, r is the observed anisotropy value, $r_f$ is the anisotropy of free un-bound FAM-PL peptide, $r_b$ is the anisotropy of FAM-PL peptide saturated with PCNA protein, Q is the ratio of quantum yield of bound ($q_b$) to free ($q_f$) FAM-PL peptide, $\mu_f$ and $\mu_b$ are the parallel intensities of free un-bound and saturated FAM-PL peptide, respectively, and $\perp_f$ and $\perp_b$ are the perpendicular intensities of free un-bound and saturated FAM-PL peptide, respectively.

FO values were analyzed using non-linear regression statistics in OriginPro 2015, representing them as the mean±standard error of the mean (Y), and plotting them as a function of the monomeric PCNA protein concentration (X). From this, equation 3 was used to obtain a dissociation constant ($K_d$) for FAM-PL:

$$Y = Y_{max} \cdot \frac{X^n}{K_d^n + X^n} \tag{3}$$

wherein n is the Hill slope.

Fluorescence Polarization Competition Assay. Solutions of competitive ligand were formulated from DMSO stocks (10 mM for tripeptoids, 20 mM for T2AA) into FP binding buffer (25 mM HEPES at pH 7.4, 10% glycerol, 0.01% Triton X-100) at appropriate 2× (relative to the desired effective screening concentration) concentrations. 10 µL of each competitive ligand was combined with 5 µL of 4 µM recombinant (His)$_6$-PCNA protein in binding buffer and 5 µL of 40 nM FAM-PL in binding buffer into each well of a ProxiPlate-384 F Plus low volume, black, opaque plate, in replicates of four. DMSO at an equivalent concentration in binding buffer to the concentration of DMSO in the competitive ligand sample was used as a negative control; T2AA at 1 mM was used as a positive control. The plate was allowed to incubate at room temperature in the dark for 30 minutes prior to fluorescent measurement. Fluorescence polarization and resultant anisotropy were measured on a BioTek Synergy 4 Multi-Detection Microplate Reader using an excitation filter of 485 nm and an emission filter of 530 nm, each with a 20 nm band-pass. Anisotropy values were converted to fractional occupancy using equation 2, and IC$_{50}$ values were calculated by fitting the data to equation 4:

$$Y = Y_{min} + \frac{Y_{max} - Y_{min}}{1 + 10^{(\log IC_{50} - X)n}} \tag{4}$$

wherein n is the Hill slope.

Inhibition constants (K$_g$) for the competitive ligands were determined using equation 5, which is a modified form of the Cheng-Prusoff equation, previously reported for fluorescence polarization assays (Nikolovska-Coleska, Z.; et al. Anal. Biochem. 2004, 332 (2), 261-273).

$$K_i = \frac{[I]_{50}}{\left(\frac{[L]_{50}}{K_d} + \frac{[P]_0}{K_d} + 1\right)} \tag{5}$$

Where [l]$_{50}$ is the concentration of each competitive peptoid at 50% inhibition, [L]$_{50}$ is the concentration of the FITC-PL peptide at 50% inhibition, [P]$_0$ is the concentration of monomeric PCNA protein at 0% inhibition, and $K_d$ is the dissociation constant obtained from equation 3.

Molecular Dynamic Simulations. In preparation for molecular dynamic simulations, selected hit peptoids were flexibly docked into the PIP box binding site of the co-crystal structure of PCNA-Pogo Ligase (PL) peptide (PDB ID: 1VYJ), with the peptide itself removed, using Schrödinger Glide's induced-fit docking model. The PCNA crystal structure was prepared using the Protein Preparation Wizard in Maestro, with PCNA minimized in complex with the PL peptide using the OPLS-2005 force field and implicit solvation. PCNA-peptoid complexes were then explicitly solvated in Schrödinger's Desmond[39] using the TI3P water model in the presence of 0.15 M sodium chloride buffer to generate orthorhombic water boxes that contained a 10 Å buffer region. Each system was then minimized with the OPLS-2005 force field.

The molecular dynamic simulations were performed in the same way as described in Pedley, et al., 2016, using Desmond and the OPLS-2005 force field. In summary, long-range electrostatic interactions were determined using a smooth particle mesh Ewald method with a grid spacing of 0.8 Å. For non-bonded van der Waals interactions, a cut off of 9.0 Å was set. All simulations were performed for 5.0 ns, except in cases where simulations did not fully converge after 5.0 ns (simulations were extended by 2.5 ns in those situations), using the Desmond NPT ensemble with a six step slow relaxation protocol prior to the molecular dynamics run: (i) 2000 step limited-memory Broyden-Fletcher-Goldfarb-Shanno (L-BFGS) minimization with a loose convergence restraint of 50 kcal/mol/Å; (ii) 2000 step L-BFGS minimization with a convergence constraint of 5 kcal/mol/Å; (iii) a 12 ps Berendsen NVT simulation at a temperature of 10 K with restraints on solute heavy atoms; (iv) a 12 ps Berendsen NPT ensemble at a temperature of 10 K and pressure at 1.01325 bar with restraints on solute heavy atoms; (v) a 24 ps Berendsen NPT ensemble at a temperature of 300 K and a pressure at 1.01325 bar with restraints on solute heavy atoms; (vi) a 24 ps Berendsen NPT ensemble at a temperature of 300 K and a pressure at 1.01325 bar with restraints on residues beyond 15 Å of the restrained ligand. The 5.0 ns molecular dynamic simulation run was performed using the NPT ensemble. Temperature of the simulation was kept at 300 K using a Nose-Hoover thermostat. Pressure was maintained at 1.01325 bar using the Martyna-Tobias-Klein method. Energy and trajectory data was recorded at every 1.2 ps and 5.0 ps, respectively.

Upon completion of each simulation, PCNA trajectory data were processed in VMD[40] after removal of each peptoid ligand. For each trajectory, the protein backbone Cα atoms were aligned to the first frame of the simulation to generate RMSD and Cα fluctuations (RMSF) values. Simulations were determined to be converged once RMSD values had stabilized (slope of the RMSD curve over the period of the final 0.5-1.0 ns=0). In preparation for principal component analysis, trajectories for each PCNA-peptoid system were overlaid using the alignment tools in VMD. Additionally, trajectories previously generated from Pedley, et al.,[20] including the systems where PCNA is in complex with the Polymerase δ, PL, p85α, p21, Apo, Akt or Abl peptides, were overlaid with the PCNA-peptoid trajectories for purposes of comparative analysis. Principal component analyses were performed using the Bio3D package[41] in R to analyze the conformational differences between the aligned trajectories over the period of the final 0.5 ns for each simulation (100 snapshots per PCNA-ligand system). The first two orthogonal eigenvectors (principal components—PC1 and PC2) were plotted on the same set of axes. Average trajectory coordinates for the final 50 frames of each simulation were performed in VMD to generate average overall conformations of PCNA in complex with each peptoid.

Bayesian Classifier Method. The Bayesian classifier method was generated using the 2P2I Hunter database containing a total of 1058 compounds, 40 of which are iPPIs (actives) and 1018 are non-iPPIs (decoys).[31,35,36] All compounds in that set were converted from 2D to 3D and minimized using the Accelrys Discovery Studio 4.1 Visualizer (Accelrys, San Diego, Calif.).[42] The tripeptoid ligands consisting the test set were prepared using LigPrep in the Maestro Schrödinger software suite.[24] Four descriptors (Glob, EDmin3, IW4 and CW2) were calculated for each compound according to the method developed by Kuenemann, et al.[32] A Laplacian-corrected Bayesian classifier model was generated using Discovery Studio visualizer.

The invention claimed is:

1. A method for treating a patient of cancer comprising the step of antagonizing Proliferating Cell Nuclear Antigen (PCNA, SEQ ID NO: 1) association with the PCNA-Interacting Protein (PIP) box domain by administration a therapeutically effective amount of one or more compounds of formula (I) to the patient in need thereof:

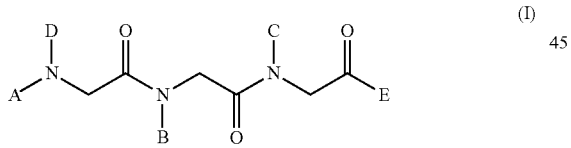

or a pharmaceutically acceptable salt, hydrate, solvate or polymorph thereof, wherein, independently, A is —(CH)$R^1R^2$, wherein $R^1$ is —$(CH_2)_{0-3}$—OH, and $R^2$ is hydrogen, an alkylamino, an alkylguanidino, aminosulfone, an N-alkyl aminosulfone, an alkyl, a cycloalkyl, a heterocyclyl, an aryl, a substituted aryl, a heteroaryl, a substituted heteroaryl, an aralkyl, a substituted aralkyl, a heteroaralkyl, or a substituted heteroaralkyl;

B is hydrogen, an alkyl, a heteroalkyl, a cycloalkyl, a heterocyclyl, an aminoalkyl, a hydroxylalkyl, a mercaptoalkyl, an aryl, a substituted aryl, a heteroaryl, a substituted heteroaryl, an aralkyl, a substituted aralkyl, a heteroaralkyl, or a substituted heteroaralkyl;

C is hydrogen, an alkyl, a heteroalkyl, a cycloalkyl, a heterocyclyl, an aminoalkyl, a hydroxylalkyl, a mercaptoalkyl, an aryl, a substituted aryl, a heteroaryl, a substituted heteroaryl, an aralkyl, a substituted aralkyl, a heteroaralkyl, or a substituted heteroaraalkyl;

D is hydrogen, an alkyl, a heteroalkyl, a cycloalkyl, or a heterocyclyl; and

E is amino, hydroxyl, $NR^3R^4$, or $OR^5$, wherein $R^3$, $R^4$, and $R^5$ are, independently, an alkyl, a cycloalkyl, a heterocyclyl, an aryl, a substituted aryl, a heteroaryl, a substituted heteroaryl, an aralkyl, a substituted aralkyl, a heteroaralkyl, or a substituted heteroaralkyl, wherein said cancer is a prostate, lung, breast, ovarian, colorectal, or pancreatic cancer.

2. The method according to claim 1, wherein A is: —(CH)$R^1R^2$, wherein $R^1$ is —$(CH_2)_{0-3}$—OH, and $R^2$ is:

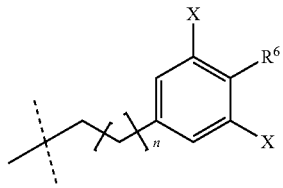

wherein n=0~3; X is hydrogen, halo, a $C_1$-$C_6$ alkyl, or a $C_1$-$C_6$ haloalkyl; $R^6$ is hydrogen, a $C_1$-$C_{12}$ alkyl, a $C_1$-$C_{12}$ cycloalkyl, a $C_1$-$C_{12}$ heterocyclyl, a $C_1$-$C_{12}$ aryl, a $C_1$-$C_{12}$ substituted aryl, a $C_1$-$C_{12}$ heteroaryl, a $C_1$-$C_{12}$ substituted heteroaryl, a $C_1$-$C_{12}$ aralkyl, a $C_1$-$C_{12}$ substituted aralkyl, a $C_1$-$C_{12}$ heteroaralkyl, a $C_1$-$C_{12}$ substituted heteroaralkyl, —$OR^7$, —$NHR^8$, or —$SR^9$, wherein $R^7$, $R^8$, and $R^9$ are a $C_1$-$C_{12}$ alkyl, a $C_1$-$C_{12}$ cycloalkyl, a $C_1$-$C_{12}$ heterocyclyl, a $C_1$-$C_{12}$ aryl, a C$_1$-C$_{12}$ substituted aryl, a C$_1$-C$_{12}$ heteroaryl, a C$_1$-C$_{12}$ substituted heteroaryl, a C$_1$-C$_{12}$ aralkyl, a C$_1$-C$_{12}$ substituted aralkyl, a C$_1$-C$_{12}$ heteroaralkyl, a C$_1$-C$_{12}$ substituted heteroaralkyl.

3. The method according to claim 2, wherein A is: —(CH)R$^1$R$^2$, wherein R$^1$ is —CH$_2$OH, and R$^2$ is

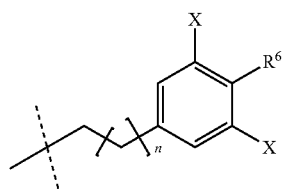

wherein n=0~3; X is hydrogen, halo, a C$_1$-C$_6$ alkyl, or a C$_1$-C$_6$ haloalkyl;

R$^6$ is hydrogen, methyl,

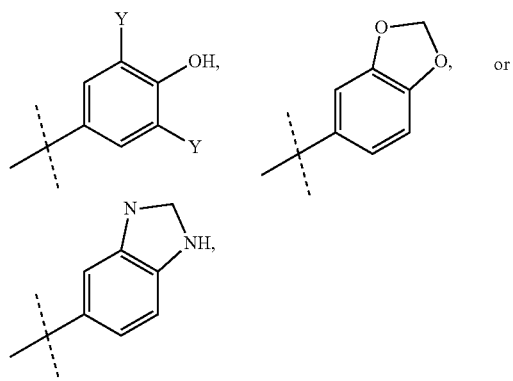

wherein Y is hydrogen, halo, a C$_1$-C$_6$ alkyl, or a C$_1$-C$_6$ haloalkyl.

4. The method according to claim 1, wherein B is: —(CH$_2$)nR$^{10}$ wherein n is 1-3, and R$^{10}$ is hydrogen, a C$_1$-C$_6$ alkyl, a C$_1$-C$_6$ cycloalkyl, a C$_1$-C$_6$ heterocyclyl, a C$_1$-C$_6$ aminoalkyl, a C$_1$-C$_6$ hydroxyalkyl, a C$_1$-C$_6$ mercaptoalkyl,

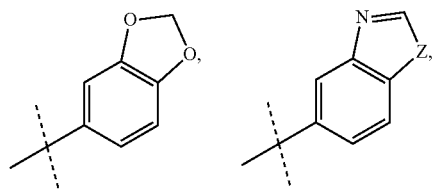

wherein Z is oxygen, nitrogen, thiol, or NCH$_3$, and R$^{11}$ is amino, hydroxyl, a C$_1$-C$_6$ aminoalkyl, or a C$_1$-C$_6$ hydroxyalkyl; wherein C is: —(CH$_2$)nR$^{\prime 2}$ wherein n is 1-3, and R$^{12}$ is hydrogen, a C$_1$-C$_6$ alkyl, a C$_1$-C$_6$ cycloalkyl, a C$_1$-C$_6$ heterocyclyl, a C$_1$-C$_6$ aminoalkyl, a C$_1$-C$_6$ hydroxyalkyl, a C$_1$-C$_6$ mercaptoalkyl,

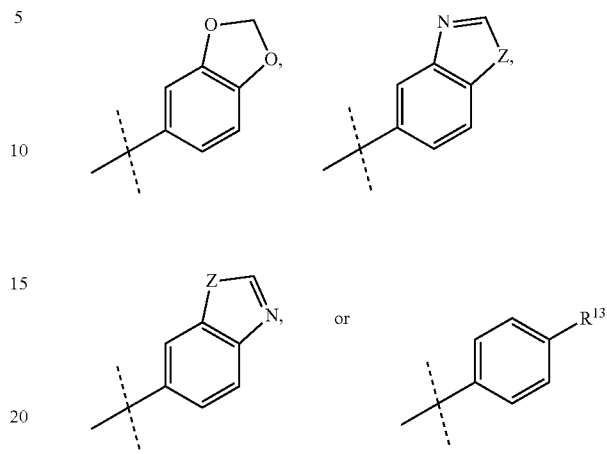

wherein Z is oxygen, nitrogen, thiol, or NCH$_3$, and R$^{13}$ is amino, hydroxyl, a C$_1$-C$_6$ aminoalkyl, or a C$_1$-C$_6$ hydroxyalkyl; and wherein B and C are not both methyl at the same time; wherein B and C are not both hydrogen at the same time.

5. The method according to claim 1, wherein E is: amino, hydroxyl, —N(CH$_3$)$_2$, —OCH$_3$, —OCH$_2$CH$_3$, or —CH$_3$.

6. The method according to claim 1, wherein said compound has the formula (II)

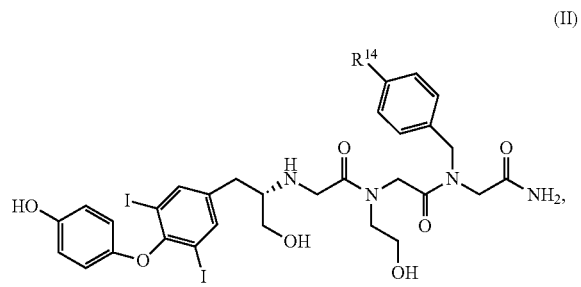

or a pharmaceutically acceptable salt, hydrate, or solvate thereof, wherein R$^{14}$ is hydroxyl or aminomethyl.

7. The method according to claim 1, wherein said compound has the formula (III)

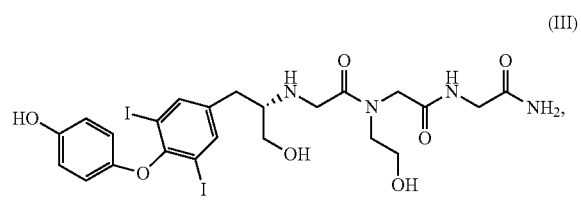 [SMILES: NC(=O)CNC(=O)CN(CCO)C(=O)CN[C@H](CO)Cc1cc(I)c(Oc2ccc(O)cc2)c(I)c1]

or a pharmaceutically acceptable salt, hydrate, or solvate thereof.

8. The method according to claim 1, wherein said compound has the formula (IV)

(IV)

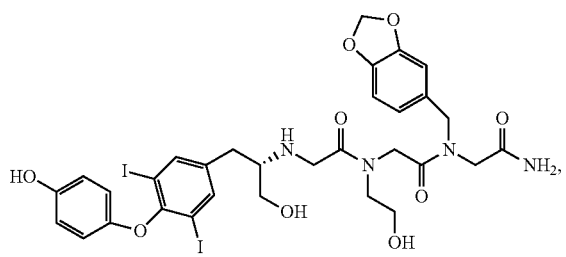

or a pharmaceutically acceptable salt, hydrate, or solvate thereof.

9. A method for sensitizing or synergistic treatment of a patient of cancer using a combination therapy comprising the step of antagonizing Proliferating Cell Nuclear Antigen (PCNA, SEQ ID NO: 1) association with the PCNA-Interacting Protein (PIP) box domain by administration a therapeutically effective amount of one or more compounds of formula (I) to the patient in need thereof, together with one another cancer therapy:

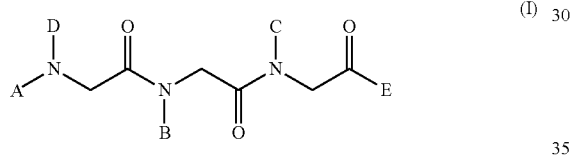
(I)

or a pharmaceutically acceptable salt, hydrate, solvate or polymorph thereof wherein, independently, A is —(CH)$R^1R^2$, wherein $R^1$ is —(CH$_2$)$_{0-3}$—OH, and $R^2$ is hydrogen, an alkylamino, an alkylguanidino, aminosulfone, an N-alkyl aminosulfone, an alkyl, a cycloalkyl, a heterocyclyl, an aryl, a substituted aryl, a heteroaryl, a substituted heteroaryl, an aralkyl, a substituted aralkyl, a heteroaralkyl, or a substituted heteroaralkyl;

B is hydrogen, an alkyl, a heteroalkyl, a cycloalkyl, a heterocyclyl, an aminoalkyl, a hydroxylalkyl, a mercaptoalkyl, an aryl, a substituted aryl, a heteroaryl, a substituted heteroaryl, an aralkyl, a substituted aralkyl, a heteroaralkyl, or a substituted heteroaralkyl;

C is hydrogen, an alkyl, a heteroalkyl, a cycloalkyl, a heterocyclyl, an aminoalkyl, a hydroxylalkyl, a mercaptoalkyl, an aryl, a substituted aryl, a heteroaryl, a substituted heteroaryl, an aralkyl, a substituted aralkyl, a heteroaralkyl, or a substituted heteroaraalkyl;

D is hydrogen, an alkyl, a heteroalkyl, a cycloalkyl, or a heterocyclyl; and

E is amino, hydroxyl, $NR^3R^4$, or $OR^5$, wherein $R^3$, $R^4$, and $R^5$ are, independently, an alkyl, a cycloalkyl, a heterocyclyl, an aryl, a substituted aryl, a heteroaryl, a substituted heteroaryl, an aralkyl, a substituted aralkyl, a heteroaralkyl, or a substituted heteroaralkyl, wherein said cancer is a prostate, lung, breast, ovarian, colorectal, or pancreatic cancer.

10. The method according to claim 9, wherein A is:
—(CH)$R^1R^2$, wherein $R^1$ is —(CH$_2$)$_{0-3}$—OH, and $R^2$ is:

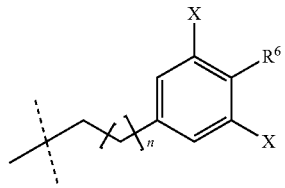

wherein n=0~3; X is hydrogen, halo, a $C_1$-$C_6$ alkyl, or a $C_1$-$C_6$ haloalkyl; $R^6$ is hydrogen, a $C_1$-$C_{12}$ alkyl, a $C_1$-$C_{12}$ cycloalkyl, a $C_1$-$C_{12}$ heterocyclyl, a $C_1$-$C_{12}$ aryl, a $C_1$-$C_{12}$ substituted aryl, a $C_1$-$C_{12}$ heteroaryl, a $C_1$-$C_{12}$ substituted heteroaryl, a $C_1$-$C_{12}$ aralkyl, a $C_1$-$C_{12}$ substituted aralkyl, a $C_1$-$C_{12}$ heteroaralkyl, a $C_1$-$C_{12}$ substituted heteroaralkyl, —$OR^7$, —$NHR^8$, or —$SR^9$, wherein $R^7$, $R^8$, and $R^9$ are a $C_1$-$C_{12}$ alkyl, a $C_1$-$C_{12}$ cycloalkyl, a $C_1$-$C_{12}$ heterocyclyl, a $C_1$-$C_{12}$ aryl, a $C_1$-$C_{12}$ substituted aryl, a $C_1$-$C_{12}$ heteroaryl, a $C_1$-$C_{12}$ substituted heteroaryl, a $C_1$-$C_{12}$ aralkyl, a $C_1$-$C_{12}$ substituted aralkyl, a $C_1$-$C_{12}$ heteroaralkyl, a $C_1$-$C_{12}$ substituted heteroaralkyl.

11. The method according to claim 10, wherein A is:
—(CH)$R^1R^2$, wherein $R^1$ is —CH$_2$OH, and $R^2$ is

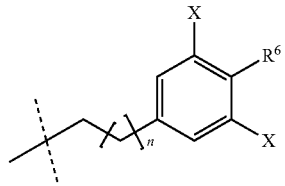

wherein n=0~3; X is hydrogen, halo, a $C_1$-$C_6$ alkyl, or a $C_1$-$C_6$ haloalkyl;

$R^6$ is hydrogen, methyl,

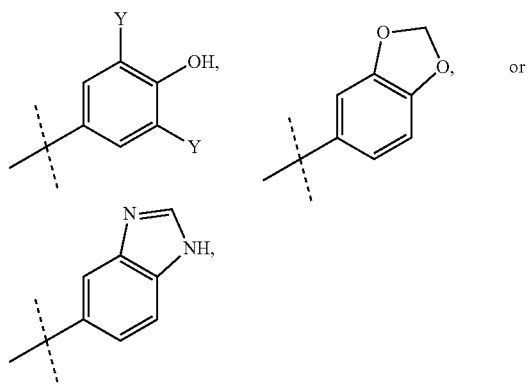

wherein Y is hydrogen, halo, a $C_1$-$C_6$ alkyl, or a $C_1$-$C_6$ haloalkyl.

12. The method according to claim 9, wherein B is: —(CH$_2$)n$R^{10}$ wherein n is 1~3, and $R^{10}$ is hydrogen, a $C_1$-$C_6$ alkyl, a $C_1$-$C_6$ cycloalkyl, a $C_1$-$C_6$ heterocyclyl, a $C_1$-$C_6$ aminoalkyl, a $C_1$-$C_6$ hydroxyalkyl, a $C_1$-$C_6$ mercaptoalkyl,

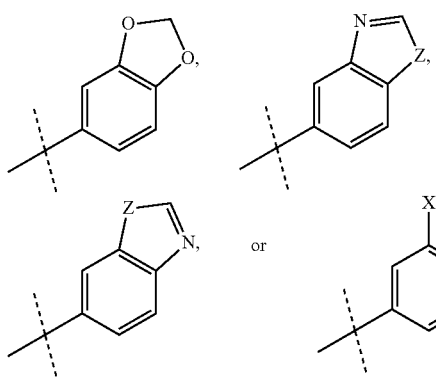

wherein Z is oxygen, nitrogen, thiol, or NCH₃, and $R^{11}$ is amino, hydroxyl, a $C_1$-$C_6$ aminoalkyl, or a $C_1$-$C_6$ hydroxyalkyl; wherein C is: —(CH₂)n$R^{12}$ wherein n is 1~3, and $R^{12}$ is hydrogen, a $C_1$-$C_6$ alkyl, a $C_1$-$C_6$ cycloalkyl, a $C_1$-$C_6$ heterocyclyl, a $C_1$-$C_6$ aminoalkyl, a $C_1$-$C_6$ hydroxyalkyl, a $C_1$-$C_6$ mercaptoalkyl,

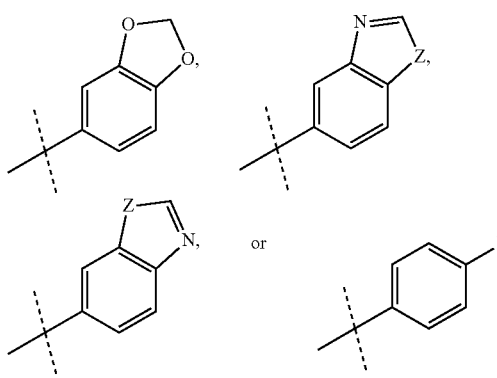

wherein Z is oxygen, nitrogen, thiol, or NCH₃, and $R^{13}$ is amino, hydroxyl, a $C_1$-$C_6$ aminoalkyl, or a $C_1$-$C_6$ hydroxyalkyl; and wherein B and C are not both methyl at the same time; wherein B and C are not both hydrogen at the same time.

13. The method according to claim 9, wherein E is: amino, hydroxyl, —N(CH₃)₂, —OCH₃, —OCH₂CH₃, or —CH₃.

14. The method according to claim 9, wherein said compound has the formula (II)

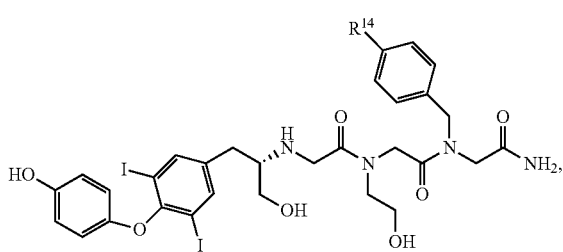

(II)

or a pharmaceutically acceptable salt, hydrate, or solvate thereof, wherein $R^{14}$ is hydroxyl or aminomethyl.

15. The method according to claim 9, wherein said compound has the formula (III)

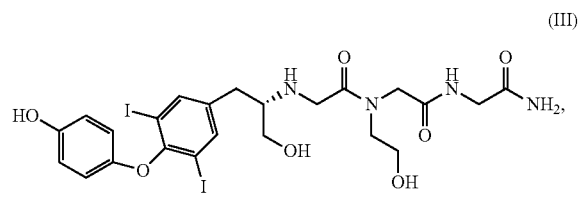 [SMILES: NC(=O)CNC(=O)CN(CCO)C(=O)CN[C@H](CO)Cc1cc(I)c(Oc2ccc(O)cc2)c(I)c1]

(III)

or a pharmaceutically acceptable salt, hydrate, or solvate thereof.

16. The method according to claim 1, wherein said compound has the formula (IV)

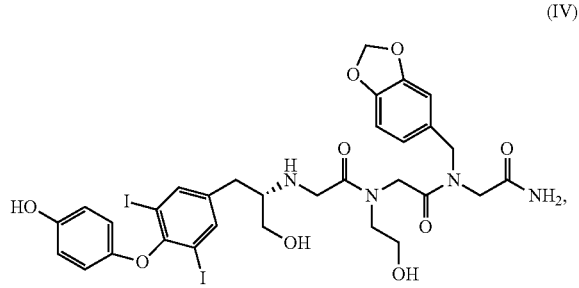 [SMILES: NC(=O)CN(Cc1ccc2c(c1)OCO2)C(=O)CN(CCO)C(=O)CN[C@H](CO)Cc1cc(I)c(Oc2ccc(O)cc2)c(I)c1]

(IV)

or a pharmaceutically acceptable salt, hydrate, or solvate thereof.

17. The method according to claim 9, wherein said one another cancer therapy targets ATM, ATR, DNA-PK, CHEK1, CHEK2, CDK1, CDK4/6, EGFR, PARP1, IGF1-R, or FGFR pharmacological pathway, or a DNA damaging agent comprising doxorubicin, cisplatin and carboplatin, to the patient in need of relief from said cancer.

18. The method according to claim 1, wherein said method further comprising the step of administering a therapeutically effective amount of a compound targeting ATM, ATR, DNA-PK, CHEK1, CHEK2, CDK1, CDK4/6, EGFR, PARP1, IGF1-R, or FGFR pharmacological pathway, or a DNA damaging agent comprising doxorubicin, cisplatin and carboplatin, to the patient in need of relief from said cancer.

* * * * *